United States Patent
Sorge

(10) Patent No.: US 7,183,052 B2
(45) Date of Patent: *Feb. 27, 2007

(54) METHODS FOR DETECTION OF A TARGET NUCLEIC ACID USING MULTI-SUBUNIT PROBES

(75) Inventor: Joseph Sorge, Wilson, WY (US)

(73) Assignee: Stratagene California, Lajjolla, CA (US)

( * ) Notice: Subject to any disclaimer, the term of this patent is extended or adjusted under 35 U.S.C. 154(b) by 331 days.

This patent is subject to a terminal disclaimer.

(21) Appl. No.: 10/196,842

(22) Filed: Jul. 17, 2002

(65) Prior Publication Data

US 2003/0148310 A1    Aug. 7, 2003

Related U.S. Application Data

(60) Provisional application No. 60/313,921, filed on Aug. 21, 2001, provisional application No. 60/307,238, filed on Jul. 23, 2001, provisional application No. 60/306,090, filed on Jul. 17, 2001.

(51) Int. Cl.
C12Q 1/68 (2006.01)
C12P 19/34 (2006.01)
C07H 21/04 (2006.01)

(52) U.S. Cl. .................. 435/6; 435/91.1; 435/91.2; 536/24.3

(58) Field of Classification Search .............. 435/6, 435/91.1, 91.2, 810; 536/24.3
See application file for complete search history.

(56) References Cited

U.S. PATENT DOCUMENTS

| | | | |
|---|---|---|---|
| 4,766,062 A | 8/1988 | Diamond et al. | 435/6 |
| 5,210,015 A | 5/1993 | Gelfand et al. | 435/6 |
| 5,312,728 A * | 5/1994 | Lizardi et al. | 435/6 |
| 5,487,972 A | 1/1996 | Gelfand et al. | 435/6 |
| 5,719,028 A | 2/1998 | Dahlberg et al. | 435/6 |
| 5,837,450 A | 11/1998 | Dahlberg et al. | 435/6 |
| 5,843,669 A | 12/1998 | Kaiser et al. | 435/6 |
| 5,846,717 A | 12/1998 | Brow et al. | 435/6 |
| 5,888,780 A | 3/1999 | Dahlberg et al. | 435/91.53 |
| 5,925,517 A | 7/1999 | Tyagi et al. | 435/6 |
| 5,935,791 A | 8/1999 | Nadeau et al. | 435/6 |
| 6,103,476 A | 8/2000 | Tyagi et al. | 435/6 |
| 6,150,097 A | 11/2000 | Tyagi et al. | 435/6 |
| 6,350,580 B1 * | 2/2002 | Sorge | 435/6 |

(Continued)

OTHER PUBLICATIONS

International Search Report of International Application No. PCT/US02/22721.

*Primary Examiner*—Kenneth R. Horlick
(74) *Attorney, Agent, or Firm*—Elizabeth N. Spar; Kathleen M. Williams; Edwards Angell Palmer & Dodge

(57) ABSTRACT

The invention relates to a method of generating a signal indicative of the presence of a target nucleic acid sequence in a sample, comprising forming a complex by incubating a sample comprising a target nucleic acid sequence with a probe comprising a first and second subunit, and/or an upstream primer, and binding the probe to the target nucleic acid such that the first and second subunits dissociate to release the first subunit and generate a signal. In certain embodiments, the upstream primer is extended with a nucleic acid polymerase to displace at least a portion of the first subunit of the probe from the target nucleic acid strand and dissociate the first and second subunits to release the first subunit of the probe and generate a signal.

31 Claims, 16 Drawing Sheets

U.S. PATENT DOCUMENTS

| | | | |
|---|---|---|---|
| 6,528,254 B1 * | 3/2003 | Sorge | 435/6 |
| 6,548,250 B1 * | 4/2003 | Sorge | 435/6 |
| 6,589,743 B2 * | 7/2003 | Sorge | 435/6 |

* cited by examiner

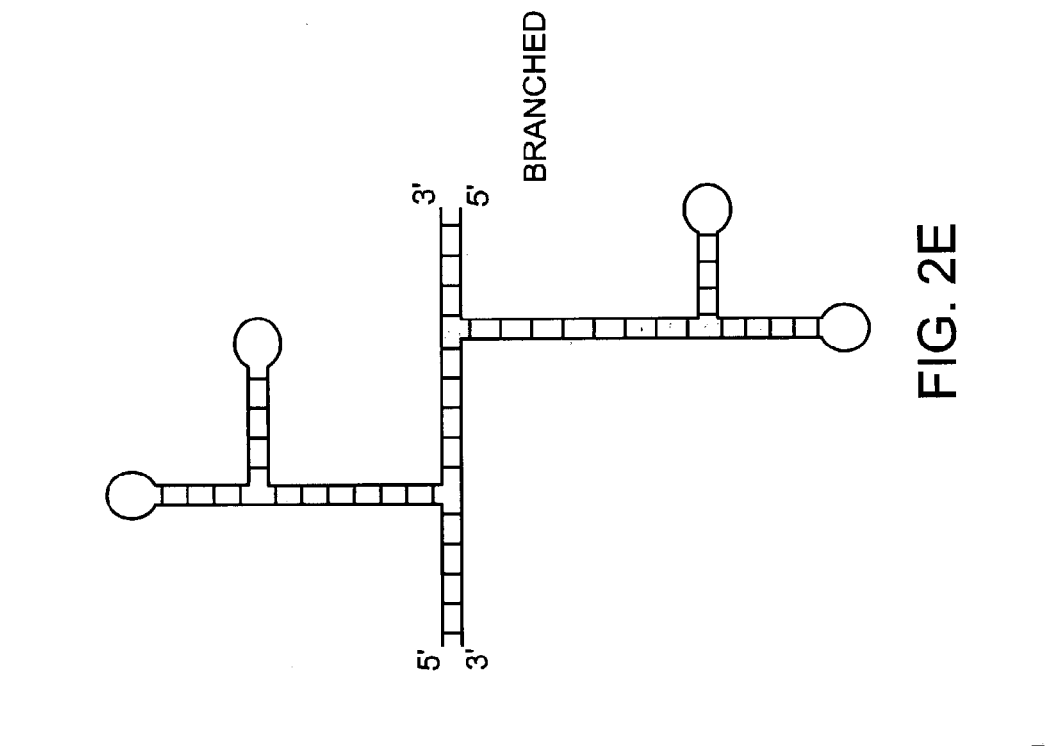
FIG. 2E BRANCHED
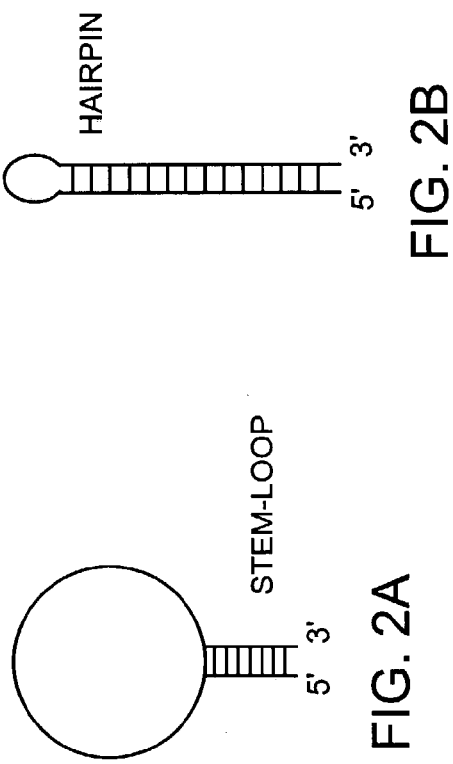
FIG. 2B HAIRPIN
FIG. 2D BULGE
FIG. 2A STEM-LOOP
FIG. 2C INTERNAL LOOP

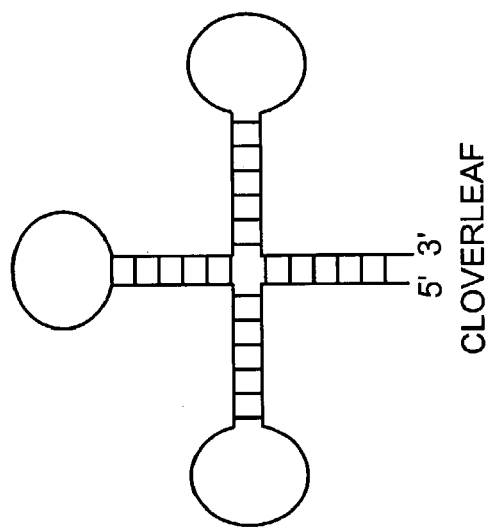
FIG. 2G CLOVERLEAF
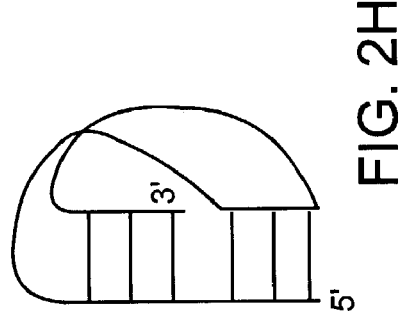
FIG. 2H
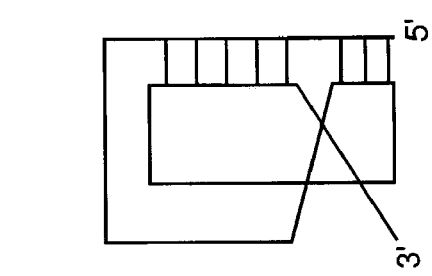
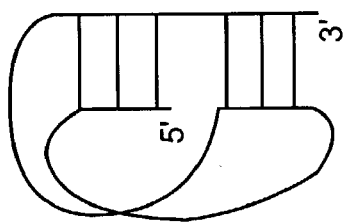
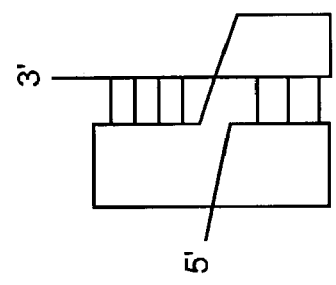
FIG. 2F
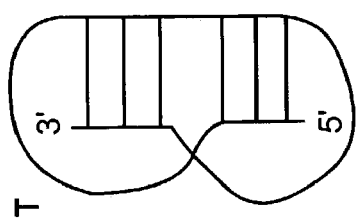
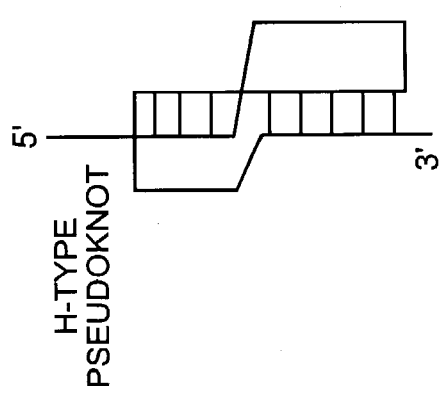
H-TYPE PSEUDOKNOT
PSEUDOKNOT

SEQUENCE LISTING

<160> NUMBER OF SEQ ID NOS: 20

<210> SEQ ID NO 1
<211> LENGTH: 15
<212> TYPE: DNA
<213> ORGANISM: Artificial Sequence
<220> FEATURE:
<223> OTHER INFORMATION: Strand Displacement Amplification Primer B1

<400> SEQUENCE: 1
cgatcgagca agcca      15

<210> SEQ ID NO 2
<211> LENGTH: 14
<212> TYPE: DNA
<213> ORGANISM: Artificial Sequence
<220> FEATURE:
<223> OTHER INFORMATION: Strand Displacement Amplification Primer B2

<400> SEQUENCE: 2

-continued cgagccgctc gctg                                            14

<210> SEQ ID NO 3
<211> LENGTH: 40
<212> TYPE: DNA
<213> ORGANISM: Artificial Sequence
<220> FEATURE:
<223> OTHER INFORMATION: Strand Displacement Amplification Primer S1

<400> SEQUENCE: 3
accgcatcga atgcatgtct cgggtaaggc gtactcgacc                 40

<210> SEQ ID NO 4
<211> LENGTH: 40
<212> TYPE: DNA
<213> ORGANISM: Artificial Sequence
<220> FEATURE:
<223> OTHER INFORMATION: Strand Displacement Amplification Primer S2

<400> SEQUENCE: 4
cgattccgct ccagacttct cgggtgtact gagatcccct                 40

<210> SEQ ID NO 5
<211> LENGTH: 20
<212> TYPE: DNA
<213> ORGANISM: Artificial Sequence
<220> FEATURE:
<223> OTHER INFORMATION: Upstream primer

<400> SEQUENCE: 5
aaggcgtact cgacctgaaa                                      20

<210> SEQ ID NO 6
<211> LENGTH: 21
<212> TYPE: DNA
<213> ORGANISM: Artificial Sequence
<220> FEATURE:
<223> OTHER INFORMATION: Flurogenic probe FAM-DABCYL

<400> SEQUENCE: 6
accatacgga tagggatct c                                     21

<210> SEQ ID NO 7
<211> LENGTH: 20
<212> TYPE: DNA
<213> ORGANISM: Artificial Sequence
<220> FEATURE:
<223> OTHER INFORMATION: Flurogenic probe FAM-DABCYL

<400> SEQUENCE: 7
gcaaagtatc atccctccag                                      20

<210> SEQ ID NO 8
<211> LENGTH: 120
<212> TYPE: DNA
<213> ORGANISM: Artificial Sequence
<220> FEATURE:
<223> OTHER INFORMATION: Amplified synthetic target

<400> SEQUENCE: 8
cctctgcaga ctactattac ataatacgac tcactatagg gatctgcacg tattagccta   60
tagtgagtcg tattaatagg aaacaccaaa gatgatattt cgtcacagca agaattcagg  120

<210> SEQ ID NO 9

```
<211> LENGTH: 20
<212> TYPE: DNA
<213> ORGANISM: Artificial Sequence
<220> FEATURE:
<223> OTHER INFORMATION: Primer P1

<400> SEQUENCE: 9
cctctgcaga ctactattac                                              20

<210> SEQ ID NO 10
<211> LENGTH: 20
<212> TYPE: DNA
<213> ORGANISM: Artificial Sequence
<220> FEATURE:
<223> OTHER INFORMATION: Primer P2

<400> SEQUENCE: 10
cctgaattct tgctgtgacg                                              20

<210> SEQ ID NO 11
<211> LENGTH: 24
<212> TYPE: DNA
<213> ORGANISM: Artificial Sequence
<220> FEATURE:
<223> OTHER INFORMATION: Fluorogenic Probe FAM-DABCYL

<400> SEQUENCE: 11
taggaaacac caaagatgat attt                                         24

<210> SEQ ID NO 12
<211> LENGTH: 95
<212> TYPE: DNA
<213> ORGANISM: Artificial Sequence
<220> FEATURE:
<223> OTHER INFORMATION: Open circle probe

<400> SEQUENCE: 12
gaggagaata aaagtttctc ataagactcg tcatgtctca gcagcttcta acggtcacta    60
atacgactca ctataggttc tgcctctggg aacac                              95

<210> SEQ ID NO 13
<211> LENGTH: 8
<212> TYPE: DNA
<213> ORGANISM: Artificial Sequence
<220> FEATURE:
<223> OTHER INFORMATION: Gap nucleotide for wild-type sequence

<400> SEQUENCE: 13 tagtgatc                                                            8

<210> SEQ ID NO 14
<211> LENGTH: 18
<212> TYPE: DNA
<213> ORGANISM: Artificial Sequence
<220> FEATURE:
<223> OTHER INFORMATION: Rolling circle replication primer

<400> SEQUENCE: 14
gctgagacat gacgagtc                                                18

<210> SEQ ID NO 15
<211> LENGTH: 23
<212> TYPE: DNA
<213> ORGANISM: Artificial Sequence
<220> FEATURE:
<223> OTHER INFORMATION: Upstream primer
```

```
<400> SEQUENCE: 15
aagtttctca taagactcgt cat                                              23

<210> SEQ ID NO 16
<211> LENGTH: 23
<212> TYPE: DNA
<213> ORGANISM: Artificial Sequence
<220> FEATURE:
<223> OTHER INFORMATION: Reverse primer

<400> SEQUENCE: 16
aggcagaacc tatagtgagt cgt                                              23

<210> SEQ ID NO 17
<211> LENGTH: 19
<212> TYPE: DNA
<213> ORGANISM: Artificial Sequence
<220> FEATURE:
<223> OTHER INFORMATION: b171 probe

<400> SEQUENCE: 17
tcgcagtgtc gacctgcga                                                   19

<210> SEQ ID NO 18
<211> LENGTH: 44
<212> TYPE: DNA
<213> ORGANISM: Artificial Sequence
<220> FEATURE:
<223> OTHER INFORMATION: SP170a  probe
<220> FEATURE:
<221> NAME/KEY: misc_feature
<222> LOCATION: (29)..(32)
<223> OTHER INFORMATION: n is a, c, g, or t

<400> SEQUENCE: 18
cagccgtcga tccgcaggtc gacactgcnn nncgtcgacg gctg                       44

<210> SEQ ID NO 19
<211> LENGTH: 12
<212> TYPE: DNA
<213> ORGANISM: Artificial Sequence
<220> FEATURE:
<223> OTHER INFORMATION: Top DNA strand synthesized by poylmerase

<400> SEQUENCE: 19
cagccgtcga cg                                                          12

<210> SEQ ID NO 20
<211> LENGTH: 34
<212> TYPE: DNA
<213> ORGANISM: Artificial Sequence
<220> FEATURE:
<223> OTHER INFORMATION: Unfolded oligonucleotide probe
<220> FEATURE:
<221> NAME/KEY: misc_feature
<222> LOCATION: (19)..(22)
<223> OTHER INFORMATION: n is a, c, g, or t

<400> SEQUENCE: 20
tccgcaggtc gacactgcnn nncgtcgacg gctg                                  34
```

METHODS FOR DETECTION OF A TARGET NUCLEIC ACID USING MULTI-SUBUNIT PROBES

RELATED APPLICATIONS

This application claims the benefit of U.S. Provisional Application No. 60/306,090, filed on Jul. 17, 2001; U.S. Provisional Application No. 60/307,238, filed on Jul. 23, 2001; and U.S. Provisional Application No. 60/313,921, filed on Aug. 21, 2001. The entire teachings of the above application(s) are incorporated herein by reference.

FIELD OF THE INVENTION

The invention relates in general to methods of detecting or measuring a target nucleic acid sequence.

BACKGROUND OF THE INVENTION

Methods of detecting and/or measuring a nucleic acid wherein an enzyme produces a labeled nucleic acid fragment in a cleavage reaction are known in the art.

U.S. Pat. Nos. 5,843,669, 5,719,028, 5,837,450, 5,846,717 and 5,888,780 disclose a method of cleaving a target DNA molecule by incubating a 5' labeled target DNA with a DNA polymerase isolated from *Thermus aquaticus* (Taq polymerase) and a partially complementary oligonucleotide capable of hybridizing to sequences at the desired point of cleavage. The partially complementary oligonucleotide directs the Taq polymerase to the target DNA through formation of a substrate structure containing a duplex with a 3' extension opposite the desired site of cleavage wherein the non-complementary region of the oligonucleotide provides a 3' arm and the unannealed 5' region of the substrate molecule provides a 5' arm. The partially complementary oligonucleotide includes a 3' nucleotide extension capable of forming a short hairpin either when unhybridized or when hybridized to a target sequence at the desired point of cleavage. The release of labeled fragment is detected following cleavage by Taq polymerase.

U.S. Pat. Nos. 5,843,669, 5,719,028, 5,837,450, 5,846,717 and 5,888,780 disclose the generation of mutant, thermostable DNA polymerases that have very little or no detectable synthetic activity, and wild type thermostable nuclease activity. The mutant polymerases are said to be useful because they lack 5' to 3' synthetic activity; thus synthetic activity is an undesirable side reaction in combination with a DNA cleavage step in a detection assay.

U.S. Pat. Nos. 5,843,669, 5,719,028, 5,837,450, 5,846,717 and 5,888,780 disclose that wild type Taq polymerase or mutant Taq polymerases that lack synthetic activity can release a labeled fragment by cleaving a 5' end labeled hairpin structure formed by heat denaturation followed by cooling, in the presence of a primer that binds to the 3' arm of the hairpin structure. Further, U.S. Pat. Nos. 5,843,669, 5,719,028, 5,837,450, 5,846,717 and 5,888,780 teach that the mutant Taq polymerases lacking synthetic activity can also cleave this hairpin structure in the absence of a primer that binds to the 3' arm of the hairpin structure.

U.S. Pat. Nos. 5,843,669, 5,719,028, 5,837,450, 5,846,717 and 5,888,780 also disclose that cleavage of this hairpin structure in the presence of a primer that binds to the 3' arm of the hairpin structure by mutant Taq polymerases lacking synthetic activity yields a single species of labeled cleaved product, while wild type Taq polymerase produces multiple cleavage products and converts the hairpin structure to a double stranded form in the presence of dNTPs, due to the high level of synthetic activity of the wild type Taq enzyme.

U.S. Pat. Nos. 5,843,669, 5,719,028, 5,837,450, 5,846,717 and 5,888,780 also disclose that mutant Taq polymerases exhibiting reduced synthetic activity, but not wild type Taq polymerase, can release a single labeled fragment by cleaving a linear nucleic acid substrate comprising a 5' end labeled target nucleic acid and a complementary oligonucleotide wherein the complementary oligonucleotide hybridizes to a portion of the target nucleic acid such that 5' and 3' regions of the target nucleic acid are not annealed to the oligonucleotide and remain single stranded.

There is a need in the art for a method of generating a signal that does not require formation of a cleavage structure and does not require an additional cleavage step.

Methods of detecting and/or measuring a nucleic acid in the absence of a cleavage step are known in the art.

U.S. Pat. Nos. 6,103,476 and 5,595,517 teach unimolecular and bimolecular hybridization probes for the detection of nucleic acid target sequences, comprising a target complement sequence, and an affinity pair holding the probe in a closed conformation in the absence of target sequence. According to the method of the invention of these patents, a probe comprises either a label pair that interacts when the probe is in the closed conformation or, for certain unimolecular probes, a non-interactive label.

U.S. Pat. Nos. 6,103,476 and 5,595,517 teach generation of a signal as a result of hybridization of the probe and target sequences and a conformational change in the probe such that the probe shifts to an open conformation. The conformational change in the probe that occurs as a result of hybridization, is detectable due to reduced interaction of the label pair or by detecting a signal from a non-interactive label.

U.S. Pat. No. 6,150,097 relates to nucleic acid hybridization probes (bimolecular, according to one embodiment) that are labeled with a non-FRET pair of chromophores and undergo a conformational change as a result of interacting with a target. This patent teaches generation of a signal as a result of hybridization of the probe and target and a conformational change in the probe that alters the distance between the label pair. The conformational change in the probe that occurs as a result of hybridization, is detectable due to increased or reduced interaction of the label pair.

None of these patents teach generation of a signal as a result of hybridization of the probe to the target and subsequent dissociation of at least one subunit of the probe. Furthermore, none of these patents teach generation of a signal as a result of hybridization of the probe to the target, displacement of at least one subunit of the probe by the synthetic activity of a polymerase and subsequent dissociation of at least one subunit of the probe.

There is a need in the art for a method of generating a signal wherein the generated signal is released from a target nucleic acid and can be measured in the absence of the target nucleic acid. A method of generating a signal wherein the signal is released from the target nucleic acid offers the advantage of an increased signal. For example, by completely separating two members of an interactive label pair by dissociating two subunits of a probe, each of which individually comprises one member of the interactive label pair, the intensity of the signal is increased and the background is decreased.

There is also a need in the art for a simplified method of generating a signal that does not require multiple steps, including a cleavage step.

There is a need in the art for a method of generating a signal that utilizes a probe having at least two subunits and comprising secondary structure wherein some or all of the self-complementary regions of the probe that anneal to form the secondary structure are melted when the probe hybridizes with a target nucleic acid, thereby reducing non-specific binding of the probe to the target, and increasing the specificity of the assay.

U.S. Pat. Nos. 5,843,669, 5,719,028, 5,837,450, 5,846,717 and 5,888,780 also disclose a method of cleaving a labeled nucleic acid substrate at naturally occurring areas of secondary structure. According to this method, biotin labeled DNA substrates are prepared by PCR, mixed with wild type Taq polymerase or CleavaseBN (a mutant Taq polymerase with reduced synthetic activity and wild type 5' to 3' nuclease activity), incubated at 95° C. for 5 seconds to denature the substrate and then quickly cooled to 65° C. to allow the DNA to assume its unique secondary structure by allowing the formation of intra-strand hydrogen bonds between the complementary bases. The reaction mixture is incubated at 65° C. to allow cleavage to occur and biotinylated cleavage products are detected.

The polymerase chain reaction (PCR) technique, is disclosed in U.S. Pat. Nos. 4,683,202, 4,683,195 and 4,800,159. In its simplest form, PCR is an in vitro method for the enzymatic synthesis of specific DNA sequences, using two oligonucleotide primers that hybridize to opposite strands and flank the region of interest in the target DNA. A repetitive series of reaction steps involving template denaturation, primer annealing and the extension of the annealed primers by DNA polymerase results in the exponential accumulation of a specific fragment whose termini are defined by the 5' ends of the primers. PCR is reported to be capable of producing a selective enrichment of a specific DNA sequence by a factor of $10^9$. The PCR method is also described in Saiki et al., 1985, *Science*, 230:1350.

While the PCR technique is an extremely powerful method for amplifying nucleic acid sequences, the detection of the amplified material requires additional manipulation and subsequent handling of the PCR products to determine whether the target DNA is present. It is desirable to decrease the number of subsequent handling steps currently required for the detection of amplified material. An assay system, wherein a signal is generated while the target sequence is amplified, requires fewer handling steps for the detection of amplified material, as compared to a PCR method that does not generate a signal during the amplification step.

U.S. Pat. Nos. 5,210,015 and 5,487,972 disclose a PCR based assay for releasing labeled probe comprising generating a signal during the amplification step of a PCR reaction in the presence of a nucleic acid to be amplified, Taq polymerase that has 5' to 3' exonuclease activity and a 5', 3' or 5' and 3' end-labeled probe comprising a region complementary to the amplified region and an additional non-complementary 5' tail region. U.S. Pat. Nos. 5,210,015 and 5,487,972 disclose further that this PCR based assay can liberate the 5' labeled end of a hybridized probe when the Taq polymerase is positioned near the labeled probe by an upstream probe in a polymerization independent manner, e.g. in the absence of dNTPs.

There is a need in the art for a method of detecting or measuring a target nucleic acid sequence that does not require multiple steps.

There is also a need in the art for a PCR process for detecting or measuring a target nucleic acid sequence that does not require multiple steps subsequent to the amplification process.

There is also a need in the art for a PCR process for detecting or measuring a target nucleic acid sequence that allows for concurrent amplification and detection of a target nucleic acid sequence in a sample.

There is also a need in the art for a PCR process for detecting or measuring a target nucleic acid sample that does not require a cleavage step.

SUMMARY OF THE INVENTION

The invention provides a method of generating a signal indicative of the presence of a target nucleic acid sequence in a sample, comprising the following steps. A detection complex is formed by incubating a sample comprising a target nucleic acid sequence and a probe, wherein the probe comprises a first and a second subunit. The probe is bound to the target nucleic acid such that the first subunit of the probe dissociates from the second subunit of the probe. Binding of the target nucleic acid sequence and the probe is performed at a binding temperature. The first subunit of the probe dissociates from the second subunit of the probe thereby releasing the first subunit of the probe to generate a signal. The first subunit of the probe does not dissociate from the second subunit of the probe when not bound to the target nucleic acid sequence at or below the binding temperature. Generation of the signal is indicative of the presence of a target nucleic acid sequence in the sample.

As used herein, a "probe" refers to at least two single stranded nucleic acid subunits wherein at least one subunit comprises a region or regions that are complementary to a target nucleic acid sequence (e.g., target nucleic acid binding sequences, for example B' and C1 in FIGS. 1*a* and *b*). A "probe according to the invention encompasses a multisubunit probe comprising two or more (i.e., 3, 4, 5, 10 etc. . . . ) single stranded nucleic acid subunits. The subunits of a probe "associate" or "bind" to each other in the absence of a target nucleic acid, at or below a "binding temperature", with a binding constant sufficiently strong to prevent dissociation of a subunit of the probe from the remaining subunit(s) of the probe. According to one embodiment of the invention, a subunit of the probe is released upon hybridization of the probe to the target nucleic acid to generate a signal. In another embodiment of the invention, a subunit of the probe is displaced from the target nucleic acid by a primer extension product and is released from the remaining subunit(s) of the probe upon binding of the probe to the target nucleic acid and extension of an upstream primer by a nucleic acid polymerization activity. A binding constant that is sufficiently strong to prevent dissociation of a subunit of the probe will also, therefore prevent generation of a signal as measured by a detection assay according to the invention (i.e., as described in Examples 2 and 3). The subunits of a probe associate with each other with a dissociation constant ($K_D$) of at most about $1\times10^{-1}$ M, usually at most $1\times10^{-4}$ M, typically at most $1\times10^{-5}$ M, preferably at most $1\times10^{-6}$ M to $1\times10^{-7}$ M or lower. Preferably, the subunits of a probe associate with each other such that under conditions used to bind to a target nucleic acid, at least 80%, and preferably 90%, and more preferably at least 99% of the subunits of the probe are associated with one another.

Probes useful according to the invention include covalently bound or non-covalently bound subunits (e.g., a bi-molecular or multi-molecular probe as defined herein). A "probe" according to one embodiment of the invention has a secondary structure that changes upon binding of the probe to the target nucleic acid sequence. A "probe" according to the invention binds to a target nucleic acid sequence to form a detection complex, wherein binding is performed at a binding temperature, and the first subunit of the probe does not dissociate from the second subunit of the probe when not bound to the target nucleic acid sequence at or below the binding temperature. In one embodiment of the invention, a probe may comprise a region that cannot bind or is not complementary to a target nucleic acid sequence. A "probe" that is useful according to the invention encompasses a probe wherein at least a portion of the first subunit of the probe binds specifically to the target nucleic acid sequence. In one embodiment of the invention, a probe does not have a secondary structure when bound to a target nucleic acid.

As used herein, "at least a portion of", as it refers to a probe subunit, means less than 100%, (e.g., 99%, 90%, 75%, 50%, 25% etc. . . . ) of the nucleotides of the probe subunit.

As used herein, "secondary structure" refers to a three-dimensional conformation (for example a hairpin, a stem-loop structure, an internal loop, a bulge loop, a branched structure or a pseudoknot, FIG. 2; multiple stem loop structures, cloverleaf type structures or any three dimensional structure. As used herein, "secondary structure" includes tertiary, quaternary etc. . . . structure. A probe comprising such a three-dimensional structure binds to a target nucleic acid sequence at a binding temperature to form a detection complex. The first subunit of the probe does not dissociate from the second subunit of the probe when not bound to a target nucleic acid sequence at or below the binding temperature. The three dimensional structure of the probe when not bound to the target nucleic acid sequence is, preferably, stable at or below the binding temperature at which the probe binds to the target nucleic acid sequence. "Secondary structure" as used herein, can mean a sequence comprising a first single-stranded sequence of bases (referred to herein as a "complementary nucleic acid sequence" followed by a second complementary sequence in the same probe subunit, comprising the probe, wherein the probe subunit folds back on itself to generate an antiparallel duplex structure, wherein the single-stranded sequence and the complementary sequence (that is, the complementary nucleic acid sequences) anneal by the formation of hydrogen bonds. "Secondary structure" also refers to a first "complementary nucleic acid sequence" in a first probe subunit and a second "complementary nucleic acid sequence" in a second probe subunit, wherein the first and second complementary sequences anneal by the formation of hydrogen bonding to form a duplex structure. Oligonucleotide probes, as used in the present invention include probes and probe subunits comprising secondary structure, including, but not limited to molecular beacons, safety pins (FIG. 5), scorpions (FIG. 6), and sunrise/amplifluor probes (FIG. 7), the details and structures of which are described below and in the corresponding figures.

As used herein, first and second "complementary" nucleic acid sequences are complementary to each other and can anneal by the formation of hydrogen bonds between the complementary bases.

A secondary structure also refers to the conformation of a nucleic acid molecule comprising an affinity pair, defined herein, wherein the affinity pair reversibly associates as a result of attractive forces that exist between the pair of moieties comprising the affinity pair.

A "probe" according to the invention comprises more than one subunit or molecule (e.g., bi-molecular or multi-molecular). At least one of the molecules comprising a bi-molecular or multi-molecular probe binds to a target nucleic acid sequence to form a detection complex, wherein binding is performed at a binding temperature, and wherein the secondary structure of the molecule of the probe when not bound to the target nucleic acid sequence is, preferably, stable at or below the binding temperature. The first subunit of the probe does not dissociate from at least the second subunit of the probe when not bound to a target nucleic acid sequence at or below the binding temperature. The invention provides for a probe wherein the probe subunit that binds to the target nucleic acid is also the probe subunit that dissociates from the remaining probe subunit(s) following binding of the probe to the target nucleic acid. The invention also provides for a probe wherein the probe subunit that binds to the target nucleic acid is not the probe subunit that dissociates from the remaining probe subunit(s) following binding of the probe to the target nucleic acid. The molecules comprising the multimolecular probe associate with each other via intermolecular bonds (e.g., hydrogen bonds or covalent bonds). For example, a heterologous loop (see FIG. 2), or a cloverleaf structure wherein one or more loops of the cloverleaf structure comprises a distinct molecule, and wherein the molecules that associate to form the cloverleaf structure associate via intermolecular bonding (e.g., hydrogen bonding or covalent bonding), are examples of multimolecular probes useful according to the invention.

As used herein, a "molecule" or a "subunit" of a probe refers to a polynucleotide, and includes a polynucleotide further comprising an attached member or members of an affinity pair.

A "subunit" or a "molecule" comprising a probe is 10,000 nucleotides in length, ideally from 6–5000, 7–1000, 8–500, 9–250, 10–100 and 17–40 nucleotides in length, although probes or a molecule comprising a probe of different lengths are useful.

In one embodiment, a "molecule" or a "subunit" of a probe according to the invention has a target nucleic acid binding sequence that is from about 5 to about 10,000 nucleotides, and preferably from 10 to about 140 nucleotides. In one embodiment, a "molecule" or a "subunit" of a probe according to the invention comprises at least first and second complementary nucleic acid sequences or regions that are 3–250, preferably 4–150, more preferably 5–110 and most preferably 6–50 nucleotides long. The first and second complementary nucleic acid sequences may have the same length or may be of different lengths. The invention provides for a subunit of a probe wherein the first and second complementary nucleic acid sequences are both located upstream (5') of the target nucleic acid binding site. Alternatively, the first and second complementary nucleic acid sequences can both be located downstream (3') of the target nucleic acid binding site. In another embodiment, the invention provides for a subunit of a probe wherein the first complementary nucleic acid sequence is upstream (5') of the target nucleic acid binding site and the second complementary nucleic acid sequence is downstream (3') of the target nucleic acid binding site. In another embodiment, the invention provides for a probe subunit wherein the second complementary nucleic acid sequence is upstream (5') of the target nucleic acid binding site and the first complementary nucleic acid sequence is downstream (3') of the target nucleic acid binding site. The invention also provides for probes wherein a first complementary nucleic acid sequence is on a first probe subunit and a second complementary nucleic acid sequence is on a second probe subunit. The actual length of the complementary nucleic acid binding site will be chosen with reference to the target nucleic acid binding sequence such that the first subunit of the probe does not dissociate from at least the second subunit of the probe when not bound to the target nucleic acid sequence at or below the binding temperature. The actual length will also be chosen with reference to the target nucleic acid binding sequence such that the secondary structure of the probe is, preferably, stable when the probe is not bound to the target nucleic acid at or below the temperature at which binding of the probe to the target nucleic acid is performed. As the target nucleic acid binding sequence increases in size up to 500 nucleotides, the length of the complementary nucleic acid sequences may increase up to 15–125 nucleotides. For a target nucleic acid binding sequence greater than 100 nucleotides, the length of the complementary nucleic acid sequences need not be increased further. If the probe is also an allele-discriminating probe, the lengths of the complementary nucleic acid sequences are more restricted, as is discussed below.

As used herein, the "target nucleic acid binding sequence" refers to the region of a subunit of a probe that binds specifically to the target nucleic acid. The invention also provides for a "target nucleic acid binding sequence" comprising the combination of a region of a first subunit of a probe and a region of a second subunit of a probe. In certain embodiments, a "target nucleic acid binding sequence" comprises the combination of a region of two or more subunits of a probe. According to these embodiments of the invention, the individual region of each subunit that comprises the target nucleic acid binding sequence can bind to either contiguous locations on the target nucleic acid binding sequence or can bind to non-contiguous or scattered regions of the target nucleic acid. As used herein, a "region" refers to a sequence of at least 5 to about 10,000 nucleotides in length, preferably 6 nucleotides, 8 nucleotides, 10 nucleotides, 12 nucleotides, 14 nucleotides, 16 nucleotides, 20 nucleotides, 30 nucleotides, 50 nucleotides, 75 nucleotides, 100 nucleotides, 150 nucleotides, 200 nucleotides or more.

A "hairpin structure" or a "stem" refers to a double-helical region formed by base pairing between adjacent, inverted, complementary sequences in a single strand of RNA or DNA.

A "stem-loop" structure refers to a hairpin structure, further comprising a loop of unpaired bases at one end.

As used herein, a probe with "stable" secondary structure when not bound to a target nucleic acid sequence, refers to a secondary structure wherein 50% or more (e.g., 50%, 55%, 75% or 100%) of the base pairs that constitute the probe or a probe subunit are not dissociated under conditions which permit hybridization of the probe to the target nucleic acid, but in the absence of the target nucleic acid. "Stability" of a nucleic acid duplex is determined by the melting temperature, or "$T_m$". The $T_m$ of a particular nucleic acid duplex under specified conditions (e.g., salt concentration and/or the presence or absence of organic solvents) is the temperature at which half (50%) of the base pairs of the duplex molecule have disassociated (that is, are not hybridized to each other in a base-pair).

The "stability" of the secondary structure of a probe when not bound to the target nucleic acid is defined in a melting temperature assay, in a fluorescence resonance energy transfer (FRET) assay or in a fluorescence quenching assay, (the details or which are described in a section entitled, "Determining the Stability of the Secondary Structure of a Probe").

A probe useful in the invention preferably will have secondary structure that is "stable", when not bound to a target, at or below the temperature of the binding reaction. Thus, the temperature at which binding of a probe to a target nucleic acid is performed according to the invention, must be lower than the Tm of the secondary structure. The secondary structure of the probe is "stable" in a melting temperature assay, at a temperature that is at or below the temperature of the binding reaction (i.e., at which binding is performed) if the level of light absorbance at the temperature at or below the temperature of the binding reaction is less than (i.e., at least 5% less than, preferably 20% less than and most preferably 25% less than, etc. . . . ) than the level of light absorbance at a temperature that is equal to or greater than the Tm of the probe.

According to the method of the invention, the stability of a secondary structure can be measured by a FRET assay or a fluorescence quenching assay (described in the section entitled, "Determining the Stability of the Secondary Structure of a Probe"). As used herein, a fluorescence quenching assay can include a FRET assay. A probe according to the invention is labeled with an appropriate pair of interactive labels (e.g., a FRET pair (for example as described in the section entitled, "Determining the Stability of the Secondary Structure of the Probe", below)) that can interact over a distance of, for example 2 nucleotides, or a non-FRET-pair, (e.g., tetramethylrhodamine and DABCYL) that can interact over a distance of, for example, 20 nucleotides. For example, a probe according to the invention may be labeled with a fluorophore and a quencher and fluorescence is then measured, in the absence of a target nucleic acid, at different temperatures. The Tm is the temperature at which the level of fluorescence is 50% of the maximal level of fluorescence observed for a particular probe, see FIG. 8e. The Tm for a particular probe wherein the nucleic acid sequence of the probe is known, can be predicted according to methods known in the art. Thus, fluorescence is measured over a range of temperatures, e.g., wherein the lower temperature limit of the range is at least 50° Celsius below, and the upper temperature limit of the range is at least 50° Celsius above the Tm or predicted Tm, for a probe according to the invention.

A secondary structure is herein defined as "stable" in a FRET assay at a temperature that is at or below the binding temperature (i.e., at which a probe binds to a target nucleic acid) if the level or wavelength of fluorescence is increased or decreased (e.g., at least 5% less than, preferably 20% less than and more preferably 25% less than, etc. . . . ) as compared with the level or wavelength of FRET that is observed at the Tm of the probe (see FIGS. 8e and f). For example, an increase or a decrease in FRET can occur in a FRET assay according to the invention. In another embodiment, a shift in wavelength, which results in an increase in the new, shifted wavelength or, a decrease in the new shifted wavelength, can occur in a FRET assay according to the invention.

A "change" in a secondary structure, according to the invention can be measured in a fluorescence quenching assay wherein a probe according to the invention comprises a fluorophore and a quencher that are positioned such that in the absence of a target nucleic acid, and at temperatures below the Tm of the probe there is quenching of the fluorescence (as described above). As used herein, a "change" in secondary structure that occurs when a probe according to the invention binds to a target nucleic acid, refers to an increase in fluorescence in such an assay, such that the level of fluorescence after binding of the probe to the target nucleic acid at a temperature below the Tm of the probe, is greater than (e.g., at least 5%, preferably 5–20% and most preferably 25% or more) the level of fluorescence observed in the absence of a target nucleic acid sequence (see FIG. 8g).

A secondary structure, according to the invention, can be detected by subjecting a probe comprising a fluorophore and a quencher to a fluorescence quenching assay (as described above). A probe that exhibits a change in fluorescence that correlates with a change in temperature, see FIG. 8e, (e.g., fluorescence increases as the temperature of the FRET reaction is increased) may be capable of forming a secondary structure.

As used herein, a "binding temperature" that is useful according to the invention is selected such that a first subunit of a probe will not dissociate from at least a second subunit of a probe when the probe is not bound to the target nucleic acid at or below the binding temperature. As used herein, a "binding temperature" that is useful according to the invention is also a temperature that is less than (at least 5° and preferably 10° C.) the $T_m$ of a probe having a secondary structure. A "binding temperature" is selected so that the three-dimensional structure of the probe, when not bound to the target nucleic acid sequence is, preferably, stable at or below the binding temperature.

Preferably the 3' terminus of a subunit(s) of the probe that hybridizes to a target nucleic acid will be "blocked" to prohibit incorporation of the probe into a primer extension product if an active polymerase is used in the reaction. "Blocking" can be achieved by using non-complementary bases or by adding a chemical moiety such as biotin or a phosphate group to the 3' hydroxl of the last nucleotide. Blocking can also be achieved by removing the 3'-OH or by using a nucleotide that lacks a 3'-OH such as dideoxynucleotide.

The term probe encompasses an allele-discriminating probe. As used herein, an "allele-discriminating" probe preferentially hybridizes to perfectly complementary target nucleic acid sequences and discriminates against sequences that vary by at least one nucleotide. A nucleic acid sequence which differs by at least one nucleotide, as compared to a target nucleic acid sequence, hereafter referred to as a "target-like nucleic acid sequence", is thus not a target nucleic acid sequence for an allele-discriminating probe according to the invention.

Allele-discriminating probes do not hybridize sufficiently to a target-like nucleic acid sequence that contains one or more nucleotide mismatches as compared to the target nucleic acid complementary sequence at a particular temperature or within a range of temperatures determined by experimental optimization to permit an allele discriminating probe to discriminate between a target and a target-like sequence with at least a single nucleotide difference, and thus do not undergo a change in secondary structure upon binding to a target-like nucleic acid sequence in the presence of only a target-like nucleic acid sequence, and under conditions that would support hybridization of the allele discriminating probe to a target nucleic acid sequence.

In one embodiment, an "allele-discriminating probe" according to the invention refers to a probe that hybridizes to a target-like nucleic acid sequence that varies by at least one nucleotide from the target nucleic acid sequence, wherein the variant nucleotide(s) is/are not located in the allele-discriminating site. According to this embodiment of the invention, "an allele-discriminating probe" cannot bind to a target-like nucleic acid sequence that also varies by at least one nucleotide in the allele-discriminating site at a particular temperature or within a range of temperatures determined by experimental optimization to permit an allele discriminating probe to discriminate between a target and a target-like sequence with at least a single nucleotide difference. Single nucleotide differences only affect the percentage of a probe that is bound to a target or target-like nucleic acid sequence. For example, the invention provides for a perfectly matched probe, wherein as much as 100% of the target is in a probe-target complex (e.g., is bound by probe), in the presence of excess probe. The invention also provides for probes comprising at least a single base mismatch wherein at least 1–5% and preferably 5–10% of the target-like sequence is bound by the probe under the same conditions used to form a complex comprising a target sequence and a perfectly matched probe.

As used herein, "allele-discriminating site" refers to a region of a target nucleic acid sequence that is different (i.e., by at least one nucleotide) from the corresponding region in all possible alleles comprising the target nucleic acid sequence.

Allele-discriminating probes useful according to the invention also include probes that bind less effectively to a target-like sequence, as compared to a target sequence. The effectiveness of binding of a probe to a target sequence or a target-like sequence can be measured in a FRET assay, performed at a temperature that is below (at least 1° and preferably 10° C. or more) the Tm of the secondary structure of the probe, in the presence of a target-like sequence or a target sequence. The change in the level of fluorescence in the presence or absence of a target sequence compared to the change in the level of fluorescence in the presence or absence of a target-like sequence, provides an effective measure of the effectiveness of binding of a probe to a target or target-like sequence.

In a method according to the invention, a probe that binds less effectively to a target-like sequence as compared to a target sequence would undergo a smaller (e.g., preferably 25–50%, more preferably 50–75% and most preferably 75–90% of the value of the change in fluorescence upon binding to a target nucleic acid sequence) change in secondary structure, as determined by measuring fluorescence in a FRET or fluorescence quenching assay as described herein, upon hybridization to a target-like sequence as compared to a target nucleic acid sequence. In a method according to the invention, a probe that binds less effectively to a target-like sequence as compared to a target sequence would generate a signal that is indicative of the presence of a target-like nucleic acid sequence in a sample. However, the intensity of the signal would be altered (e.g., preferably 25–50%, more preferably 50–75% and most preferably 75–90% less than or more than the value of the change in fluorescence upon binding to a target nucleic acid sequence) compared to the intensity of a signal generated in the presence of a target sequence, as described hereinabove for a smaller change.

A "signal that is indicative of the presence of a "target nucleic acid sequence" or a "target-like nucleic acid sequence" refers to a signal that is equal to a signal generated from 1 molecule to $10^{20}$ molecules, more preferably about 100 molecules to $10^{17}$ molecules and most preferably about 1000 molecules to $10^{14}$ molecules of a target nucleic acid sequence or a target-like nucleic acid sequence.

As used herein, "label" or "labeled moiety capable of providing a signal" refers to any atom or molecule which can be used to provide a detectable (preferably quantifiable) signal, and which can be operatively linked to a nucleic acid. Labels may provide signals detectable by fluorescence, radioactivity, colorimetry, gravimetry, X-ray diffraction or absorption, magnetism, enzymatic activity, mass spectrometry, binding affinity, hybridization radiofrequency, nanocrystals and the like. A labeled probe according to the methods of the invention is labeled at the 5' end or the 3' end of at least one subunit of the probe. Alternatively, at least one subunit of the probe is labeled internally. The label can be "direct", i.e. a dye, or "indirect". i.e. biotin, digoxin, alkaline phosphatase (AP), horse radish peroxidase (HRP) etc. . . . For detection of "indirect labels" it is necessary to add additional components such as labeled antibodies, or enzyme substrates to visualize the captured, released, labeled probe subunit.

As used herein, "affinity pair" refers to a pair of moieties (for example complementary nucleic acid sequences, protein-ligand, antibody-antigen, protein subunits, and nucleic acid binding proteins-binding sites) that can reversibly associate as a result of attractive forces that exist between the moieties.

In embodiments wherein the affinity pair comprises complementary nucleic acid regions that reversibly interact with one another, the lengths of the target nucleic acid binding sequences, and the nucleic acid sequences comprising the affinity pair, are chosen for the proper thermodynamic functioning of the probe under the conditions of the projected hybridization assay. Persons skilled in hybridization assays will understand that pertinent conditions include probe, target and solute concentrations, binding temperature, the presence of denaturants and volume excluders, and other hybridization-influencing factors. The length of a target nucleic acid binding sequence can range from 7 to about 10,000 nucleotides, preferably from 8–5000, 9–500, 9–250 and most preferably 10 to about 140 nucleotides. If the probe is also an allele-discriminating probe, the length is more restricted, as is discussed below.

In embodiments wherein the affinity pair comprises complementary nucleic acid regions that reversibly interact with one another, and cannot hybridize or are not complementary to a target nucleic acid sequence, the complementary nucleic acid region sequences of the affinity pair should be of sufficient length that under the conditions of the assay and at the binding temperature, when the probe is not bound to a target, the complementary nucleic acid sequences are associated.

Depending upon the assay conditions used, complementary nucleic acid sequences of 3–25 nucleotide lengths can perform this function. An intermediate range of 4–15, and more preferably 5–11, nucleotides is often appropriate. The actual length will be chosen with reference to the target nucleic acid binding sequence such that the first subunit of the probe does not dissociate from at least the second subunit of the probe when not bound to the target nucleic acid sequence at or below the binding temperature. The actual length will also be chosen with reference to the target nucleic acid binding sequence such that the secondary structure of the probe is, preferably, stable when not bound to the target nucleic acid at or below the temperature at which binding of the probe to a target nucleic acid is performed. As the target nucleic acid binding sequence increases in size up to 100 nucleotides, the length of the complementary nucleic acid sequences may increase up to 15–25 nucleotides. For a target nucleic acid binding sequence greater than 100 nucleotides, the length of the complementary nucleic acid sequences are not increased further. If the probe is also an allele-discriminating probe, the lengths of the complementary nucleic acid sequences are more restricted, as is discussed below.

Allele-discriminating probes that do not hybridize sufficiently to a target-like nucleic acid sequence that contains one or more nucleotide mismatches as compared to the target nucleic acid complementary sequence, must be designed such that, under the assay conditions used, reduction or elimination of secondary structure in the probe and hybridization with a target nucleic acid sequence will occur efficiently only when the target nucleic acid complementary sequence finds a perfectly complementary target sequence under certain reaction conditions. Certain reaction conditions may include, for example, a particular temperature or a range of temperatures determined by experimental optimization to permit an allele discriminating probe to discriminate between a target and a target-like sequence with at least a single nucleotide difference.

In one embodiment, an "allele-discriminating probe" according to the invention refers to a probe that hybridizes to a target-like nucleic acid sequence that varies by at least one nucleotide from the target nucleic acid sequence, wherein the variant nucleotide(s) is/are not located in the allele-discriminating site. According to this embodiment of the invention, "an allele-discriminating probe" cannot bind efficiently to a target-like nucleic acid sequence that also varies by at least one nucleotide in the allele-discriminating site under certain reaction conditions. Certain reaction conditions may include, for example, a particular temperature or a range of temperatures determined by experimental optimization to permit an allele discriminating probe to discriminate between a target and a target-like sequence with at least a single nucleotide difference.

In one embodiment of the invention, an allele discriminating probe according to the invention preferably comprises a target nucleic acid binding sequence from 6 to 50 and preferably from 7 to 25 nucleotides, and sequences of the complementary nucleic acid sequences from 3 to 8 nucleotides. The guanosine-cytidine content of the secondary structure and probe-target hybrids, salt, and assay temperature should all be considered, for example magnesium salts have a strong stabilizing effect that is particularly important to consider when designing short, allele-discriminating probes.

If an allele-discriminating probe is to have a target nucleic acid binding sequence near the upper limits of about 50 nucleotides long, the sequence should be designed such that a single nucleotide mismatch to be discriminated against occurs at or near the middle of the target nucleic acid complementary sequence. For example, probes comprising a sequence that is 21 nucleotides long should preferably be designed so that the mismatch occurs opposite one of the 14 most centrally located nucleotides of the target nucleic acid complementary sequence and most preferably opposite one of the 7 most centrally located nucleotides. Designing a probe so that the mismatch to be discriminated against occurs in or near the middle of the target nucleic acid binding sequence/target-like nucleic acid binding sequence is believed to improve the performance of an allele-discriminating probe.

As used herein, a "detection complex" refers to a structure (for example as illustrated in FIG. 1) comprising a target nucleic acid sequence bound to a probe comprising at least two subunits such that a subunit of the probe dissociates from the complex.

As used herein, a "detection complex" also refers to a structure (for example as illustrated in FIG. 1) comprising a target nucleic acid sequence bound to a probe comprising at least two subunits and having a secondary structure that changes upon binding of the probe to the target nucleic acid sequence such that a subunit of the probe dissociates from the complex.

In another embodiment, a "detection complex" refers to a structure (for example as illustrated in FIG. 1) comprising a target nucleic acid sequence bound to an upstream primer and a downstream probe, wherein the probe comprises comprises at least two subunits such that a subunit of the probe dissociates from the complex.

In another embodiment, a "detection complex" refers to a structure (for example as illustrated in FIG. 1) comprising a target nucleic acid sequence bound to an upstream primer and a downstream probe, wherein the probe comprises at least two subunits and has a secondary structure that changes upon binding of the probe to the target nucleic acid sequence such that a subunit of the probe dissociates from the complex.

Following dissociation of a probe subunit from the "detection complex" the target nucleic acid sequence associates with the remaining, undissociated probe subunit(s) such that more than half of the undissociated probe subunits remain bound to the target nucleic acid sequence. According to one embodiment of the invention, a subunit of the probe is released upon hybridization of the probe to the target nucleic acid to generate a signal. In another embodiment of the invention, a subunit of the probe is displaced from the target nucleic acid by a primer extension product and is released from the remaining subunit(s) of the probe upon binding of the probe to the target nucleic acid and extension of an upstream primer by a nucleic acid polymerization activity. A binding constant that is sufficiently strong to prevent dissociation of a subunit of the probe will also, therefore prevent generation of a signal as measured by a detection assay according to the invention (i.e., as described in Examples 2 and 3) that is greater than 5%, preferably greater than 3% and most preferably greater than 1% of the amount of signal generated upon dissociation of a probe subunit, wherein a signal is detected in a detection assay according to the invention (i.e., Examples 2 and 3)

Following dissociation of a probe subunit from the "detection complex" the target nucleic acid sequence associates with the remaining, undissociated probe subunit(s) such that more than half of the undissociated probe subunits remain bound to the target nucleic acid sequence, under suitable conditions.

In another embodiment, a "detection complex" refers to a structure (for example as illustrated in FIG. 1) comprising a target nucleic acid sequence bound to an upstream primer and a downstream probe, wherein the probe comprises at least two subunits and has a secondary structure that changes upon binding of the probe to the target nucleic acid sequence, wherein the activity of a nucleic acid polymerase extends the upstream primer, and the upstream primer displaces a subunit of the probe from the target nucleic acid such that a subunit of the probe dissociates from the complex.

At a binding temperature temperature as defined herein and under conditions that permit selective hybridization (defined hereinbelow), binding of a target nucleic acid sequence to a probe results in the formation of a detection complex with a $K_D$ of at most $1 \times 10^{-1}$ M, usually at most $1 \times 10^{-4}$ M, typically, at most, $1 \times 10^{-5}$ M, preferably at most $1 \times 10^{-6}$ M to $1 \times 10^{-7}$ M. At a polymerization temperature, as defined herein, under conditions that permit selective hybridization and prior to displacement of a probe subunit by the extension product of the upstream primer, binding of target nucleic acid sequence to a probe results in the formation of a detection complex with a $K_D$ of at least $1 \times 10^{-3}$ M, preferably $1 \times 10^{-4}$ M and more preferably $1 \times 10^{-5}$ M. The $K_D$ of this complex is sufficiently strong to prevent dissociation of a subunit of the probe from the remaining subunit(s) of the probe, to generate a signal. According to one embodiment of the invention, a subunit of the probe is released upon hybridization of the probe to the target nucleic acid to generate a signal. In another embodiment of the invention, a subunit of the probe is displaced from the target nucleic acid by a primer extension product and is released from the remaining subunit(s) of the probe upon binding of the probe to the target nucleic acid and extension of an upstream primer by a nucleic acid polymerization activity. A binding constant that is sufficiently strong to prevent dissociation of a subunit of the probe will also, therefore prevent generation of a signal as measured by a detection assay according to the invention (i.e., as described in Examples 2 and 3) that is greater than 5%, preferably greater than 3% and most preferably greater than 1% of the amount of signal generated upon dissociation of a probe subunit, wherein a signal is detected in a detection assay according to the invention (i.e., Examples 2 and 3)

Following dissociation of a probe subunit from the "detection complex" the target nucleic acid sequence associates with the remaining, undissociated probe subunit(s) such that more than half of the undissociated probe subunits remain bound to the target nucleic acid sequence, under suitable conditions.

As used herein, the terms "binding to" or "hybridizing to" or "hybridization" refer to hydrogen binding with a complementary nucleic acid, via an interaction between for example, a target nucleic acid sequence and any one of a probe, a probe subunit, at least a portion of one or more probe subunits or a primer.

Typically, selective hybridization occurs when two nucleic acid sequences are substantially complementary (at least about 65% complementary over a stretch of at least 14 to 25 nucleotides, preferably at least about 75%, more preferably at least about 90% complementary). See Kanehisa, M., 1984, Nucleic Acids Res. 12: 203, incorporated herein by reference. As a result, it is expected that a certain degree of mismatch is tolerated. Such mismatch may be small, such as a mono-, di- or tri-nucleotide. Alternatively, a region of mismatch may encompass loops, which are defined as regions in which there exists a mismatch in an uninterrupted series of four or more nucleotides.

Numerous factors influence the efficiency and selectivity of hybridization of two nucleic acids, for example a target nucleic acid sequence to a probe. These factors include probe length, nucleotide sequence and/or composition, hybridization temperature, buffer composition and potential for steric hindrance in the region to which the probe is required to hybridize.

A positive correlation exists between the nucleic acid sequence (i.e. a probe, probe subunit or primer) length and both the efficiency and accuracy with which a nucleic acid sequence will anneal to a target sequence. In particular, longer sequences have a higher melting temperature ($T_M$) than do shorter ones, and are less likely to be repeated within a given target sequence, thereby minimizing promiscuous hybridization. Hybridization temperature varies inversely with nucleic acid sequence annealing efficiency, as does the concentration of organic solvents, e.g., formamide, that might be included in a hybridization mixture, while increases in salt concentration facilitate binding. Under stringent annealing conditions, longer nucleic acids, hybridize more efficiently than do shorter ones, which are sufficient under more permissive conditions. As herein used, the term "standard stringent conditions" means hybridization will occur only if there is at least 95% and preferably at least 97% identity between the sequences, wherein the region of identity comprises at least 10 nucleotides. In one embodiment, the sequences hybridize under stringent conditions following incubation of the sequences overnight at 42° C., followed by stringent washes (0.2×SSC at 65° C.). As several factors affect the stringency of hybridization, the combination of parameters is more important than the absolute measure of a single factor.

A "detection complex" according to one embodiment of the invention is formed by hybridizing a target nucleic acid sequence with a probe, wherein the probe comprises at least two subunits and wherein a subunit of the probe dissociates from the remaining subunit(s) of the probe upon binding of the probe to the target nucleic acid sequence.

A "detection complex" according to another embodiment of the invention is formed by hybridizing a target nucleic acid sequence with a probe, wherein the probe comprises at least two subunits, has a secondary structure that changes upon binding of the probe to the target nucleic acid sequence and wherein a subunit of the probe dissociates from the remaining subunit(s) of the probe upon binding of the probe to the target nucleic acid sequence.

A "detection complex" according to another embodiment of the invention is formed by hybridizing a target nucleic acid sequence to an upstream primer and a downstream probe, wherein the probe comprises at least two subunits and wherein a subunit of the probe dissociates from the remaining subunit(s) of the probe upon binding of the probe to the target nucleic acid sequence.

A "detection complex" according to another embodiment of the invention is formed by hybridizing a target nucleic acid sequence to an upstream primer and a downstream probe, wherein the probe comprises at least two subunits, has a secondary structure that changes upon binding of the probe to the target nucleic acid sequence and wherein a subunit of the probe dissociates from the remaining subunit(s) of the probe upon binding of the probe to the target nucleic acid sequence.

In one preferred embodiment of the invention a "detection complex" is labeled. A labeled detection complex according to one embodiment of the invention is formed by incubating a) a labeled probe comprising two subunits, and b) an appropriate target nucleic acid sequence wherein the target sequence is complementary to the labeled probe, a subunit of the labeled probe or at least a portion of a subunit of a labeled probe and c) a suitable buffer, under conditions that allow the target nucleic acid sequence to hybridize to the probe.

In another embodiment of the invention, a labeled detection complex is formed by 1. incubating a) an upstream primer, b) a labeled probe comprising a first and a second subunit, preferably located not more than 5000 and more preferably located not more than 500 nucleotides downstream of the upstream primer and c) an appropriate target nucleic acid sequence wherein the target sequence is complementary to both the primer and the labeled probe and d) a suitable buffer, under conditions that allow the target nucleic acid sequence to hybridize to the probe and the primer, and 2. extending the 3' end of the upstream primer by the synthetic activity of a polymerase such that the newly synthesized 3' end of the upstream primer partially displaces at least a portion of the probe.

According to this method of the invention, buffers and extension temperatures are favorable for strand displacement by a particular nucleic acid polymerase, according to the invention. Preferably, the subunit(s) of the probe that is bound to the target nucleic acid sequence is blocked at the 3' terminus to prevent extension of the 3' end of the probe subunit(s). In one embodiment, the upstream primer and the probe hybridize to non-overlapping regions of the target nucleic acid.

A label cannot provide a detectable signal unless a first subunit of the probe has dissociated from at least a second subunit of the probe.

As used herein, "generating a signal" refers to detecting and or measuring a released subunit of a probe that is released from the detection complex, as an indication of the presence of a target nucleic acid sequence in a sample.

In one embodiment, a signal is generated upon release of the first subunit of the probe from the second subunit of the probe. The release of the first subunit of the probe from the second subunit of the probe results from dissociation of the probe subunits. The invention also provides for a signal that is generated upon release or more than one (i.e., 2, 3, 4, 5, 10 or more) subunit of a probe from at least one additional subunit.

As used herein, "association" refers to an interaction that occurs as a result of attractive forces that exist, for example between two subunits of a probe, or between a probe or probe subunit and a target nucleic acid sequence.

As used herein, "associates" refers to probe subunits having a binding constant sufficiently strong to prevent dissociation of a subunit of the probe from the remaining subunit(s) of the probe, to generate a signal. According to one embodiment of the invention, a subunit of the probe is released upon hybridization of the probe to the target nucleic acid to generate a signal. In another embodiment of the invention, a subunit of the probe is displaced from the target nucleic acid by a primer extension product and is released from the remaining subunit(s) of the probe upon binding of the probe to the target nucleic acid and extension of an upstream primer by a nucleic acid polymerization activity. A binding constant that is sufficiently strong to prevent dissociation of a subunit of the probe will also, therefore prevent generation of a signal as measured by a detection assay according to the invention (i.e., as described in Examples 2 and 3) that is greater than 5%, preferably greater than 3% and most preferably greater than 1% of the amount of a signal generated upon dissociation of a probe subunit, as measured by a detection assay according to the invention (i.e., as described in Examples 2 and 3). The subunits of a probe associate with each other with a dissociation constant ($K_D$) of at least about $1\times10^{-3}$ M, usually at least $1\times10^{-4}$ M, typically at least $1\times10^{-5}$ M, preferably at least 33 $10^{-6}$ M to $1\times10^{-7}$ M or lower.

"Associates" also refers to a target nucleic acid sequence and a probe that forms a detection complex at a binding temperature as defined herein and under conditions that permit selective hybridization (defined hereinbelow), with a $K_D$ of at least at most about $1\times10^{-1}$ M, usually at most $1\times10^{-4}$ M, typically at most $1\times10^{-5}$ M and preferably at most $1\times10^{-6}$ M to $1\times10^{-7}$ M or lower. Preferably, the subunits of a probe associate with each other such that under conditions used to bind to a target nucleic acid, at least 80%, and preferably 90%, and more preferably 99% of the subunits of the probes are associated with one another. The $K_D$ of this complex is sufficiently strong to prevent dissociation of a subunit of the probe from the remaining subunit(s) of the probe, to generate a signal. According to one embodiment of the invention, a subunit of the probe is released upon hybridization of the probe to the target nucleic acid to generate a signal. In another embodiment of the invention, a subunit of the probe is displaced from the target nucleic acid by a primer extension product and is released from the remaining subunit(s) of the probe upon binding of the probe to the target nucleic acid and extension of an upstream primer by a nucleic acid polymerization activity. A binding constant that is sufficiently strong to prevent dissociation of a subunit of the probe will also, therefore prevent generation of a signal as measured by a detection assay according to the invention (i.e., as described in Examples 2 and 3) that is greater than 5%, preferably greater than 3% and most preferably greater than 1% of the amount of signal generated upon dissociation of a probe subunit, wherein a signal is detected in a detection assay according to the invention (i.e., Examples 2 and 3).

"Associates" also refers to a target nucleic acid sequence and the remaining, undissociated probe subunits that remain bound such that following dissociation of a probe subunit from the "detection complex", the target nucleic acid sequence associates with the remaining, undissociated probe subunit(s) such that more than half of the undissociated probe subunits remain bound to the target nucleic acid sequence under suitable conditions.

In another embodiment, a "detection complex" refers to a structure (for example as illustrated in FIG. 1) comprising a target nucleic acid sequence bound to an upstream primer and a downstream probe, wherein the probe comprises at least two subunits, wherein the activity of a nucleic acid polymerase extends the upstream primer, and the upstream primer displaces a subunit of the probe from the target nucleic acid such that the subunit of the probe dissociates from the complex.

According to this embodiment, "associates" refers to a target nucleic acid sequence and a probe that form a detection complex at a binding temperature as defined herein and under conditions that permit selective hybridization (defined hereinbelow), with a $K_D$ of at most $1 \times 10^{-1}$ M, preferably at most $1 \times 10^{-4}$ M and more preferably at most $1 \times 10^{-5}$ M. The subunits of a probe associate with each other such that under conditions used to bind to a target nucleic acid, at least 80%, and preferably 90%, and more preferably at least 99% of the subunits of the probe are associated with each other. According to this embodiment, "associates" also refers to a target nucleic acid sequence and a probe that form a detection complex at a polymerization temperature, as defined herein, under conditions that permit selective hybridization and prior to displacement of a probe subunit by the extension product of the upstream primer, binding of target nucleic acid sequence to a probe results in the formation of a detection complex with a $K_D$ of at most $1 \times 10^{-1}$ M, preferably at most $1 \times 10^{-4}$ M and more preferably at most $1 \times 10^{-5}$ M. he subunits of a probe associate with each other such that under conditions used to bind to a target nucleic acid, at least 80%, and preferably 90%, and more preferably at least 99% of the subunits of the probe are associated with each other. The $K_D$ of this complex is sufficiently strong to prevent dissociation of a subunit of the probe from the remaining subunit(s) of the probe, to generate a signal. According to one embodiment of the invention, a subunit of the probe is released upon hybridization of the probe to the target nucleic acid to generate a signal. In another embodiment of the invention, a subunit of the probe is displaced from the target nucleic acid by a primer extension product and is released from the remaining subunit(s) of the probe upon binding of the probe to the target nucleic acid and extension of an upstream primer by a nucleic acid polymerization activity. A binding constant that is sufficiently strong to prevent dissociation of a subunit of the probe will also, therefore prevent generation of a signal as measured by a detection assay according to the invention (i.e., as described in Examples 2 and 3) that is greater than 5%, preferably greater than 3% and most preferably greater than 1% of the amount of signal generated upon dissociation of a probe subunit, wherein a signal is detected in a detection assay according to the invention (i.e., Examples 2 and 3)

"Associates" also refers to a target nucleic acid sequence and the remaining, undissociated probe subunits that remain bound such that more than half of the undissociated probe subunits remain bound to the target nucleic acid sequence under suitable conditions, following displacement of a probe subunit by a primer extension product of an upstream primer and subsequent dissociation of a probe subunit from the "detection complex".

An association can be due to the occurrence of intermolecular bonds (e.g., hydrogen or covalent bonds, an electrostatic interaction or via an interaction between, for example, a protein and a ligand, an antibody and an antigen, protein subunits, or a nucleic acid binding protein and a nucleic acid binding site).

As used herein, "dissociating" or "dissociation" refers to the absence or loss of contact between two molecules, i.e., two subunits of a probe, or a target nucleic acid sequence and a probe or probe subunit, such that the binding constant is reduced by an amount which produces a discernible change in a signal compared to the bound state, including a total absence or loss of contact such that the molecules are completely separated, and thus have a dissociation constant greater than $1 \times 10^{-3}$ M. In one embodiment, "dissociation" of a subunit of a probe from the remaining probe subunit(s) occurs when a probe binds to a target nucleic acid. In another embodiment, "dissociation" according to the invention occurs when a probe binds to a target nucleic acid and undergoes a change in secondary structure. In another embodiment, "dissociation" occurs when a probe binds to a target; subsequently a subunit of the probe is displaced by a primer extension product of an upstream primer and dissociates from the remaining subunit(s) of the probe. In another embodiment, dissociation according to the invention occurs when a probe binds to a target nucleic acid and undergoes a change in secondary structure; subsequently, a subunit of the probe is displaced by a primer extension product of an upstream primer. "Dissociation" of a probe from a detection complex, as defined herein, results in the generation of a signal that is detectable by a detection assay according to the invention (i.e., Examples 2 and 3) wherein the signal is significantly greater, statistically, than the amount of signal generated by a detection complex prior to dissociation of the probe. Significantly greater refers to at least 1–2% greater than the background signal generated prior to dissociation, or more than 2-fold, 5-fold, 10-fold, 50-fold, or 1000 or more fold greater than the background signal generated prior to dissociation. For example, two subunits of a probe are dissociated if they are not hybridized or bound to each other in a base pair or via any type of intermolecular bonds (e.g., hydrogen or covalent bonds or an electrostatic interaction) and if the dissociated probe subunit is detectable when dissociated but not when part of the detection complex.

In another embodiment, a signal is generated by incubating a detection complex comprising a target nucleic acid sample, an upstream primer and a downstream probe according to the invention with a nucleic acid polymerization activity. The detection complex is incubated with a nucleic acid polymerization activity under conditions wherein the upstream primer is extended by polymerization of a nucleic acid strand. The extended upstream primer displaces the first subunit of the probe from the target nucleic acid sequence such that the first subunit of the probe dissociates from the second subunit of the probe and is released to generate a signal. According to one embodiment, the extended upstream primer displaces the first subunit of the probe from the target nucleic acid sequence such that the first subunit of the probe is partially dissociated from the second subunit of the probe. In another embodiment, the extended upstream primer displaces the first subunit of the probe from the target nucleic acid sequence such that the first subunit of the probe is not dissociated from the second subunit of the probe.

As used herein, "sample" refers to any substance containing or presumed to contain a nucleic acid of interest (a target nucleic acid sequence) or which is itself a nucleic acid containing or presumed to contain a target nucleic acid sequence of interest. The term "sample" thus includes a sample of nucleic acid (genomic DNA, cDNA, RNA), cell, organism, tissue, fluid, or substance including but not limited to, for example, plasma, serum, spinal fluid, lymph fluid, synovial fluid, urine, tears, stool, external secretions of the skin, respiratory, intestinal and genitourinary tracts, saliva, blood cells, tumors, organs, tissue, samples of in vitro cell culture constituents, natural isolates (such as drinking water, seawater, solid materials), microbial specimens, and objects or specimens that have been "marked" with nucleic acid tracer molecules.

As used herein, "target nucleic acid sequence" or "template nucleic acid sequence" refers to a region of a nucleic acid that is to be either replicated, amplified, and/or detected. In one embodiment, the "target nucleic acid sequence" or "template nucleic acid sequence" resides between two primer sequences used for amplification.

The invention also provides a method of generating a signal indicative of the presence of a target nucleic acid sequence in a sample, comprising the following steps. A detection complex is formed by incubating a sample comprising a target nucleic acid sequence, an upstream primer, and a downstream probe, wherein the downstream probe comprises a first and a second subunit. The probe and primer are bound to the target nucleic acid. The detection complex is subjected to a nucleic acid polymerization activity under conditions which permit extension of the upstream primer by polymerization of a nucleic acid strand, and displacement of the first subunit of the probe from the target nucleic acid by the nucleic acid strand. As a result of the displacement of the first subunit of the probe from the target nucleic acid, the first subunit of the probe dissociates from the second subunit of the probe and is released to generate a signal. According to this method of the invention, binding is performed at a binding temperature and the first subunit of the probe does not dissociate from the second subunit of the probe when not bound to the target nucleic acid sequence at or below the binding temperature. According to this method of the invention, polymerization is performed at a polymerization temperature. The first subunit of the probe does not dissociate from the second subunit of the probe when not displaced by the nucleic acid strand at or below the polymerization temperature. Generation of the signal is indicative of the presence of a target nucleic acid sequence in the sample.

As used herein, "primer" refers to a DNA or RNA molecule capable of hybridizing to a target nucleic acid sequence and acting as a substrate for enzymatic synthesis under conditions in which synthesis of a primer extension product which is complementary to a target nucleic acid sequence is catalyzed to produce a primer extension product which is complementary to the target nucleic acid sequence. The conditions for initiation and extension include the presence of four different deoxyribonucleoside triphosphates and a polymerization-inducing agent such as DNA polymerase or reverse transcriptase, in a suitable buffer ("buffer" includes substituents which are cofactors, or which affect pH, ionic strength, etc.) and at a suitable temperature.

The primer is preferably single-stranded for maximum efficiency in amplification. "Primers" useful in the present invention are generally between about 10 and 100 nucleotides in length, preferably between about 17 and 50 nucleotides in length, and most preferably between about 17 and 45 nucleotides in length.

As used herein, "nucleic acid polymerase" or "nucleic acid polymerization activity" refers to an enzyme that catalyzes the polymerization of nucleoside triphosphates. Generally, the enzyme will initiate synthesis at the 3'-end of the primer annealed to the target sequence, and will proceed in the 5'-direction along the template, and if possessing a 5' to 3' nuclease activity, hydrolyzing intervening, annealed probe to release both labeled and unlabeled probe subunit, until synthesis terminates. Known DNA polymerases include, for example, E. coli DNA polymerase I, T7 DNA polymerase, Thermus thermophilus (Tth) DNA polymerase, Bacillus stearothermophilus DNA polymerase, Thermococcus litoralis DNA polymerase, Thermus aquaticus (Taq) DNA polymerase and Pyrococcus furiosus (Pfu) DNA polymerase. If the nucleic acid template is RNA, then "nucleic acid polymerization activity" refers to an RNA-dependent polymerization activity, such as reverse transciptase.

Nucleic acid polymerases useful according to the invention include but are not limited to any of the following enzymes: DNA polymerase I from E. coli, and DNA polymerase from Thermus aquaticus (Taq), Thermus thermophilus (Tth), Pyrococcus furiosus (Pfu) and Thermus flavus (Tfl), Pfu, exo- Pfu (a mutant form of Pfu that lacks 3' to 5' exonuclease activity), the Stoffel fragment of Taq, N-truncated Bst, N-truncated Bca, Genta, JdF3 exo-, Vent, Vent exo- (a mutant form of Vent that lacks 3' to 5' exonuclease activity), Deep Vent, Deep Vent exo- (a mutant form of Deep Vent that lacks 3' to 5' exonuclease activity), U1Tma, Sequenase and Thermotoga maritima full length DNA pol I, not the U1Tma fragment. Additional nucleic acid polymerases useful according to the invention are included below in the section entitled, "Nucleic Acid Polymerases".

As used herein, a "polymerization temperature" that is useful according to the invention is selected such that a first subunit of a probe will not dissociate from a second subunit of a probe when the probe is not bound to the target nucleic acid at or below the polymerization temperature. A "polymerization temperature" that is useful according to the invention is also selected such that a first subunit of a probe will not dissociate from a second subunit of a probe when the probe is bound to the target nucleic acid and prior to the displacement of the first subunit of the probe from the target nucleic acid sequence by the primer extension product at or below the polymerization temperature. As used herein, a "polymerization temperature" that is useful according to the invention is also a temperature that is less than (at least 5° and preferably 10° C.) the $T_m$ of a probe having a secondary structure. A "polymerization temperature" is selected so that the three-dimensional structure of the probe, when not bound to the target nucleic acid sequence is, preferably, stable at or below the polymerization temperature.

In a preferred embodiment, the signal is detected or measured, wherein detecting and/or measuring the signal comprises detecting and/or measuring the amount of the released first subunit of the probe.

The invention also provides a method of detecting or measuring a target nucleic acid sequence comprising the following steps. A detection complex is formed by incubating a sample comprising a target nucleic acid sequence with a probe, wherein the probe comprises a first and a second subunit. The probe is bound to the target nucleic acid such that the first subunit of the probe is dissociated from the second subunit of the probe to release the first subunit of the probe, thereby generating a signal. According to this embodiment, binding is performed at a binding temperature. The first subunit of the probe does not dissociate from the second subunit of the probe when not bound to the target nucleic acid sequence at or below the binding temperature. The amount of the released first subunit is detected and/or measured as an indication of the presence of the target sequence in the sample.

The invention also provides a method of detecting or measuring a target nucleic acid sequence comprising the following steps. A detection complex is formed by incubating a sample comprising a target nucleic acid sequence, an upstream primer, and a downstream probe, wherein the probe comprises a first and a second subunit. The probe and primer are bound to the target nucleic acid. The detection complex is subjected to a nucleic acid polymerization activity under conditions which permit extension of the upstream primer by polymerization of a nucleic acid strand, and displacement of the first subunit of the probe from the target nucleic acid, such that the first subunit dissociates from the second subunit of the probe and is released to generate a signal. Binding is performed at a binding temperature and the first subunit of the probe does not dissociate from the second subunit of the probe when not bound to the target nucleic acid sequence at or below the binding temperature. Polymerization is performed at a polymerization temperature. The first subunit of the probe does not dissociate from the second subunit of the probe when not displaced by the nucleic acid strand, at or below the polymerization temperature. The amount of the released first subunit is detected and/or measured as an indication of the presence of the target sequence in the sample.

As used herein, "detecting a released first subunit of a probe" or "measuring the amount of released first subunit of a probe" refers to determining the presence of a particular target nucleic acid sequence in a sample or determining the amount of a particular target nucleic acid sequence in a sample as an indication of the presence of a target nucleic acid sequence in a sample. The amount of a target nucleic acid sequence that can be measured or detected is preferably about 1 molecule to $10^{20}$ molecules, more preferably about 100 molecules to $10^{17}$ molecules and most preferably about 1000 molecules to $10^{14}$ molecules. According to one embodiment of the invention, the detected nucleic acid is a released labeled subunit of the probe of a detection complex according to the invention (for example B" in FIG. 1A or A'B" in FIG. 1b), that dissociates from the second subunit of the probe. In one embodiment, the released, labeled subunit of the probe that is detected is displaced from the target nucleic acid sequence by the 3' extension of an upstream primer of a detection complex according to the invention (for example A'B" of FIG. 1b) and subsequently dissociates from the second subunit of the probe. According to the present invention, a label is attached to the 5' end of the first subunit of the probe (for example B" in FIG. 1a or A'B" in FIG. 1B) comprising a detection complex according to the invention. Alternatively, a label is attached to the 3' end of the first subunit of the probe and a quencher is attached to the 5' end of the first subunit of the probe. According to the invention, a label may be attached to the 3' end of the first subunit of the probe (for example B" in FIG. 1a or A'B" in FIG. 1B) comprising a detection complex according to the invention.

In another embodiment, a first member of an interactive label pair is attached to the first subunit of the probe and a second member of an interactive label pair is attached to a second subunit of the probe. According to this embodiment, the interactive labels are positioned to permit the separation of the labels during dissociation of the first and second subunits of the probe. In another embodiment, the probe subunit is labeled with a pair of interactive labels (e.g., a FRET or non-FRET pair) positioned to permit the separation of the labels during oligonucleotide probe unfolding (e.g., for example due to a change in the secondary structure of the probe) or hydrolysis.

The invention also provides for detecting and/or measuring the release of an unlabeled subunit of the probe. An unlabeled subunit of a probe can be detected by methods well known in the art, including but not limited to agarose gel electrophoresis and ethidium bromide staining, or Southern or northern blot analysis.

Preferably there is a direct correlation between the amount of the target nucleic acid sequence and the signal generated by the released probe subunit.

In another embodiment of the invention, the probe subunit is labeled with a pair of interactive labels (e.g., a FRET or non-FRET pair) positioned to permit the separation of the labels during oligonucleotide probe unfolding (e.g., for example due to a change in the secondary structure of the probe) or hydrolysis.

As used herein, "detecting the amount of the released first subunit of the probe" or "measuring the amount of the released first subunit of the probe" refers to determining the presence of a labeled or unlabeled probe subunit in a sample or determining the amount of a labeled or unlabeled probe subunit in a sample. Methods well known in the art and described herein can be used to detect or measure release of a labeled or unlabeled probe subunit. A method of detecting or measuring release of a labeled probe subunit will be appropriate for measuring or detecting the labeled moiety that is present on the labeled probe subunit. The amount of a released labeled probe subunit that can be measured or detected is preferably about 25%, more preferably about 50% and most preferably about 95% of the total starting amount of labeled probe. The detection methods described herein are operative for detecting a probe subunit wherein any amount of a probe subunit is detected whether that be a small or large proportion of the probe subunit generated in the reaction. Methods of detecting or measuring release of unlabeled probe subunit include, for example, gel electrophoresis or by hybridization, according to methods well known in the art. The detection methods described herein are operative when as little as 1 or 2 molecules (and up to 1 or 2 million, for example 10, 100, 1000, 10,000, 1 million) of released probe subunit is detected.

As used herein, a "labeled probe subunit" refers to a probe subunit, as defined herein, derived from a labeled detection complex according to the invention wherein the probe subunit is preferably between about 2–1000 nucleotides, more preferably between about 5–50 nucleotides and most preferably between about 16–18 nucleotides, and wherein the labeled probe subunit is released from a second subunit of the probe after binding to a target nucleic acid and can be detected by methods well known in the art and described herein.

In one embodiment, a probe is a bi-molecular or multi-molecular probe wherein a first molecule comprising the probe is labeled with a fluorophore and a second molecule comprising the probe is labeled with a quencher. As used herein, a "subprobe" and "subquencher" refer to a first molecule of a bi- or multi-molecular probe according to the invention, that is labeled with a fluorophore and a second molecule of a bi- or multi-molecular probe according to the invention, that is labeled with a quencher, respectively. According to this embodiment, following binding of the bi- or multi-molecular probe to the target nucleic acid, the subprobe and subquencher dissociate from each other (that is, the distance between the subprobe and the subquencher increases) and a signal is generated as a result of this dissociation and subsequent separation of the subprobe and subquencher.

In another embodiment, following binding of the bi- or multi-molecular probe and an upstream primer to the target nucleic acid to form a detection complex, the detection complex is subjected to a nucleic acid polymerization activity under conditions which permit extension of the upstream primer by polymerization of a nucleic acid strand. The extension product of the upstream primer displaces the first subunit/subprobe of the probe from the target nucleic acid sequence such that the first subunit of the probe dissociates from the second subunit/subquencher of the probe. As a result of this dissociation and subsequent separation of the subprobe and subquencher, a signal is generated.

In a preferred embodiment, the secondary structure is selected from the group consisting of a stem-loop structure, a hairpin structure, an internal loop, a bulge loop, a branched structure, a pseudoknot structure or a cloverleaf structure.

In another preferred embodiment, the first subunit of the probe further comprises at least one labeled moiety capable of providing a signal.

In another preferred embodiment, the detection complex is formed comprising a pair of interactive signal generating labeled moieties effectively positioned on the probe to quench the generation of a detectable signal when the probe is not bound to the target nucleic acid or when the first subunit of the probe is not dissociated from the second subunit of the probe.

In another preferred embodiment, the pair of interactive signal generating moieties comprises a quencher moiety and a fluorescent moiety.

The invention also provides for a polymerase chain reaction process for detecting a target nucleic acid sequence in a sample comprising the step of providing a detection complex comprising a probe, wherein the probe comprises a first and a second subunit, a set of oligonucleotide primers wherein a first primer contains a sequence complementary to a region in one strand of the target nucleic acid sequence and primes the synthesis of a complementary DNA strand, and a second primer contains a sequence complementary to a region in a second strand of the target nucleic acid sequence and primes the synthesis of a complementary DNA strand. This polymerase chain reaction process also includes the step of amplifying the target nucleic acid sequence. The amplification step employs a nucleic acid polymerase as a template-dependent polymerizing agent under conditions which are permissive for PCR cycling steps of (i) annealing of primers required for amplification to a template nucleic acid sequence contained within the target nucleic acid sequence, and (ii) extending the primers wherein the nucleic acid polymerase synthesizes a primer extension product, and thereby dissociates the first subunit of the probe from the second subunit of the probe, thereby creating detectable, released, labeled first subunits of the probe. According to this method of the invention, amplification is performed at an amplification temperature. The first subunit of the probe does not dissociate from the second subunit of the probe when not bound to the target nucleic acid sequence at or below the amplification temperature. The released, labeled first subunit of the probe is detected and/or measured as an indicator of the presence of the target sequence in the sample.

As used herein, an "oligonucleotide primer" refers to a single stranded DNA or RNA molecule that is hybridizable to a nucleic acid template and primes enzymatic synthesis of a second nucleic acid strand. Oligonucleotide primers useful according to the invention are between about 10 to 100 nucleotides in length, preferably about 17–50 nucleotides in length and more preferably about 17–45 nucleotides in length.

As used herein, "template dependent polymerizing agent" refers to an enzyme capable of extending an oligonucleotide primer in the presence of adequate amounts of the four deoxyribonucleoside triphosphates (dATP, dGTP, dCTP and dTTP) or analogs as described herein, in a reaction medium comprising appropriate salts, metal cations, appropriate stabilizers and a pH buffering system. Template dependent polymerizing agents are enzymes known to catalyze primer- and template-dependent DNA synthesis. In certain embodiments, template dependent polymerizing agents possess 5' to 3' nuclease activity.

As used herein, "amplifying" refers to producing additional copies of a nucleic acid sequence, including the method of the polymerase chain reaction.

The invention also provides for a polymerase chain reaction process for detecting a target nucleic acid sequence in a sample comprising the step of providing a detection complex comprising a probe, wherein the probe comprises a first and a second subunit, a set of oligonucleotide primers wherein a first primer contains a sequence complementary to a region in one strand of the target nucleic acid sequence and primes the synthesis of a complementary DNA strand, and a second primer contains a sequence complementary to a region in a second strand of the target nucleic acid sequence and primes the synthesis of a complementary DNA strand. This polymerase chain reaction process also includes the step of amplifying the target nucleic acid sequence. The amplification step employs a nucleic acid polymerase as a template-dependent polymerizing agent under conditions which are permissive for PCR cycling steps of (i) annealing of primers required for amplification to a template nucleic acid sequence contained within the target nucleic acid sequence, (ii) extending the primers wherein the nucleic acid polymerase synthesizes a primer extension product, and (iii) displacement of the first subunit of the probe from the target nucleic acid, by the primer extension product, such that the first subunit dissociates from the second subunit of the probe, thereby creating detectable, released, labeled first subunits of the probe. According to this method of the invention, amplification is performed at an amplification temperature. The first subunit of the probe does not dissociate from the second subunit of the probe when not bound to the target nucleic acid sequence, or when not displaced from the target nucleic acid by the primer extension product, at or below the amplification temperature. The released, labeled first subunit of the probe is detected and/or measured as an indicator of the presence of the target sequence in the sample.

In another preferred embodiment, the oligonucleotide primers of step b are oriented such that the forward primer is located upstream of the detection complex and the reverse primer is located downstream of the detection complex.

In another preferred embodiment, the nucleic acid polymerase has strand displacement activity. Nucleic acid polymerases exhibiting strand displacement activity and useful according to the invention include but are not limited to archacal DNA polymerases with "temperature activated" strand displacement activity (exo plus and exo minus versions of Vent, Deep Vent, Pfu, JDF-3, KOD (LTI's tradename Pfx), Pwo, 9 degrees North, *Thermococcus aggregans, Thermococcus gorgonarius*), and eubacterial DNA polymerases with strand displacement activity (exo minus Bst, exo minus Bca, Genta, Klenow fragment, exo minus Klenow fragment exo minus T7 DNA polymerase (Sequenase), Taq and Tth.

In another preferred embodiment, the nucleic acid polymerase is thermostable.

As used herein, "thermostable" refers to an enzyme which is stable and active at temperatures as great as preferably between about 90–100° C. and more preferably between about 70–98° C. to heat as compared, for example, to a non-thermostable form of an enzyme with a similar activity. For example, a thermostable nucleic acid polymerase derived from thermophilic organisms such as *P. furiosus, M. jannaschii, A. fulgidus* or *P. horikoshii* is more stable and active at elevated temperatures as compared to a nucleic acid polymerase from *E. coli*. A representative thermostable nucleic acid polymerase isolated from *Thermus aquaticus* (Taq) is described in U.S. Pat. No. 4,889,818 and a method for using it in conventional PCR is described in Saiki et al., 1988, *Science* 239:487. Another representative thermostable nucleic acid polymerase isolated from *P. furiosus* (Pfu) is described in Lundberg et al., 1991, *Gene*, 108:1–6. Additional representative temperature stable polymerases include, e.g., polymerases extracted from the thermophilic bacteria *Thermus flavus, Thermus ruber, Thermus thermophilus, Bacillus stearothermophilus* (which has a somewhat lower temperature optimum than the others listed), *Thermus lacteus, Thermus rubens, Thermotoga maritima*, or from thermophilic archaea *Thermococcus litoralis, Pyrococcus furiosus, Pyrococcus* sp. GBD, *Pysorcoccus horikohii, Thermococcus gorgonarius, Methanococcus jannaschii, Archeoglobus fulgidus* etc. . . . and *Methanothermus fervidus*.

Temperature stable polymerases are preferred in a thermocycling process wherein double stranded nucleic acids are denatured by exposure to a high temperature (about 95° C.) during the PCR cycle.

In another preferred embodiment, the labeled detection complex is formed by the addition of a labeled first subunit of the probe capable of providing a signal and a second subunit of the probe.

In another preferred embodiment, the detection complex is formed comprising a pair of interactive signal generating labeled moieties effectively positioned on the probe to quench the generation of a detectable signal when the probe is not bound to the target nucleic acid or when the first subunit of the probe is not dissociated from the second subunit of the probe.

In another preferred embodiment, the pair of interactive signal generating moieties comprises a quencher moiety and a fluorescent moiety.

In another preferred embodiment, the nucleic acid polymerase is selected from the group consisting of Taq polymerase and Pfu polymerase.

The invention also provides for a method of forming a detection complex comprising the steps of: providing a target nucleic acid sequence, providing a probe, wherein the probe comprises a first and a second subunit, and binding the target nucleic acid sequence, and the probe. According to this embodiment of the invention, binding is performed at a binding temperature and the first subunit of the probe does not dissociate from the second subunit of the probe when not bound to the target nucleic acid sequence at or below the binding temperature.

The invention also provides for a method of forming a detection complex comprising the steps of: providing a target nucleic acid sequence, providing an upstream primer complementary to the target nucleic acid sequence, providing a probe, wherein the probe comprises a first and a second subunit, and binding the target nucleic acid sequence, the upstream primer and the probe. According to this embodiment, binding is performed at a binding temperature and the first subunit of the probe does not dissociate from the second subunit of the probe when not bound to the target nucleic acid sequence at or below the binding temperature.

The invention also provides a composition comprising a target nucleic acid sequence, and a probe, wherein the probe comprises a first and a second subunit. The probe and the target nucleic acid can bind to form a detection complex. Binding is performed at a binding temperature, and the first subunit of the probe does not dissociate from the second subunit of the probe when not bound to the target nucleic acid sequence at or below the binding temperature.

The invention also provides a composition comprising a target nucleic acid sequence, a probe, wherein the probe comprises a first and a second subunit, an upstream primer and a nucleic acid polymerization activity. The probe, the primer and the target nucleic acid can bind to form a detection complex. Binding is performed at a binding temperature, and the first subunit of the probe does not dissociate from the second subunit of the probe when not bound to the target nucleic acid sequence at or below the binding temperature.

The invention also provides a kit for generating a signal indicative of the presence of a target nucleic acid sequence in a sample, comprising a probe and packaging means thereof. The probe of the kit comprises a first and a second subunit, and can bind to a target nucleic acid sequence to form a detection complex. Binding is performed at a binding temperature and the first subunit of the probe does not dissociate from the second subunit of the probe when not bound to the target nucleic acid sequence at or below the binding temperature.

The invention also provides a kit for generating a signal indicative of the presence of a target nucleic acid sequence in a sample, comprising an upstream primer, a downstream probe, wherein the probe comprises a first and a second subunit, a nucleic acid polymerization activity and packaging means thereof. The primer and the probe can bind to a target nucleic acid sequence to form a detection complex. Binding is performed at a binding temperature, and the first subunit of the probe does not dissociate from the second subunit of the probe when not bound to the target nucleic acid sequence at or below the binding temperature.

In a preferred embodiment, the probe comprises a labeled first subunit of the probe and a second subunit of the probe.

In another preferred embodiment, the first subunit of the probe comprises a pair of interactive signal generating labeled moieties effectively positioned to quench the generation of a detectable signal when the probe is not bound to the target nucleic acid or when at least the first subunit of the probe is not dissociated from at least the second subunit of the probe.

In another preferred embodiment, the pair of interactive signal generating moieties comprises a quencher moiety and a fluorescent moiety.

Further features and advantages of the invention are as follows. The claimed invention provides a method of generating a signal to detect and/or measure a target nucleic acid wherein the generation of a signal is an indication of the presence of a target nucleic acid in a sample. The method of the claimed invention does not require multiple steps. The method of the claimed invention does not require an enzymatic cleavage reaction for generation of a detectable signal. The claimed invention also provides a PCR based method for detecting and/or measuring a target nucleic acid comprising generating a signal as an indication of the presence of a target nucleic acid. The claimed invention also provides a PCR based method for detecting and/or measuring a target nucleic acid comprising generating a signal in the absence of an enzymatic cleavage reaction.

Further features and advantages of the invention will become more fully apparent in the following description of the embodiments and drawings thereof, and from the claims.

DESCRIPTION

Figure 1:
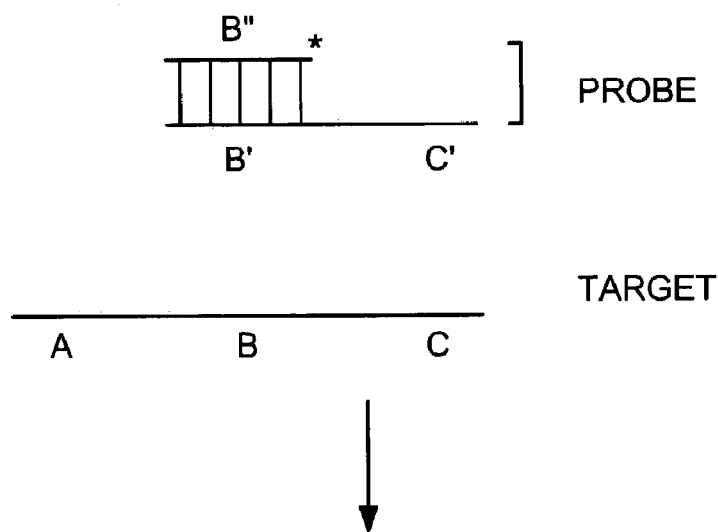
FIG. 1 demonstrates the formation of detection complexes of the invention.
Figure 1A:
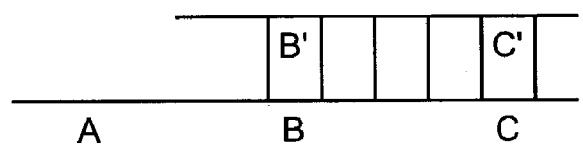
FIG. 1a demonstrates the formation of a detection complex comprising a probe comprising two subunits and a target nucleic acid.
Figures 1, 1B:
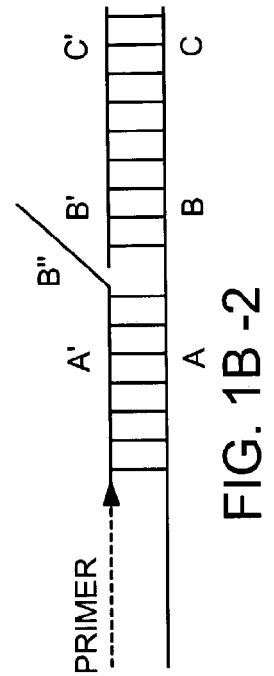
FIG. 1b demonstrates a probe comprising two subunits, a target nucleic acid and a primer.
Figures 1, 1B, 2:
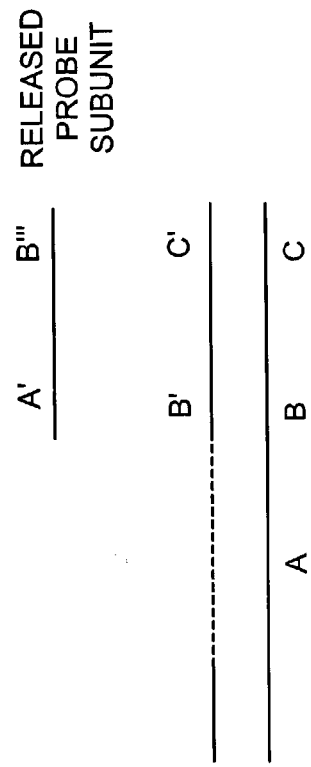
FIG. 2 demonstrates secondary structures.

The invention provides for a method of generating a signal to detect the presence of a target nucleic acid in a sample wherein a nucleic acid is treated with the combination of a probe comprising at least a first and a second subunit wherein a subunit of the probe dissociates from the remaining subunit(s) upon hybridization of the probe and the target nucleic acid. The invention also provides for a process for detecting or measuring a nucleic acid that allows for concurrent amplification and detection of a target nucleic acid sequence in a sample.

The practice of the present invention will employ, unless otherwise indicated, conventional techniques of molecular biology, microbiology and recombinant DNA techniques, which are within the skill of the art. Such techniques are explained fully in the literature. See, e.g., Sambrook, Fritsch & Maniatis, 1989, *Molecular Cloning: A Laboratory Manual*, Second Edition; *Oligonucleotide Synthesis* (M. J. Gait, ed., 1984); *Nucleic Acid Hybridization* (B. D. Harnes & S. J. Higgins, eds., 1984); *A Practical Guide to Molecular Cloning* (B. Perbal, 1984); and a series, *Methods in Enzymology* (Academic Press, Inc.); *Short Protocols In Molecular Biology*, (Ausubel et al., ed., 1995). All patents, patent applications, and publications mentioned herein, both supra and infra, are hereby incorporated by reference.

I. Nucleic Acid Polymerases

The invention provides for nucleic acid polymerases. Preferably, the nucleic acid polymerase according to the invention is thermostable.

Known DNA polymerases useful according to the invention include, for example, *E. coli* DNA polymerase I, *Thermus thermophilus* (Tth) DNA polymerase, *Bacillus stearothermophilus* DNA polymerase, *Thermococcus litoralis* DNA polymerase, *Thermus aquaticus* (Taq) DNA polymerase and *Pyrococcus furiosus* (Pfu) DNA polymerase.

Nucleic acid polymerases that exhibit 5' to 3' exonuclease activity are useful according to the invention.

Nucleic acid polymerases substantially lacking 5' to 3' exonuclease activity are also useful according to the invention and include but are not limited to Klenow and Klenow exo-, and T7 DNA polymerase (Sequenase).

Thermostable nucleic acid polymerases substantially lacking 5' to 3' exonuclease activity useful according to the invention include but are not limited to Pfu, exo- Pfu (a mutant form of Pfu that lacks 3' to 5' exonuclease activity), the Stoffel fragment of Taq, N-truncated Bst, N-truncated Bca, Genta, JDF-3, JdF3 exo- (a mutant form of JDF-3 that lacks 3' to 5' exonuclease activity), Vent, Vent exo- (a mutant form of Vent that lacks 3' to 5' exonuclease activity), Deep Vent, Deep Vent exo- (a mutant form of Deep Vent that lacks 3' to 5' exonuclease activity), UlTma, ThermoSequenase, AmpliTaq FS, KOD, KOD exo- (a mutant form of KOD that lacks 3' to 5' exonuclease activity), Tgo, Tgo exo- (a mutant form of Tgo that lacks 3' to 5' exonuclease activity).

Nucleic acid polymerases useful according to the invention include both native polymerases as well as polymerase mutants, which lack 5' to 3' exonuclease activity. Nucleic acid polymerases useful according to the invention can possess different degrees of thermostability. Preferably, a nucleic acid polymerase according to the invention exhibits strand displacement activity at the temperature at which it can extend a nucleic acid primer. In a preferred embodiment of the invention, a nucleic acid polymerase lacks both 5' to 3' and 3' to 5' exonuclease activity.

Additional nucleic acid polymerases substantially lacking 5' to 3' exonuclease activity with different degrees of thermostability useful according to the invention are listed below.

A. Bacteriophage DNA Polymerases (Useful for 37° C. Assays):

Bacteriophage DNA polymerases are devoid of 5' to 3' exonuclease activity, as this activity is encoded by a separate polypeptide. Examples of suitable DNA polymerases are T4, T7, and φ29 DNA polymerase. The enzymes available commercially are: T4 (available from many sources e.g., Epicentre) and T7 (available from many sources, e.g. Epicentre for unmodified and USB for 3' to 5' exo⁻ T7 "Sequenase" DNA polymerase).

B. Archaeal DNA Polymerases:

There are 2 different classes of DNA polymerases which have been identified in archaea:

1. Family B/pol α type (homologs of Pfu from *Pyrococcus furiosus*) and
2. pol II type (homologs of *P. furiosus* DP1/DP2 2-subunit polymerase). DNA polymerases from both classes have been shown to naturally lack an associated 5' to 3' exonuclease activity and to possess 3' to 5' exonuclease (proofreading) activity. Suitable DNA polymerases (pol α or pol II) can be derived from archaea with optimal growth temperatures that are similar to the desired assay temperatures. Examples of suitable archaea include, but are not limited to:

1. Thermolabile (useful for 37° C. assays)—e.g., *Methanococcus voltae*
2. Thermostable (useful for non-PCR assays)—e.g., *Sulfolobus solfataricus, Sulfolobus acidocaldarium, Methanococcus jannaschi, Thermoplasma acidophilum*. It is estimated that suitable archaea exhibit maximal growth temperatures of ≦80–85° C. or optimal growth temperatures of ≦70–80° C.
3. Thermostable (useful for PCR assays)—e.g., *Pyrococcus* species (*furiosus*, species GB-D, species strain KOD1, *woesii, abysii, horikoshii*), *Thermococcus* species (*litoralis*, species 9° North-7, species JDF-3, *gorgonarius*), *Pyrodictium occultum*, and *Archaeoglobus fulgidus*. It is estimated that suitable archaea would exhibit maximal growth temperatures of ≧80–85° C. or optimal growth temperatures of ≧70–80° C. Appropriate PCR enzymes from the archaeal pol a DNA polymerase group are commercially available, including KOD (Toyobo), Pfx (Life Technologies, Inc.), Vent (New England BioLabs), Deep Vent (New England BioLabs), and Tgo (Roche).

Additional archaea related to those listed above are described in the following references: *Archaea: A Laboratory Manual* (Robb, F. T. and Place, A. R., eds.), Cold Spring Harbor Laboratory Press, Cold Spring Harbor, N.Y., 1995 and *Thermophilic Bacteria* (Kristjansson, J. K.,ed.) CRC Press, Inc., Boca Raton, Fla., 1992.

C. Eubacterial DNA Polymerases:

There are 3 classes of eubacterial DNA polymerases, pol I, II, and III. Enzymes in the Pol I DNA polymerase family possess 5' to 3' exonuclease activity, and certain members also exhibit 3' to 5' exonuclease activity. Pol II DNA polymerases naturally lack 5' to 3' exonuclease activity, but do exhibit 3' to 5' exonuclease activity. Pol III DNA polymerases represent the major replicative DNA polymerase of the cell and are composed of multiple subunits. The pol III catalytic subunit lacks 5' to 3' exonuclease activity, but in some cases 3' to 5' exonuclease activity is located in the same polypeptide.

There are no commercial sources of eubacterial pol II and pol III DNA polymerases.

There are a variety of commercially available Pol I DNA polymerases, some of which have been modified to reduce or abolish 5' to 3' exonuclease activity. Methods used to eliminate 5' to 3' exonuclease activity of pol I DNA polymerases include:

mutagenesis (as described in Xu et al., 1997, *J. Mol. Biol.*, 268:284 and Kim et al., 1997, *Mol. Cells*, 7:468).

N-truncation by proteolytic digestion (as described in Klenow et al., 1971, *Eur. J. Biochem.*, 22: 371), or N-truncation by cloning and expressing as C-terminal fragments (as described in Lawyer et al., 1993, *PCR Methods Appl.*, 2:275).

As for archaeal sources, the assay-temperature requirements determine which eubacteria should be used as a source of a DNA polymerase useful according to the invention (e.g., mesophiles, thermophiles, hyperthermophiles).

1. Mesophilic/thermolabile (Useful for 37° C. Assays)
   i. DNA polymerases naturally substantially lacking 5' to 3' exonuclease activity: pol II or the pol III catalytic subunit from mesophilic eubacteria, such as *Escherchia coli, Streptococcus pneumoniae, Haemophilus influenza, Mycobacterium* species (*tuberculosis, leprae*)
   ii. DNA polymerase mutants substantially lacking 5' to 3' exonuclease activity: Pol I DNA polymerases for N-truncation or mutagenesis can be isolated from the mesophilic eubacteria listed above (Ci). A commercially-available eubacterial DNA polymerase pol I fragment is the Klenow fragment (N-truncated *E. coli* pol I; Stratagene).
2. Thermostable (Useful for non PCR Assays)
   i. DNA polymerases naturally substantially lacking 5' to 3' exonuclease activity: Pol II or the pol III catalytic subunit from thermophilic eubacteria, such as *Bacillus* species (e.g., *stearothermophilus, caldotenax, caldovelox*)
   ii. DNA polymerase mutants substantially lacking 5' to 3' exonuclease activity: Suitable pol I DNA polymerases for N-truncation or mutagenesis can be isolated from thermophilic eubacteria such as the *Bacillus* species listed above. Thermostable N-truncated fragments of *B. stearothermophilus* DNA polymerase pol I are commercially available and sold under the trade names Bst DNA polymerase I large fragment (Bio-Rad and Isotherm DNA polymerase (Epicentre)). A C-terminal fragment of *Bacillus caldotenax* pol I is available from Panvera (sold under the tradename Ladderman).
3. Thermostable (Useful for PCR Assays)
   i. DNA polymerases naturally substantially lacking 5' to 3' exonuclease activity: Pol II or pol III catalytic subunit from *Thermus* species (*aquaticus, thermophilus, flavus, ruber, caldophilus, filiformis, brokianus*) or from *Thermotoga maritima*. The catalytic pol III subunits from *Thermus thermophilus* and *Thermus aquaticus* are described in Yi-Ping et al., 1999, J. Mol. Evol., 48:756 and McHenry et al., 1997, J. Mol. Biol., 272:178.
   ii. DNA polymerase mutants substantially lacking 5' to 3' exonuclease activity: Suitable pol I DNA polymerases for N-truncation or mutagenesis can be isolated from a variety of thermophilic eubacteria, including *Thermus* species and *Thermotoga maritima* (see above). Thermostable fragments of *Thermus aquaticus* DNA polymerase pol I (Taq) are commercially available and sold under the trade names KlenTaq1 (Ab Peptides), Stoffel fragment (Perkin-Elmer), and *ThermoSequenase* (Amersham). In addition to C-terminal fragments, 5' to 3' exonuclease⁻ Taq mutants are also commercially available, such as TaqFS (Hoffmnan-LaRoche). In addition to 5'-3' exonuclease⁻ versions of Taq, an N-truncated version of *Thermotoga maritima* DNA polymerase I is also commercially available (tradename UlTma).

Additional eubacteria related to those listed above are described in *Thermophilic Bacteria* (Kristjansson, J. K.,ed.) CRC Press, Inc., Boca Raton, Fla., 1992.

D. Eukaryotic 5' to 3' Exonuclease⁻ DNA Polymerases (Useful for 37° C. Assays)

There are several DNA polymerases that have been identified in eukaryotes, including DNA pol α (replication/repair), δ (replication), ε (replication), β (repair) and γ (mitochondrial replication). Eukaryotic DNA polymerases are devoid of 5' to 3' exonuclease activity, as this activity is encoded by a separate polypeptide (e.g., mammalian FEN-1 or yeast RAD2). Suitable thermolabile DNA polymerases may be isolated from a variety of eukaryotes (including but not limited to yeast, mammalian cells, insect cells, *Drosophila*) and eukaryotic viruses (e.g., EBV, adenovirus).

Three 3' to 5' exonuclease motifs have been identified, and mutations in these regions have been shown to abolish 3' to 5' exonuclease activity in Klenow, ϕ29, T4, T7, and Vent DNA polymerases, yeast Pol α, Pol β, and Pol γ, and Bacillus subtilis Pol III (reviewed in Derbeyshire et al., 1995, Methods. Enzymol. 262:363). Methods for preparing additional DNA polymerase mutants, with reduced or abolished 3' to 5' exonuclease activity, are well known in the art.

Commercially-available enzymes that lack both 5' to 3' and 3' to 5' exonuclease activities include Sequenase (exo⁻ T7; USB), Pfu exo⁻ (Stratagene), exo⁻ Vent (New England BioLabs), exo⁻ DeepVent (New England BioLabs), exo⁻ Klenow fragment (Stratagene), Bst (Bio-Rad), Isotherm (Epicentre), Ladderman (Panvera), KlenTaq1 (Ab Peptides), Stoffel fragment (Perkin-Elmer), ThermoSequenase (USB), and TaqFS (Hoffmnan-LaRoche).

If polymerases other than Pfu are used, buffers and extension temperatures are selected to allow for optimal activity by the particular polymerase useful according to the invention. Buffers and extension temperatures useful for polymerases according to the invention are know in the art and can also be determined from the Vendor's specifications.

II. Nucleic Acids

A. Nucleic Acid Sequences Useful in the Invention

The invention provides for methods of detecting or measuring a target nucleic acid sequence; and also utilizes oligonucleotides, primers and probes for forming a detection complex according to the invention and primers for amplifying a template nucleic acid sequence. As used herein, the terms "nucleic acid", "polynucleotide" and "oligonucleotide" refer to primers, probes, and oligomer fragments to be detected, and shall be generic to polydeoxyribonucleotides (containing 2-deoxy-D-ribose), to polyribonucleotides (containing D-ribose), and to any other type of polynucleotide which is an N-glycoside of a purine or pyrimidine base, or modified purine or pyrimidine bases (including abasic sites). There is no intended distinction in length between the term "nucleic acid", "polynucleotide" and "oligonucleotide", and these terms will be used interchangeably. These terms refer only to the primary structure of the molecule. Thus, these terms include double- and single-stranded DNA, as well as double- and single-stranded RNA.

The complement of a nucleic acid sequence as used herein refers to an oligonucleotide which, when aligned with the nucleic acid sequence such that the 5' end of one sequence is paired with the 3' end of the other, is in "antiparallel association."

The oligonucleotide is not necessarily physically derived from any existing or natural sequence but may be generated in any manner, including chemical synthesis, DNA replication, reverse transcription or a combination thereof. The terms "oligonucleotide" or "nucleic acid" intend a polynucleotide of genomic DNA or RNA, cDNA, semisynthetic, or synthetic origin which, by virtue of its synthetic origin or manipulation: (1) is not associated with all or a portion of the polynucleotide with which it is associated in nature; and/or (2) is linked to a polynucleotide other than that to which it is linked in nature.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends.

When two different, non-overlapping oligonucleotides anneal to different regions of the same linear complementary nucleic acid sequence, and the 3' end of one oligonucleotide points toward the 5' end of the other, the former may be called the "upstream" oligonucleotide and the latter the "downstream" oligonucleotide.

Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength, and incidence of mismatched base pairs.

Stability of a nucleic acid duplex is measured by the melting temperature, or "$T_m$". The $T_m$ of a particular nucleic acid duplex under specified conditions is the temperature at which half of the base pairs have disassociated.

B. Primers and Probes Useful According to the Invention

The invention provides for oligonucleotide primers and probes useful for detecting or measuring a nucleic acid, for amplifying a template nucleic acid sequence, and for forming a detection complex according to the invention.

The term "primer" may refer to more than one primer and refers to an oligonucleotide, whether occurring naturally, as in a purified restriction digest, or produced synthetically, which is capable of acting as a point of initiation of synthesis along a complementary strand when placed under conditions in which synthesis of a primer extension product which is complementary to a nucleic acid strand is catalyzed. Such conditions include the presence of four different deoxyribonucleoside triphosphates and a polymerization-inducing agent such as DNA polymerase or reverse transcriptase, in a suitable buffer ("buffer" includes substituents which are cofactors, or which affect pH, ionic strength, etc.), and at a suitable temperature. The primer is preferably single-stranded for maximum efficiency in amplification.

Oligonucleotide primers useful according to the invention are single-stranded DNA or RNA molecules that are hybridizable to a template nucleic acid sequence and prime enzymatic synthesis of a second nucleic acid strand. The primer is complementary to a portion of a target molecule present in a pool of nucleic acid molecules. It is contemplated that oligonucleotide primers according to the invention are prepared by synthetic methods, either chemical or enzymatic. Alternatively, such a molecule or a fragment thereof is naturally-occurring, and is isolated from its natural source or purchased from a commercial supplier. Oligonucleotide primers are 5 to 100 nucleotides in length, ideally from 17 to 40 nucleotides, although primers of different length are of use. Primers for amplification are preferably about 17–25 nucleotides. Primers for the production of a detection complex according to the invention are preferably about 17–45 nucleotides. Primers useful according to the invention are also designed to have a particular melting temperature (Tm) by the method of melting temperature estimation. Commercial programs, including Oligo™, Primer Design and programs available on the internet, including Primer3 and Oligo Calculator can be used to calculate a Tm of a nucleic acid sequence useful according to the invention. Preferably, the Tm of an amplification primer useful according to the invention, as calculated for example by Oligo Calculator, is preferably between about 45 and 65° C. and more preferably between about 50 and 60° C.

Primers and probes according to the invention can be labeled and can be used to prepare a labeled detection complex. Pairs of single-stranded DNA primers, a DNA primer and a probe or a probe can be annealed to sequences within a target nucleic acid sequence. In certain embodiments, a primer can be used to prime amplifying DNA synthesis of a target nucleic acid sequence.

Typically, selective hybridization occurs when two nucleic acid sequences are substantially complementary (at least about 65% complementary over a stretch of at least 14 to 25 nucleotides, preferably at least about 75%, more preferably at least about 90% complementary). See Kanehisa, M., 1984, Nucleic Acids Res. 12: 203, incorporated herein by reference. As a result, it is expected that a certain degree of mismatch at the priming site is tolerated. Such mismatch may be small, such as a mono-, di- or trinucleotide. Alternatively, a region of mismatch may encompass loops, which are defined as regions in which there exists a mismatch in an uninterrupted series of four or more nucleotides.

Numerous factors influence the efficiency and selectivity of hybridization of the primer to a second nucleic acid molecule. These factors, which include primer length, nucleotide sequence and/or composition, hybridization temperature, buffer composition and potential for steric hindrance in the region to which the primer is required to hybridize, will be considered when designing oligonucleotide primers according to the invention.

A positive correlation exists between primer length and both the efficiency and accuracy with which a primer will anneal to a target sequence. In particular, longer sequences have a higher melting temperature ($T_M$) than do shorter ones, and are less likely to be repeated within a given target sequence, thereby minimizing promiscuous hybridization. Primer sequences with a high G-C content or that comprise palindromic sequences tend to self-hybridize, as do their intended target sites, since unimolecular, rather than bimolecular, hybridization kinetics are generally favored in solution. However, it is also important to design a primer that contains sufficient numbers of G-C nucleotide pairings since each G-C pair is bound by three hydrogen bonds, rather than the two that are found when A and T bases pair to bind the target sequence, and therefore forms a tighter, stronger bond. Hybridization temperature varies inversely with primer annealing efficiency, as does the concentration of organic solvents, e.g. formamide, that might be included in a priming reaction or hybridization mixture, while increases in salt concentration facilitate binding. Under stringent annealing conditions, longer hybridization probes, or synthesis primers, hybridize more efficiently than do shorter ones, which are sufficient under more permissive conditions. Preferably, stringent hybridization is performed in a suitable buffer (for example, 1× Sentinel Molecular Beacon PCR core buffer, Stratagene Catalog #600500; 1× Pfu buffer, Stratagene Catalog #200536; or 1× cloned Pfu buffer, Stratagene Catalog #200532) under conditions that allow the nucleic acid sequence to hybridize to the oligonucleotide primers and/or probes (e.g., 95° C.). Stringent hybridization conditions can vary (for example, from salt concentrations of less than about 1M, more usually less than about 500 mM and preferably less than about 200 mM) and hybridization temperatures can range (for example, from as low as 0° C. to greater than 22° C., greater than about 30° C., and (most often) in excess of about 37° C.), depending upon the lengths and/or the nucleic acid composition of the oligonucleotide primer and/or probes. Longer fragments may require higher hybridization temperatures for specific hybridization. As several factors affect the stringency of hybridization, the combination of parameters is more important than the absolute measure of a single factor.

Oligonucleotide primers can be designed with these considerations in mind and synthesized according to the following methods.

1. Oligonucleotide Primer Design Strategy

The design of a particular oligonucleotide primer useful according to the invention for the purpose of sequencing or PCR involves selecting a sequence that is capable of recognizing the target sequence, but has a minimal predicted secondary structure. The oligonucleotide sequence may or may not bind only to a single site in the target nucleic acid sequence. Furthermore, the Tm of the oligonucleotide is optimized by analysis of the length and GC content of the oligonucleotide. Furthermore, when designing a PCR primer useful for the amplification of genomic DNA, the selected primer sequence does not demonstrate significant matches to sequences in the GenBank database (or other available databases).

The design of a primer useful according to the invention is facilitated by the use of readily available computer programs, developed to assist in the evaluation of the several parameters described above and the optimization of primer sequences. Examples of such programs are "PrimerSelect" of the DNAStar™ software package (DNAStar, Inc.; Madison, Wis.), OLIGO 4.0 (National Biosciences, Inc.), PRIMER, Oligonucleotide Selection Program, PGEN and Amplify (described in Ausubel et al., 1995, Short Protocols in Molecular Biology, 3rd Edition, John Wiley & Sons). In one embodiment, primers are designed with sequences that serve as targets for other primers to produce a PCR product that has known sequences on the ends which serve as targets for further amplification (e.g. to sequence the PCR product). If many different target nucleic acid sequences are amplified with specific primers that share a common 'tail' sequence', the PCR products from these distinct genes can subsequently be sequenced with a single set of primers. Alternatively, in order to facilitate subsequent cloning of amplified sequences, primers are designed with restriction enzyme site sequences appended to their 5' ends. Thus, all nucleotides of the primers are derived from a target nucleic acid sequence or sequences adjacent to a target nucleic acid sequence, except for the few nucleotides necessary to form a restriction enzyme site. Such enzymes and sites are well known in the art. If the genomic sequence of a target nucleic acid sequence and the sequence of the open reading frame of a target nucleic acid sequence are known, design of particular primers is well within the skill of the art.

2. Synthesis

The primers themselves are synthesized using techniques that are also well known in the art. Methods for preparing oligonucleotides of specific sequence are known in the art, and include, for example, cloning and restriction digest analysis of appropriate sequences and direct chemical synthesis. Once designed, oligonucleotides are prepared by a suitable chemical synthesis method, including, for example, the phosphotriester method described by Narang et al., 1979, Methods in Enzymology, 68:90, the phosphodiester method disclosed by Brown et al., 1979, Methods in Enzymology, 68:109, the diethylphosphoramidate method disclosed in Beaucage et al., 1981, Tetrahedron Letters, 22:1859, and the solid support method disclosed in U.S. Pat. No. 4,458,066, or by other chemical methods using either a commercial automated oligonucleotide synthesizer (which is commercially available) or VLSIPS™ technology.

C. Probes

The invention provides for probes useful for forming a detection complex or a labeled detection complex as defined herein. Methods of preparing a labeled detection complex according to the invention are provided in the section entitled "Detection complex" below.

The general design of a probe according to the invention is described in the section entitled, "Primers and Probes Useful According to the Invention."

As used herein, the term "probe" refers to a probe comprising at least a first and second subunit, wherein the probe forms a duplex structure with a sequence in the target nucleic acid, due to complementarity of at least one sequence in at least one subunit of the probe with a sequence in the target region. As used herein, the term "probe" also refers to a probe comprising at least a first and second subunit and having a secondary structure that changes upon binding of the probe to a target nucleic acid sequence, as defined herein, wherein the probe forms a duplex structure with a sequence in the target nucleic acid, due to complementarity of at least one sequence in at least one subunit of the probe with a sequence in the target region. A probe according to the invention can also be labeled. In embodiments wherein a detection complex comprises an upstream primer, a target nucleic acid and a probe, as defined herein, the probe, preferably, does not contain a sequence complementary to sequence(s) used in the primer extension (s). Generally the 3' terminus of the subunit(s) of the probe that binds to the target nucleic acid sequence will be "blocked" to prohibit incorporation of the probe into a primer extension product, according to this embodiment. Methods of labeling a probe according to the invention and suitable labels are described below in the section entitled "Detection Complex".

A probe according to the invention is capable of forming a secondary structure as defined herein, (including a stem loop, a hairpin, an internal loop, a bulge loop, a branched structure and a pseudoknot) or multiple secondary structures, cloverleaf type structures or any three-dimensional structure as defined hereinabove.

For example, according to one embodiment of the present invention, a probe can be at least two associated oligonucleotides, wherein the probe has secondary structure such as a hairpin or a stem-loop, and includes, but wherein the probe is not limited to molecular beacon, safety pin, scorpion, and sunrise/amplifluor probes. The invention encompasses a probe wherein at least one subunit of the probe comprises a secondary structure such as a stem loop or hairpin, or wherein at least one subunit of the probe comprises a molecular beacon, a safety pin, a scorpion, or a sunrise/amplifluor structure, an internal loop, a bulge loop, a branched structure and a pseudoknot.

Molecular beacon probes comprise a hairpin, or stem-loop structure which possesses a pair of interactive signal generating labeled moieties (e.g., a fluorophore and a quencher) effectively positioned to quench the generation of a detectable signal when the beacon probe is not hybridized to the target nucleic acid sequence. The loop comprises a region that is complementary to a target nucleic acid. The loop is flanked by 5' and 3' regions ("arms") that reversibly interact with one another by means of complementary nucleic acid sequences when the region of the probe that is complementary to a nucleic acid target sequence is not bound to the target nucleic acid. Alternatively, the loop is flanked by 5' and 3' regions ("arms") that reversibly interact with one another by means of attached members of an affinity pair to form a secondary structure when the region of the probe that is complementary to a nucleic acid target sequence is not bound to the target nucleic acid. As used herein, "arms" refers to regions of a molecular beacon probe that a) reversibly interact with one another by means of complementary nucleic acid sequences when the region of the probe that is complementary to a nucleic acid target sequence is not bound to the target nucleic acid or b) regions of a probe that reversibly interact with one another by means of attached members of an affinity pair to form a secondary structure when the region of the probe that is complementary to a nucleic acid target sequence is not bound to the target nucleic acid. When a molecular beacon probe is not hybridized to target, the arms hybridize with one another to form a stem hybrid, which is sometimes referred to as the "stem duplex". This is the closed conformation. When a molecular beacon probe hybridizes to its target the "arms" of the probe are separated. This is the open conformation. In the open conformation an arm may also hybridize to the target. Such probes may be free in solution, or they may be tethered to a solid surface. When the arms are hybridized (e.g., form a stem) the quencher is very close to the fluorophore and effectively quenches or suppresses its fluorescence, rendering the probe dark. Such probes are described in U.S. Pat. No. 5,925,517 and U.S. Pat. No. 6,037,130. The invention encompasses molecular beacon probes wherein one or more subunits of the probe comprise a molecular beacon structure.

As used herein, a molecular beacon probe can also be an "allele-discriminating" probe as described herein.

Molecular beacon probes have a fluorophore attached to one arm and a quencher attached to the other arm. The fluorophore and quencher, for example, tetramethylrhodamine and DABCYL, need not be a FRET pair. For example, in one embodiment, a fluorophore is attached to one arm of the probe subunit comprising a molecular beacon structure and a quencher is attached to the other arm of the probe subunit comprising a molecular beacon structure.

For stem loop probes useful in this invention, the length of the probe or probe subunit sequence that is complementary to the target, the length of the regions of a probe or probe subunit (e.g., stem hybrid) that reversibly interact with one another by means of complementary nucleic acid sequences, when the region complementary to a nucleic acid target sequence is not bound to the target nucleic acid, and the relation of the two, is designed according to the assay conditions for which the probe is to be utilized. The lengths of the target-complementary sequences and the stem hybrid sequences for particular assay conditions can be estimated according to what is known in the art. The regions of a probe that reversibly interact with one another by means of complementary nucleic acid sequences when the region of the probe that is complementary to a nucleic acid target sequence is not bound to the target nucleic acid are in the range of 6 to 100, preferably 8 to 50 nucleotides and most preferably 8 to 25 nucleotides each. The length of the probe sequence that is complementary to the target is preferably 17–40 nucleotides, more preferably 17–30 nucleotides and most preferably 17–25 nucleotides long.

The oligonucleotide sequences of molecular beacon probes modified according to this invention may be DNA, RNA, cDNA or combinations thereof. Modified nucleotides may be included, for example nitropyrole-based nucleotides or 2'-O-methylribonucleotides. Modified linkages also may be included, for example phosphorothioates. Modified nucleotides and modified linkages may also be incorporated in wavelength-shifting primers according to this invention.

Figure 5:
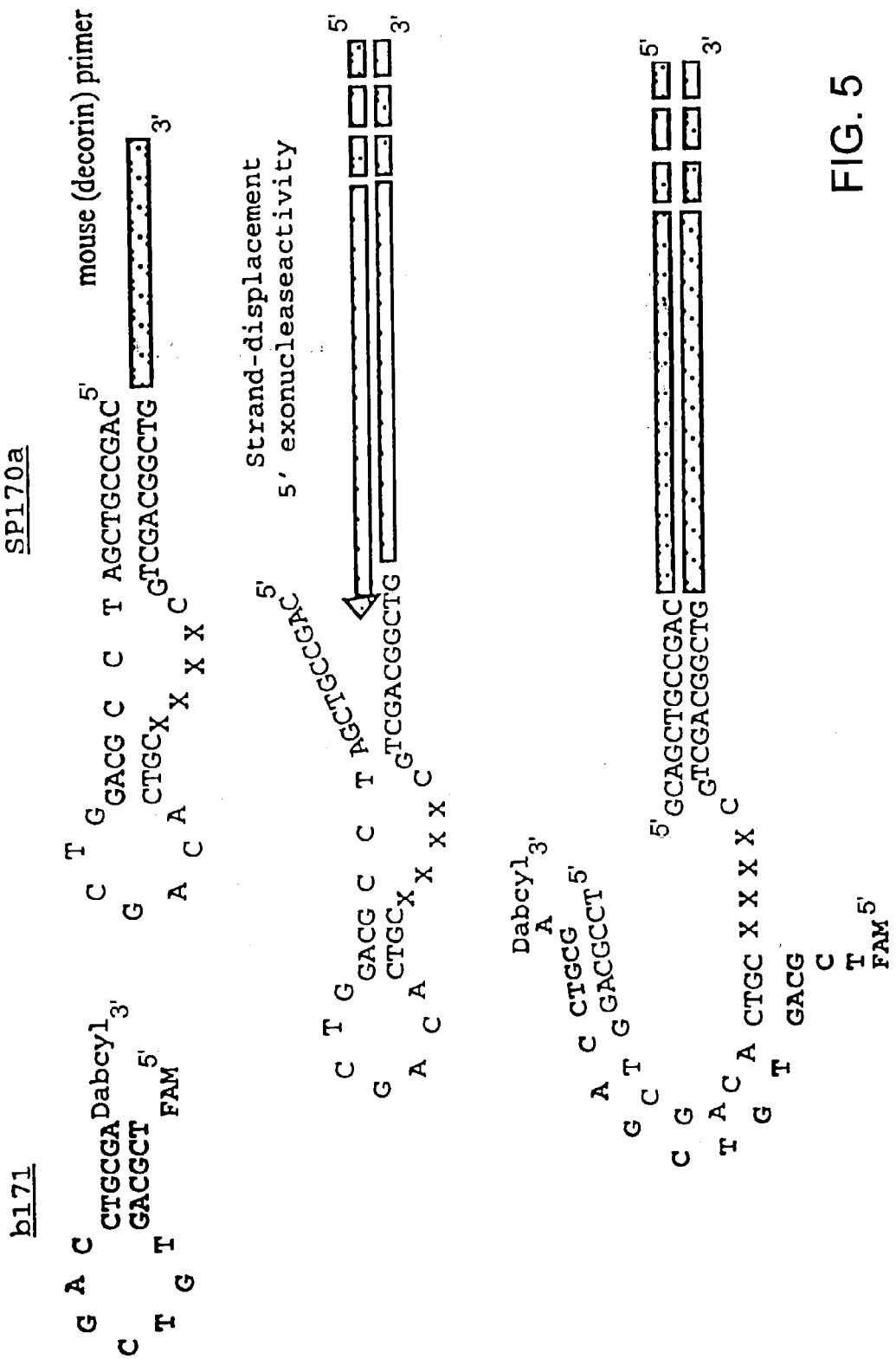
FIG. 5 is a representation of a safety pin probe. "Universal" hairpin probe 1 (b 171) is represented by SEQ ID NO: 17. Probe 2 (SP170a) is represented by SEQ ID NO: 18. The top strand synthesized by the polymerase is represented by SEQ ID NO: 19. The displaced and degraded top strand that opens up or unfolds and serves as a target for for hairpin probe 1 is represented by SEQ ID NO: 20.

A safety pin probe, as utilized in the present invention, requires a "universal" hairpin probe 1 (FIG. 5, b171), comprising a hairpin structure, with a fluorophore (FAM) on the 5' arm of the hairpin and a quencher (Dabcyl) on the 3' arm, and a probe 2 (FIG. 5, SP170a) comprising a stem-loop comprising two domains: the 5' two thirds of probe 2 have a (universal) sequence complementary to the hairpin probe 1, and nucleotides that will stop the DNA polymerase, and the 3' one third of probe 2, which serves as the target specific primer. As the polymerase, primed from the reverse primer (that is, the 3' one third of probe 2) synthesizes the top strand, the 5' end of probe 2 will be displaced and degraded by the 5' exonucleolytic activity until the "stop nucleotides" are reached. At this time the remainder of probe 2 opens up or unfolds and serves as a target for hairpin probe 1, thereby separating the fluorophore from the quencher (FIG. 5).

Figure 6:
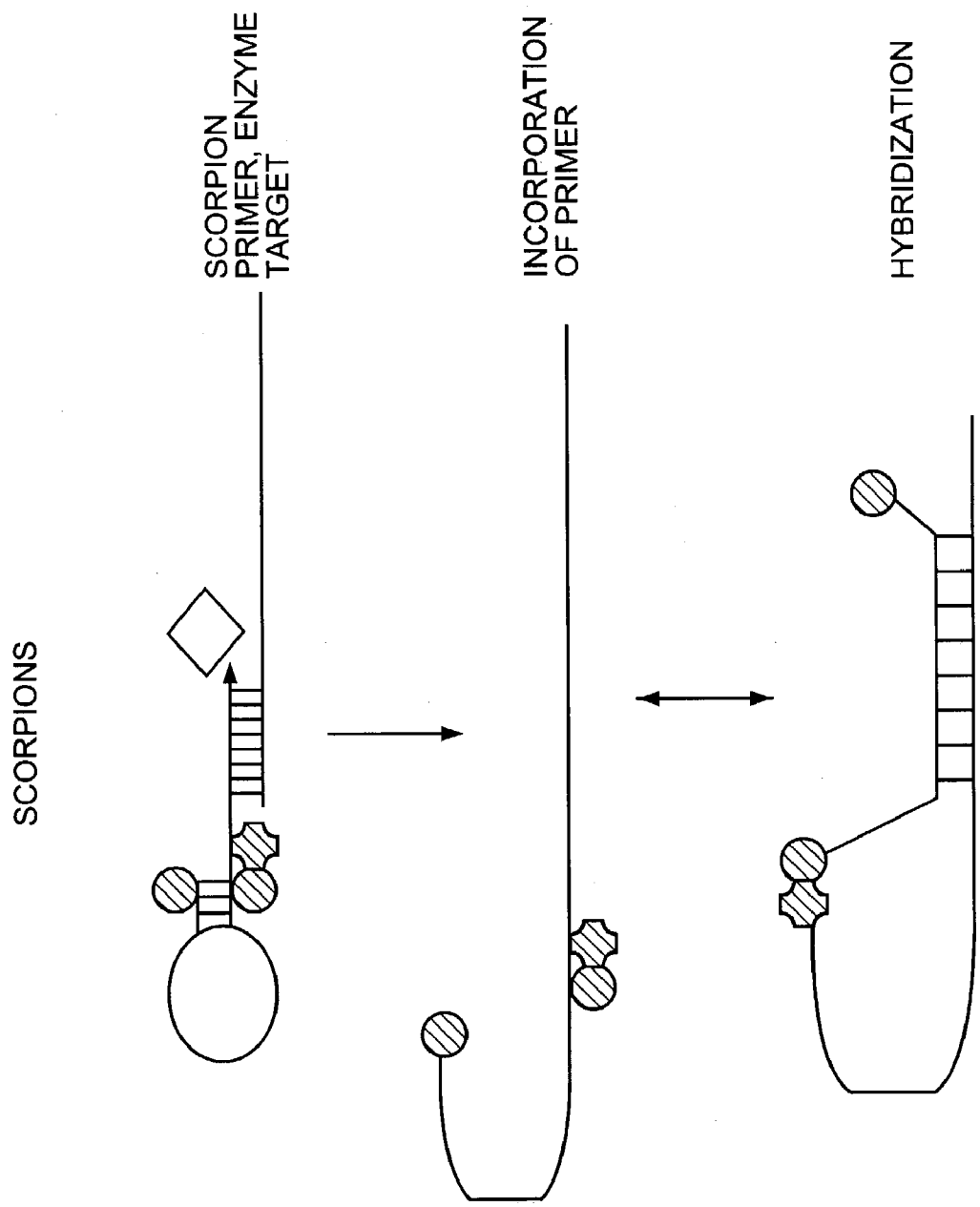
FIG. 6 is a representation of a scorpion probe.

Scorpion probes, as used in the present invention comprise a 3' primer with a 5' extended probe tail comprising a hairpin structure which possesses a fluorophore/quencher pair. The probe tail is "protected" from replication in the 5'→3' direction by the inclusion of hexethlyene glycol (HEG) which blocks the polymerase from replicating the probe. During the first round of amplification the 3' target-specific primer anneals to the target and is extended such that the scorpion is now incorporated into the newly synthesized strand, which possesses a newly synthesized target region for the 5' probe. During the next round of denaturation and annealing, the probe region of the scorpion hairpin loop will hybridize to the target, thus separating the fluorophore and quencher and creating a measurable signal. Such probes are described in Whitcombe et al., *Nature Biotechnology* 17: 804–807 (1999), and in FIG. 6.

Figure 7:
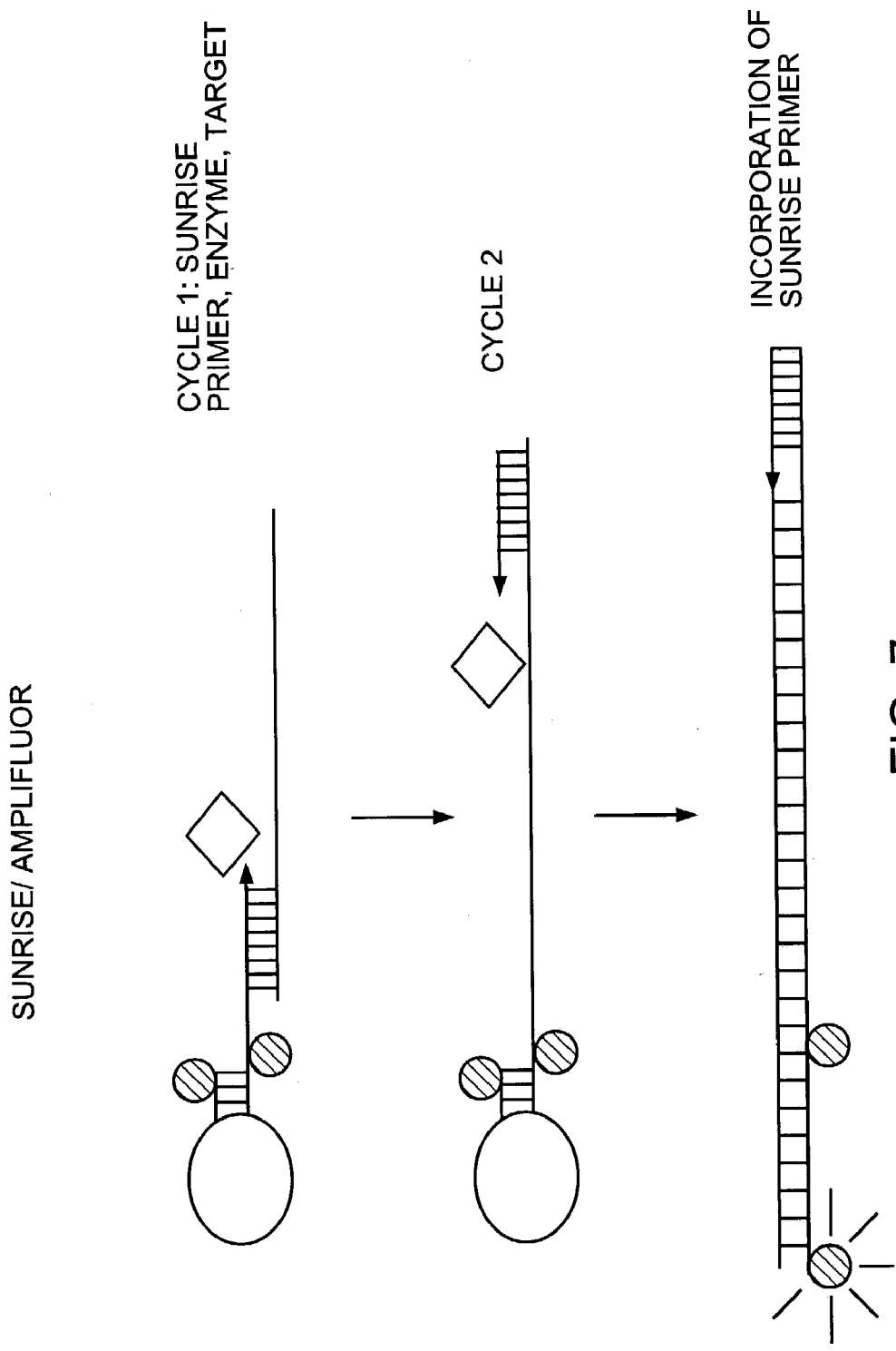
FIG. 7 is a representation of a sunrise/amplifluor probe

An additional oligonucleotide probe useful in the present invention is the sunrise/amplifluor probe. The sunrise/amplifluor probe is of similar construction as the scorpion probe with the exception that it lacks the HEG monomer to block the 5'→3' replication of the hairpin probe region. Thus, in the first round of amplification, the 3' target specific primer of the sunrise/amplifluor anneals to the target and is extended, thus incorporating the hairpin probe into the newly synthesized strand (sunrise strand). During the second round of amplification a second, non-labeled primer anneals to the 3' end of the sunrise strand (Cycle 2 in FIG. 7). However, as the polymerase reaches the 5' end of the hairpin, due to the lack of the HEG stop sequence, the polymerase will displace and replicate the hairpin, thus separating the fluorophore and quencher, and incorporating the linearized hairpin probe into the new strand. Probes of this type are described further in Nazameko et al., *Nucleic Acid Res.* 25: 2516–2521 (1997), and in FIG. 7.

For safety pin, scorpion and sunrise/amplifluor probes useful in this invention, the length of the probe sequence that is complementary to the target, the length of the regions of a probe (e.g., stem hybrid) that reversibly interact with one another by means of complementary nucleic acid sequences when the region complementary to a nucleic acid target sequence is not bound to the target nucleic acid and the relation of the two is designed according to the assay conditions for which the probe is to be utilized. The lengths of the target-complementary sequences and the stem hybrid sequences for particular assay conditions can be estimated according to what is known in the art. The regions of a probe that reversibly interact with one another by means of complementary nucleic acid sequences when the region complementary to a nucleic acid target sequence is not bound to the target nucleic acid are in the range of 6 to 100, preferably 8 to 50 nucleotides and most preferably 8 to 25 nucleotides each. The length of the probe sequence that is complementary to the target is preferably 17–40 nucleotides, more preferably 17–30 nucleotides and most preferably 17–25 nucleotides long. The stability of the interaction between the regions of a probe that reversibly interact with one another by means of complementary nucleic acid sequences is determined by routine experimentation to achieve proper functioning. In addition to length, stability of the interaction of the regions of a probe that reversibly interact with one another by means of complementary nucleic acid sequences between the regions of a probe can be adjusted by altering the G-C content and inserting destabilizing mismatches. One of the regions of a probe that reversibly interact with one another by means of complementary nucleic acid sequences can be designed to be partially or completely complementary to the target. If the 3' arm is complementary to the target the probe can serve as a primer for a DNA polymerase. Also, wavelength-shifting molecular beacon probes can be immobilized to solid surfaces, as by tethering, or be free-floating.

A wide range of fluorophores may be used in probes and primers according to this invention. Available fluorophores include coumarin, fluorescein, tetrachlorofluorescein, hexachlorofluorescein, Lucifer yellow, rhodamine, BODIPY, tetramethylrhodamine, Cy3, Cy5, Cy7, eosine, Texas red and ROX. Combination fluorophores such as fluorescein-rhodamine dimers, described, for example, by Lee et al. (1997), Nucleic Acids Research 25:2816, are also suitable. Fluorophores may be chosen to absorb and emit in the visible spectrum or outside the visible spectrum, such as in the ultraviolet or infrared ranges.

Suitable quenchers described in the art include particularly DABCYL and variants thereof, such as DABSYL, DABMI and Methyl Red. Fluorophores can also be used as quenchers, because they tend to quench fluorescence when touching certain other fluorophores. Preferred quenchers are either chromophores such as DABCYL or malachite green, or fluorophores that do not fluoresce in the detection range when the probe is in the open conformation.

D. Production of a Nucleic Acid

The invention provides nucleic acids to be detected and or measured, for amplification of a target nucleic acid sequence and for formation of a detection complex.

The present invention utilizes nucleic acids comprising RNA, cDNA, genomic DNA, synthetic forms, and mixed polymers. The invention includes both sense and antisense strands of a nucleic acid. According to the invention, the nucleic acid may be chemically or biochemically modified or may contain non-natural or derivatized nucleotide bases. Such modifications include, for example, labels, methylation, substitution of one or more of the naturally occurring nucleotides with an analog, internucleotide modifications such as uncharged linkages (e.g. methyl phosphonates, phosphorodithioates, etc.), pendent moieties (e.g., polypeptides), intercalators, (e.g. acridine, psoralen, etc.) chelators, alkylators, and modified linkages (e.g. alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

1. Nucleic Acids Comprising DNA a. Cloning

Nucleic acids comprising DNA can be isolated from cDNA or genomic libraries by cloning methods well known to those skilled in the art (Ausubel et al., supra). Briefly, isolation of a DNA clone comprising a particular nucleic acid sequence involves screening a recombinant DNA or cDNA library and identifying the clone containing the desired sequence. Cloning will involve the following steps. The clones of a particular library are spread onto plates, transferred to an appropriate substrate for screening, denatured, and probed for the presence of a particular nucleic acid. A description of hybridization conditions, and methods for producing labeled probes is included below.

The desired clone is preferably identified by hybridization to a nucleic acid probe or by expression of a protein that can be detected by an antibody. Alternatively, the desired clone is identified by polymerase chain amplification of a sequence defined by a particular set of primers according to the methods described below.

The selection of an appropriate library involves identifying tissues or cell lines that are an abundant source of the desired sequence. Furthermore, if a nucleic acid of interest contains regulatory sequence or intronic sequence a genomic library is screened (Ausubel et al., supra).

b. Genomic DNA

Nucleic acid sequences of the invention are amplified from genomic DNA. Genomic DNA is isolated from tissues or cells according to the following method.

To facilitate detection of a variant form of a gene from a particular tissue, the tissue is isolated free from surrounding normal tissues. To isolate genomic DNA from mammalian tissue, the tissue is minced and frozen in liquid nitrogen. Frozen tissue is ground into a fine powder with a prechilled mortar and pestle, and suspended in digestion buffer (100 mM NaCl, 10 mM Tris-HCl, pH 8.0, 25 mM EDTA, pH 8.0, 0.5% (w/v) SDS, 0.1 mg/ml proteinase K) at 1.2 ml digestion buffer per 100 mg of tissue. To isolate genomic DNA from mammalian tissue culture cells, cells are pelleted by centrifugation for 5 min at 500×g, resuspended in 1–10 ml ice-cold PBS, repelleted for 5 min at 500×g and resuspended in 1 volume of digestion buffer.

Samples in digestion buffer are incubated (with shaking) for 12–18 hours at 50° C., and then extracted with an equal volume of phenol/chloroform/isoamyl alcohol. If the phases are not resolved following a centrifugation step (10 min at 1700×g), another volume of digestion buffer (without proteinase K) is added and the centrifugation step is repeated. If a thick white material is evident at the interface of the two phases, the organic extraction step is repeated. Following extraction the upper, aqueous layer is transferred to a new tube to which will be added ½ volume of 7.5M ammonium acetate and 2 volumes of 100% ethanol. The nucleic acid is pelleted by centrifugation for 2 min at 1700×g, washed with 70% ethanol, air dried and resuspended in TE buffer (10 mM Tris-HCl, pH 8.0, 1 mM EDTA, pH 8.0) at 1 mg/ml. Residual RNA is removed by incubating the sample for 1 hour at 37° C. in the presence of 0.1% SDS and 1 µg/ml DNase-free RNase, and repeating the extraction and ethanol precipitation steps. The yield of genomic DNA, according to this method is expected to be approximately 2 mg DNA/1 g cells or tissue (Ausubel et al., supra). Genomic DNA isolated according to this method can be used for PCR analysis, according to the invention.

c. Restriction Digest (of cDNA or Genomic DNA)

Following the identification of a desired cDNA or genomic clone containing a particular target nucleic acid sequence, nucleic acids of the invention may be isolated from these clones by digestion with restriction enzymes.

The technique of restriction enzyme digestion is well known to those skilled in the art (Ausubel et al., supra). Reagents useful for restriction enzyme digestion are readily available from commercial vendors including Stratagene, as well as other sources.

d. PCR

Nucleic acids of the invention may be amplified from genomic DNA or other natural sources by the polymerase chain reaction (PCR). PCR methods are well-known to those skilled in the art.

PCR provides a method for rapidly amplifying a particular DNA sequence by using multiple cycles of DNA replication catalyzed by a thermostable, DNA-dependent DNA polymerase to amplify the target sequence of interest. PCR requires the presence of a target nucleic acid sequence to be amplified, two single stranded oligonucleotide primers flanking the sequence to be amplified, a DNA polymerase, deoxyribonucleoside triphosphates, a buffer and salts.

PCR, is performed as described in Mullis and Faloona, 1987, Methods Enzymol., 155: 335, herein incorporated by reference.

The polymerase chain reaction (PCR) technique, is disclosed in U.S. Pat. Nos. 4,683,202, 4,683,195 and 4,800,159. In its simplest form, PCR is an in vitro method for the enzymatic synthesis of specific DNA sequences, using two oligonucleotide primers that hybridize to opposite strands and flank the region of interest in the target DNA. A repetitive series of reaction steps involving template denaturation, primer annealing and the extension of the annealed primers by DNA polymerase results in the exponential accumulation of a specific fragment whose termini are defined by the 5' ends of the primers. PCR is reported to be capable of producing a selective enrichment of a specific DNA sequence by a factor of $10^9$. The PCR method is also described in Saiki et al., 1985, *Science* 230:1350.

PCR is performed using template DNA (at least 1 fg; more usefully, 1–1000 ng) and at least 25 pmol of oligonucleotide primers. A typical reaction mixture includes: 2 µl of DNA, 25 pmol of oligonucleotide primer, 2.5 µl of a suitable buffer, 0.4 µl of 1.25 µM dNTP, 2.5 units of Taq DNA polymerase (Stratagene) and deionized water to a total volume of 25 µl. Mineral oil is overlaid and the PCR is performed using a programmable thermal cycler.

The length and temperature of each step of a PCR cycle, as well as the number of cycles, are adjusted according to the stringency requirements in effect. Annealing temperature and timing are determined both by the efficiency with which a primer is expected to anneal to a template and the degree of mismatch that is to be tolerated. The ability to optimize the stringency of primer annealing conditions is well within the knowledge of one of moderate skill in the art. An annealing temperature of between 30° C. and 72° C. is used. Initial denaturation of the template molecules normally occurs at between 92° C. and 99° C. for 4 minutes, followed by 20–40 cycles consisting of denaturation (94–99° C. for 15 seconds to 1 minute), annealing (temperature determined as discussed above; 1–2 minutes), and extension (72° C. for 1 minute). The final extension step is generally carried out for 4 minutes at 72° C., and may be followed by an indefinite (0–24 hour) step at 4° C.

Detection methods generally employed in standard PCR techniques use a labeled probe with the amplified DNA in a hybridization assay. Preferably, the probe is labeled, e.g., with $^{32}$P, biotin, horseradish peroxidase (HRP), etc., to allow for detection of hybridization.

Other means of detection include the use of fragment length polymorphism (PCR FLP), hybridization to allele-specific oligonucleotide (ASO) probes (Saiki et al., 1986, *Nature* 324:163), or direct sequencing via the dideoxy method (using amplified DNA rather than cloned DNA). The standard PCR technique operates (essentially) by replicating a DNA sequence positioned between two primers, providing as the major product of the reaction a DNA sequence of discrete length terminating with the primer at the 5' end of each strand. Thus, insertions and deletions between the primers result in product sequences of different lengths, which can be detected by sizing the product in PCR-FLP. In an example of ASO hybridization, the amplified DNA is fixed to a nylon filter (by, for example, UV irradiation) in a series of "dot blots", then allowed to hybridize with an oligonucleotide probe labeled with HRP under stringent conditions. After washing, terramethylbenzidine (TMB) and hydrogen peroxide are added: HRP oxidizes the hydrogen peroxide, which in turn oxidizes the TMB to a blue precipitate, indicating a hybridized probe.

A PCR assay for detecting or measuring a nucleic acid according to the invention is described in the section entitled "Methods of Use".

2. Nucleic Acids Comprising RNA

The present invention also provides a nucleic acid comprising RNA.

Nucleic acids comprising RNA can be purified according to methods well known in the art (Ausubel et al., supra). Total RNA can be isolated from cells and tissues according to methods well known in the art (Ausubel et al., supra) and described below.

RNA is purified from mammalian tissue according to the following method. Following removal of the tissue of interest, pieces of tissue of ≦2 g are cut and quick frozen in liquid nitrogen, to prevent degradation of RNA. Upon the addition of a suitable volume of guanidinium solution (for example 20 ml guanidinium solution per 2 g of tissue), tissue samples are ground in a tissuemizer with two or three 10-second bursts. To prepare tissue guanidinium solution (1 L) 590.8 g guanidinium isothiocyanate is dissolved in approximately 400 ml DEPC-treated H$_2$O. 25 ml of 2 M Tris-HCl, pH 7.5 (0.05 M final) and 20 ml Na$_2$EDTA (0.01 M final) is added, the solution is stirred overnight, the volume is adjusted to 950 ml, and 50 ml 2-ME is added.

Homogenized tissue samples are subjected to centrifugation for 10 min at 12,000×g at 12° C. The resulting supernatant is incubated for 2 min at 65° C. in the presence of 0.1 volume of 20% Sarkosyl, layered over 9 ml of a 5.7M CsCl solution (0.1 g CsCl/ml), and separated by centrifugation overnight at 113,000×g at 22° C. After careful removal of the supernatant, the tube is inverted and drained. The bottom of the tube (containing the RNA pellet) is placed in a 50 ml plastic tube and incubated overnight (or longer) at 4° C. in the presence of 3 ml tissue resuspension buffer (5 mM EDTA, 0.5% (v/v) Sarkosyl, 5% (v/v) 2-ME) to allow complete resuspension of the RNA pellet. The resulting RNA solution is extracted sequentially with 25:24:1 phenol/chloroform/isoamyl alcohol, followed by 24:1 chloroform/isoamyl alcohol, precipitated by the addition of 3 M sodium acetate, pH 5.2, and 2.5 volumes of 100% ethanol, and resuspended in DEPC water (Chirgwin et al., 1979, *Biochemistry*, 18: 5294).

Alternatively, RNA is isolated from mammalian tissue according to the following single step protocol. The tissue of interest is prepared by homogenization in a glass teflon homogenizer in 1 ml denaturing solution (4M guanidinium thiosulfate, 25 mM sodium citrate, pH 7.0, 0.1M 2-ME, 0.5% (w/v) N-laurylsarkosine) per 100 mg tissue. Following transfer of the homogenate to a 5-ml polypropylene tube, 0.1 ml of 2 M sodium acetate, pH 4, 1 ml water-saturated phenol, and 0.2 ml of 49:1 chloroform/isoamyl alcohol are added sequentially. The sample is mixed after the addition of each component, and incubated for 15 min at 0–4° C. after all components have been added. The sample is separated by centrifugation for 20 min at 10,000×g, 4° C., precipitated by the addition of 1 ml of 100% isopropanol, incubated for 30 minutes at −20° C. and pelleted by centrifugation for 10 minutes at 10,000×g, 4° C. The resulting RNA pellet is dissolved in 0.3 ml denaturing solution, transferred to a microfuge tube, precipitated by the addition of 0.3 ml of 100% isopropanol for 30 minutes at −20° C., and centrifuged for 10 minutes at 10,000×g at 4° C. The RNA pellet is washed in 70% ethanol, dried, and resuspended in 100–200 µl DEPC-treated water or DEPC-treated 0.5% SDS (Chomczynski and Sacchi, 1987, *Anal. Biochem.*, 162: 156).

Nucleic acids comprising RNA can be produced according to the method of in vitro transcription.

The technique of in vitro transcription is well known to those of skill in the art. Briefly, the gene of interest is inserted into a vector containing an SP6, T3 or T7 promoter. The vector is linearized with an appropriate restriction enzyme that digests the vector at a single site located downstream of the coding sequence. Following a phenol/chloroform extraction, the DNA is ethanol precipitated, washed in 70% ethanol, dried and resuspended in sterile water. The in vitro transcription reaction is performed by incubating the linearized DNA with transcription buffer (200 mM Tris-HCl, pH 8.0, 40 mM MgCl$_2$, 10 mM spermidine, 250 NaCl [T7 or T3] or 200 mM Tris-HCl, pH 7.5, 30 mM MgCl$_2$, 10 mM spermidine [SP6]), dithiothreitol, RNase inhibitors, each of the four ribonucleoside triphosphates, and either SP6, T7 or T3 RNA polymerase for 30 min at 37° C. To prepare a radiolabeled polynucleotide comprising RNA, unlabeled UTP will be omitted and $^{35}$S-UTP will be included in the reaction mixture. The DNA template is then removed by incubation with DNaseI. Following ethanol precipitation, an aliquot of the radiolabeled RNA is counted in a scintillation counter to determine the cpm/µl (Ausubel et al., supra).

Alternatively, nucleic acids comprising RNA are prepared by chemical synthesis techniques such as solid phase phosphoramidite (described above).

3. Nucleic Acids Comprising Oligonucleotides

A nucleic acid comprising oligonucleotides can be made by using oligonucleotide synthesizing machines which are commercially available (described above).

III. Detection Complex

The invention provides for a detection complex and therefore teaches methods of preparing a detection complex. The invention also provides a labeled detection complex and methods of preparing a labeled detection complex.

A probe comprising at least two subunits is used to prepare a detection complex according to one embodiment of the invention. A probe comprising at least two subunits and having a secondary structure that changes upon binding of the probe to the target nucleic acid sequence is also used to prepare a detection complex according to another embodiment of the invention. A probe according to the invention has a secondary structure as defined herein, (including a stem loop, a hairpin, an internal loop, a bulge loop, a branched structure and a pseudoknot) or multiple secondary structures, cloverleaf type structures or any three-dimensional structure, as defined hereinabove. Probes useful for forming a detection complex according to the invention include probes comprising covalently bound or non-covalently bound subunits (e.g., a bi-molecular or multi-molecular probe as defined herein).

A. Preparation of a Detection Complex

In one embodiment, a detection complex according to the invention is formed by incubating a) an upstream, preferably extendable 3' end, preferably an oligonucleotide primer, b) a probe comprising at least two oligonucleotide subunits, located not more than 5000 nucleotides downstream of the upstream primer and c) an appropriate target nucleic acid sequence wherein the target sequence is complementary to both the primer and the probe and d) a suitable buffer (for example Sentinel Molecular Beacon PCR core buffer (Catalog #600500) or 10× Pfu buffer available from Stratagene (Catalog #200536), under conditions that allow the nucleic acid sequence to hybridize to the primer and the probe (for example 95° C. for 2–5 minutes followed by cooling to between approximately 50–60° C.). The optimal temperature will vary depending on the specific probe(s), primers and, in certain embodiments, polymerases that are used.

In another embodiment, a detection complex according to the invention is formed by incubating a) an upstream, preferably extendable 3' end, preferably an oligonucleotide primer, b) a probe comprising at least two oligonucleotide subunits and having a secondary structure, as defined herein, that changes upon binding to the target nucleic acid, located not more than 5000 nucleotides downstream of the upstream primer and c) an appropriate target nucleic acid sequence wherein the target sequence is complementary to both the primer and the probe and d) a suitable buffer (for example Sentinel Molecular Beacon PCR core buffer (Catalog #600500) or 10× Pfu buffer available from Stratagene (Catalog #200536), under conditions that allow the nucleic acid sequence to hybridize to the primer and the probe (for example 95° C. for 2–5 minutes followed by cooling to between approximately 50–60° C.). The optimal temperature will vary depending on the specific probe(s), primers and, in certain embodiments, polymerases that are used.

Hybridization is performed at a binding temperature wherein the first subunit of the probe does not dissociate from at least the second subunit of the probe when not bound to the target nucleic acid sequence at or below the binding temperature.

According to one embodiment of this aspect of the invention, the 3' end of the upstream oligonucleotide primer is extended by the synthetic activity of a polymerase according to the invention such that the newly synthesized 3' end of the upstream oligonucleotide primer partially displaces at least a portion of a first subunit of the probe. Extension is preferably carried out in the presence of 1× Sentinel Molecular beacon core buffer or 1× Pfu buffer for 15 seconds at 72° C. Extension is performed at a polymerization temperature wherein the first subunit of the probe does not dissociate from the second subunit of the probe when not displaced by the extension product at or below the polymerization temperature. Displacement of at least a portion of a first subunit of the probe causes the first subunit of the probe to dissociate from a second subunit of the probe and be released.

In another embodiment of the invention, a detection complex according to the invention can be prepared by incubating a target nucleic acid sequence with a probe comprising at least two subunits such that the probe hybridizes with the target nucleic acid such that at least subunit of the probe dissociates from the remaining probe subunit(s). Annealing is preferably carried out under conditions that allow the nucleic acid sequence to hybridize to the oligonucleotide primer (for example 95° C. for 2–5 minutes followed by cooling to between approximately 50–60° C.) in the presence a suitable buffer (for example 1× Sentinel Molecular beacon core buffer or 1× Pfu buffer).

In another embodiment of the invention, a detection complex according to the invention can be prepared by incubating a target nucleic acid sequence with a probe comprising at least two subunits and having a secondary structure, as defined herein, that changes upon binding to the target nucleic acid, such that at least a portion of the first subunit of the probe anneals to the target nucleic acid sequence prior to the occurrence of a change in the secondary structure of the probe and dissociation of a subunit of the probe from the remaining probe subunit(s). Annealing is preferably carried out under conditions that allow the nucleic acid sequence to hybridize to the oligonucleotide primer (for example 95° C. for 2–5 minutes followed by cooling to between approximately 50–60° C.) in the presence a suitable buffer (for example 1× Sentinel Molecular beacon core buffer or 1× Pfu buffer).

Annealing is carried out at a binding temperature wherein the first subunit of the probe does not dissociate from the second subunit of the probe when not bound to the target nucleic acid sequence at or below the binding temperature.

B. How to Prepare a Labeled Detection Complex

In the present invention, a label is attached to a probe comprising two subunits. The invention also provides for a labeled detection complex comprising a probe, wherein the probe has two subunits a secondary structure, as defined herein, that changes upon binding to the target nucleic acid. Thus, the released subunit of the probe, which is released following dissociation of the first subunit of the probe from the second subunit of the probe can be detected.

In one embodiment, a labeled detection complex according to the invention is formed by incubating a) an upstream extendable 3' end, preferably an oligonucleotide primer, b) a labeled probe comprising two subunits, located not more than 5000 nucleotides downstream of the upstream primer and c) an appropriate target nucleic acid sequence wherein the target sequence is complementary to the oligonucleotides and d) a suitable buffer (for example 1× Sentinel Molecular beacon core buffer or 1× Pfu buffer), under conditions that allow the nucleic acid sequence to hybridize to the oligonucleotide primer and probe (for example 95° C. for 2–5 minutes followed by cooling to between approximately 50–60° C.). A labeled detection complex can also be formed by incubating a target nucleic acid with a probe comprising two subunits and having a secondary structure, as defined herein, that changes upon binding to the target nucleic acid. Hybridization is carried out at a binding temperature wherein the first subunit of the probe does not dissociate from the second subunit of the probe when not bound to the target nucleic acid sequence at or below the binding temperature. The 3' end of the upstream primer is extended by the synthetic activity of a polymerase such that the newly synthesized 3' end of the upstream primer partially displaces at least a portion of at least a first subunit of the probe. Extension is preferably carried out in the presence of 1× Sentinel Molecular beacon core buffer or 1× Pfu buffer for 15 seconds at 72° C. Extension is performed at a polymerization temperature wherein the first subunit of the probe does not dissociate from the target nucleic acid when not displaced by the primer extension product at or below the polymerization temperature.

In another embodiment, a labeled detection complex according to the invention can be prepared by incubating a target nucleic acid sequence with a labeled probe comprising two subunits. Annealing is preferably carried out under conditions that allow the nucleic acid sequence to hybridize to the probe (for example 95° C. for 2–5 minutes followed by cooling to between approximately 50–60° C.) in the presence a suitable buffer (for example 1× Sentinel Molecular beacon core buffer or 1× Pfu buffer). Annealing is carried out at a binding temperature wherein the first subunit of the probe does not dissociate from the second subunit of the probe when not bound to the target nucleic acid sequence at or below the binding temperature. A labeled detection complex according to the invention can also be prepared by incubating a target nucleic acid sequence with a labeled probe comprising two subunits and having a secondary structure, as defined herein, that changes upon binding to the target nucleic acid.

Subsequently, any of several strategies may be employed to distinguish the associated, labeled first subunit of the probe from the released, labeled first subunit of the probe.

The probe is labeled, as described below, by incorporating moieties detectable by spectroscopic, photochemical, biochemical, immunochemical, enzymatic or chemical means. The method of linking or conjugating the label to the probe depends, of course, on the type of label(s) used and the position of the label on the probe. A probe that is useful according to the invention can be labeled at the 5' end or the 3' end of a probe subunit. In one embodiment, at least one subunit of a probe is labeled throughout the length of the probe subunit.

A variety of labels are appropriate for use in the invention, as well as methods for their inclusion in the probe, are known in the art and include, but are not limited to, enzymes (e.g., alkaline phosphatase and horseradish peroxidase) and enzyme substrates, radioactive atoms, fluorescent dyes, chromophores, chemiluminescent labels, electrochemiluminescent labels, such as Origen™ (Igen), that may interact with each other to enhance, alter, or diminish a signal. Of course, if a labeled molecule is used in a PCR based assay carried out using a thermal cycler instrument, the label must be able to survive the temperature cycling required in this automated process.

Among radioactive atoms, $^{33}P$ or, $^{32}P$ is preferred. Methods for introducing $^{33}P$ or, $^{32}P$ into nucleic acids are known in the art, and include, for example, 5' labeling with a kinase, or random insertion by nick translation. "Specific binding partner" refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. The above description is not meant to categorize the various labels into distinct classes, as the same label may serve in several different modes. In certain embodiments, a specific binding partner is useful for labeling a probe or detecting a labeled probe. For example, $^{125}I$ may serve as a radioactive label or as an electron-dense reagent. HRP may serve as an enzyme or as antigen for a monoclonal antibody. Further, one may combine various labels for desired effect. For example, one might label a probe with biotin, and detect the presence of the probe with avidin labeled with $^{125}I$, or with an anti-biotin monoclonal antibody labeled with HRP. Other permutations and possibilities will be readily apparent to those of ordinary skill in the art and are considered as equivalents within the scope of the instant invention.

Fluorophores for use as labels in constructing labeled probes of the invention include rhodamine and derivatives (such as Texas Red), fluorescein and derivatives (such as 5-bromomethyl fluorescein), Lucifer Yellow, IAEDANS, 7-Me$_2$N-coumarin-4-acetate, 7-OH-4-CH$_3$-coumarin-3-acetate, 7-NH$_2$-4-CH$_3$-coumarin-3-acetate (AMCA), monobromobimane, pyrene trisulfonates, such as Cascade Blue, and monobromorimethyl-ammoniobimane. In general, fluorophores with wide Stokes shifts are preferred, to allow using fluorimeters with filters rather than a monochromometer and to increase the efficiency of detection.

Probes labeled with fluorophores can readily be used in the detection methods of the invention. If the label is on the 5'-end of the probe subunit, the released labeled first subunit of the probe is separated from the remaining, hybridized subunit(s) of the probe by procedures well known in the art. In another embodiment of the invention, detection of the released, labeled first subunit of the probe can be accomplished using, for example, fluorescence polarization, a technique to differentiate between large and small molecules based on molecular tumbling. Large molecules (i.e., intact labeled probe) tumble in solution much more slowly than small molecules. Upon linkage of a fluorescent moiety to an appropriate site on the molecule of interest, this fluorescent moiety can be measured (and differentiated) based on molecular tumbling, thus differentiating between intact probe and a released subunit of the probe. The fluorescence of the released label is then compared to the label remaining bound to the target.

In some situations, one can use two interactive labels (e.g., FRET or non-FRET pairs) on a single subunit of a probe with due consideration given for maintaining an appropriate spacing of the labels on the probe to permit the separation of the labels during probe unfolding (e.g., for example due to a change in the secondary structure of the probe), hydrolysis, or upon dissociation of a subunit labeled with one member of an interactive label pair from a second subunit labeled with a second member of an interactive label pair. In one embodiment, a first subunit of probe is labeled with one member of an interactive label pair and a second subunit is labeled with a second member of an interactive label pair. Preferred interactive labels useful according to the invention include, but are not limited to rhodamine and derivatives, fluorescein and derivatives, Texas Red, coumarin and derivatives, crystal violet and include, but are not limited to DABCYL, TAMRA and NTB (nitrothiazole blue) in addition to any of the FRET or non-FRET labels described herein.

The fluorescence of the released labeled probe subunit is then compared to the label remaining bound to the target. In one embodiment, the quencher is positioned such that the probe will not fluoresce when not hybridized to the target nucleic acid sequence. In another embodiment, the quencher is positioned such that the probe will not fluoresce when hybridized to the target nucleic acid sequence, prior to dissociation of a subunit of the probe. A dual labeled bi- or multi-molecular probe according to the invention will not fluoresce when the probe is not dissociated because the light emitted from the dye is quenched by the quencher. Thus, any fluorescence emitted by an intact probe is considered to be background fluorescence. Dissociation of the molecules comprising the probe results in an increase in fluorescence. The amount of fluorescence is proportional to the amount of nucleic acid target sequence present in a sample.

In yet another embodiment, two multisubunit, labeled probes are used, each complementary to separate regions of separate strands of a double-stranded target sequence, but not to each other, so that in embodiments that use a detection complex comprising a primer, a labeled nucleic acid anneals downstream of each primer. For example, the presence of two probes can potentially double the intensity of the signal generated from a single label and may further serve to reduce product strand reannealing, as often occurs during PCR amplification. In embodiments wherein a detection complex comprises a primer, in addition to the probe and target nucleic acid, the probes are selected so that the probes bind at positions adjacent (downstream) to the positions at which primers bind.

One can also use multiple probes in the present invention to achieve other benefits. For instance, one could test for any number of pathogens in a sample simply by putting as many probes as desired into the reaction mixture; the probes could each comprise a different label to facilitate detection.

One can also achieve allele-specific or species-specific discrimination using multiple probes in the present invention, for instance, by using probes that have different $T_m$s and conducting the annealing/polymerization reaction at a temperature specific for only one probe/allele duplex. One can also achieve allele specific discrimination by using only a single probe and examining the released probe subunits. In one embodiment of the invention, the probe is designed to be exactly complementary, for example, at least in the 5' terminal region, to one allele but not to the other allele(s). With respect to the other allele(s), the probe will be mismatched in the 5' terminal region of the probe so that a different subunit of a probe will be released as compared to the subunit of the probe that is released when the probe is hybridized to the exactly complementary allele. In another embodiment of the invention, one can achieve allele discrimination by designing the upstream primer such that it detects the allele. If there is a target nucleic acid sequence that is a perfect match to the upstream primer, than the upstream primer will be extended and will displace a subunit of the probe. If the target nucleic acid sequence is not a perfect match to the upstream primer, the upstream primer will not be extended and will not displace a subunit of the probe.

Although probe sequence can be selected to achieve important benefits, one can also realize important advantages by selection of probe labels(s). The labels may be attached to the probe subunit(s) directly or indirectly by a variety of techniques. Depending on the precise type of label used, the label can be located at the 5' or 3' end of the probe subunit, located internally in the probe subunit, or attached to spacer arms of various sizes and compositions to facilitate signal interactions. Using commercially available phosphoramidite reagents, one can produce oligomers containing functional groups (e.g., thiols or primary amines) at either the 5' or the 3' terminus via an appropriately protected phosphoramidite, and can label them using protocols described in, for example, PCR Protocols: A Guide to Methods and Applications, Innis et al., eds. Academic Press, Ind., 1990.

Methods for introducing oligonucleotide functionalizing reagents to introduce one or more sulfhydryl, amino or hydroxyl moieties into the probe subunit sequence, typically at the 5' terminus, are described in U.S. Pat. No. 4,914,210.

A 5' phosphate group can be introduced as a radioisotope by using polynucleotide kinase and gamma-$^{32}$P-ATP or gamma-$^{33}$P-ATP to provide a reporter group. Biotin can be added to the 5' end by reacting an aminothymidine residue, or a 6-amino hexyl residue, introduced during synthesis, with an N-hydroxysuccinimide ester of biotin. Labels at the 3' terminus may employ polynucleotide terminal transferase to add the desired moiety, such as for example, cordycepin $^{35}$S-dATP, and biotinylated dUTP.

Oligonucleotide derivatives are also available labels. For example, etheno-dA and etheno-A are known fluorescent adenine nucleotides that can be incorporated into a nucleic acid probe subunit. Similarly, etheno-dC or 2-amino purine deoxyriboside is another analog that could be used in probe subunit synthesis. The probes containing such nucleotide derivatives may be dissociated to release much more strongly fluorescent mononucleotides.

C. Detection of Released Labeled Probe Subunits

Detection or verification of the released, labeled probe subunit(s) may be accomplished by a variety of methods well known in the art and may be dependent on the characteristics of the labeled moiety or moieties comprising a labeled detection complex.

IV. Determining the Stability of the Secondary Structure of a Probe

A. Melting Temperature Assay

A melting temperature assay, takes advantage of the different absorption properties of double stranded and single stranded DNA, that is, double stranded DNA (the double stranded DNA being that portion of a nucleic acid sequence that has folded back on itself to generate an antiparallel duplex structure wherein complementary sequences (base pairs) are associated via hydrogen bonding) absorbs less light than single stranded DNA at a wavelength of 260 nm, as determined by spectrophotometric measurement.

Figure 8A:
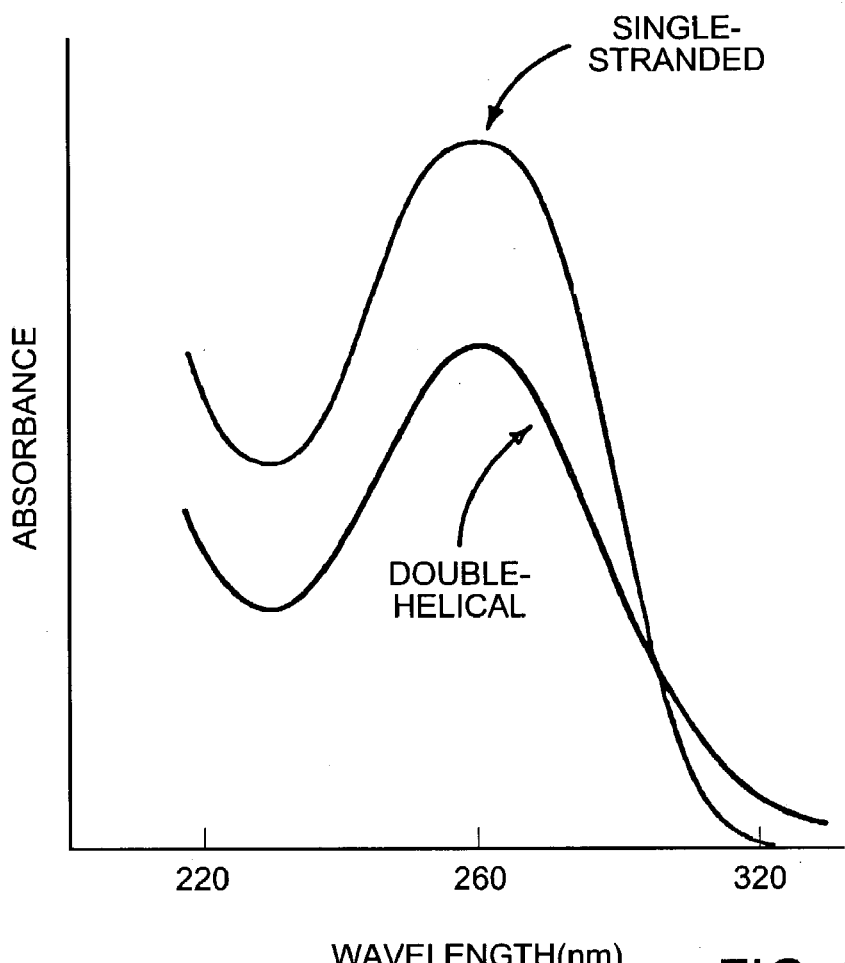
FIG. 8a is a graph demonstrating the difference in light absorbance of double-stranded versus single-stranded DNA.
Figure 8B:
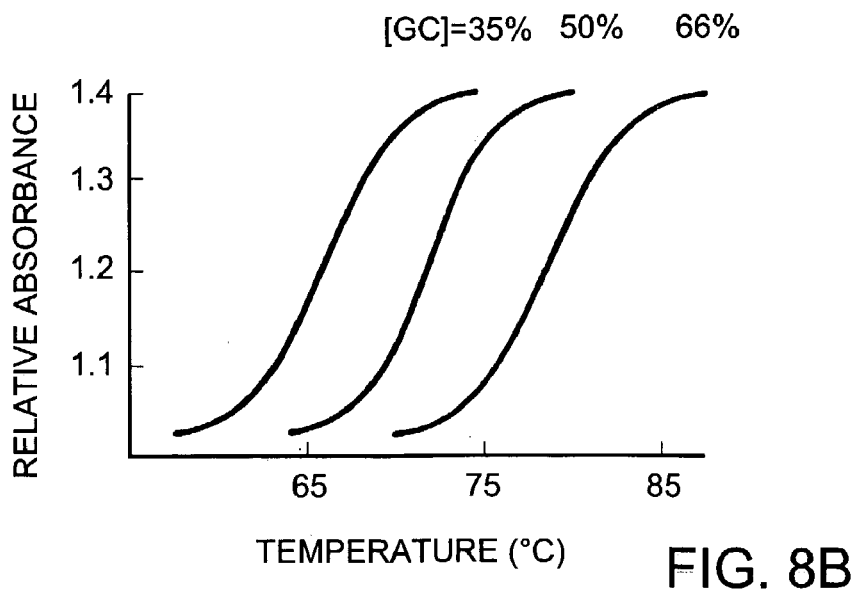
FIG. 8b is a graph demonstrating DNA melting curves.
Figure 8C:
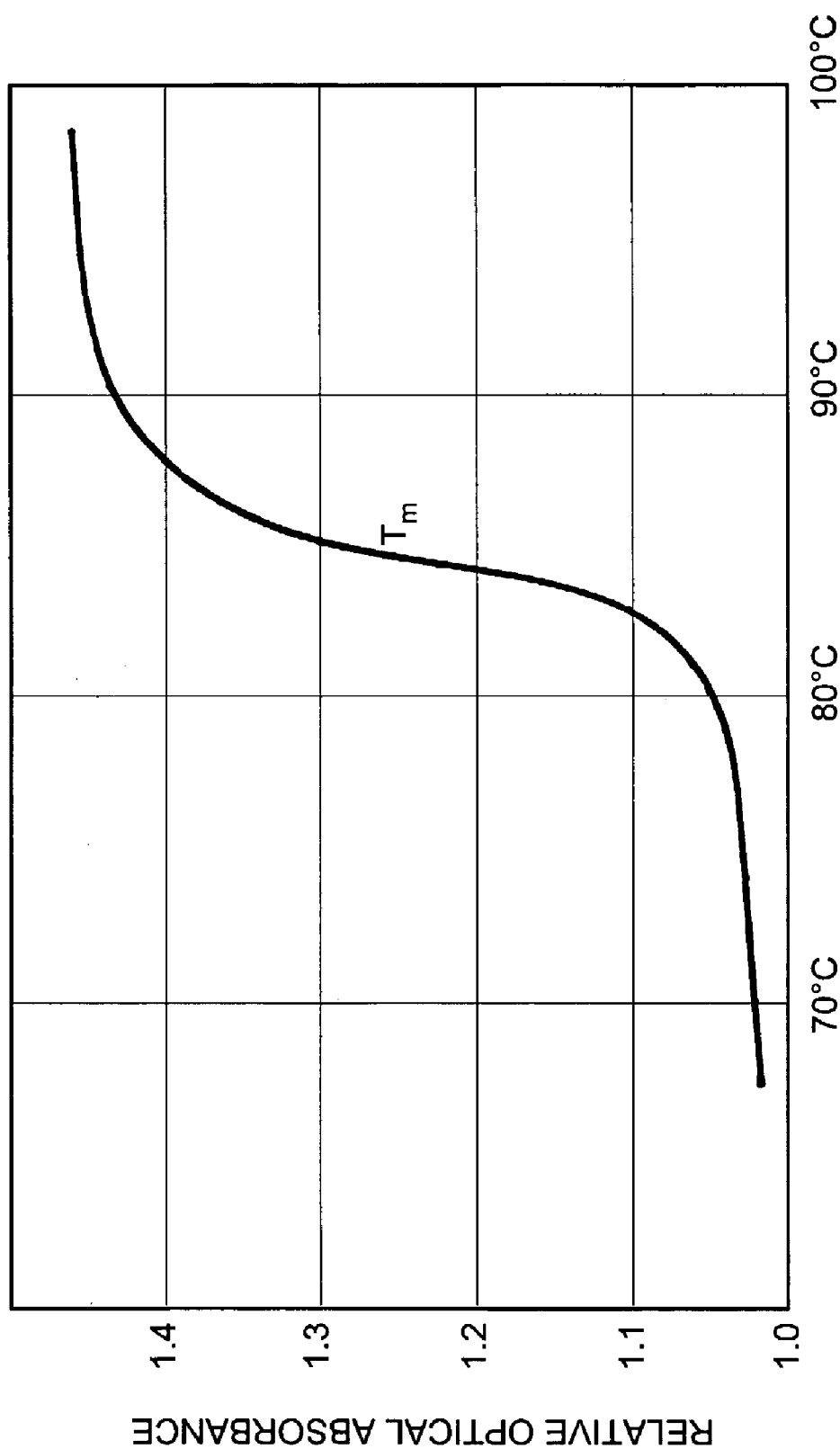
FIG. 8c is a graph demonstrating the effects of temperature on the relative optical absorbance of DNA.

The denaturation of DNA occurs over a narrow temperature range and results in striking changes in many of the physical properties of DNA. A particularly useful change occurs in optical density. The heterocyclic rings of nucleotides adsorb light strongly in the ultraviolet range (with a maximum close to 260 nm that is characteristic for each base). However, the adsorption of DNA is approximately 40% less than would be displayed by a mixture of free nucleotides of the same composition. This effect is called hyperchromism and results from interactions between the electron systems of the bases, made possible by their stacking in the parallel array of the double helix. Any departure from the duplex state is immediately reflected by a decline in this effect (that is, by an increase in optical density toward the value characteristic of free bases (FIG. 8a). The denaturation of double stranded DNA can therefore be followed by this hyperchromicity (FIGS. 8b and 8c)

The midpoint of the temperature range over which the strands of DNA separate is called the melting temperature, denoted $T_m$. An example of a melting curve determined by change in optical absorbance is shown in FIG. 8c. The curve always takes the same form, but its absolute position on the temperature scale (that is, its $T_m$) is influenced by both the base composition of the DNA and the conditions employed for denaturation.

The melting temperature of a DNA molecule depends markedly on its base composition. DNA molecules rich in GC base pairs have a higher Tm than those having an abundance of AT base pairs (FIG. 8b). The Tm of DNA from many species varies linearly with GC content, rising from 77° to 100° C. as the fraction of GC pairs increases from 20% to 78%. That is, the dependence of $T_m$ on base composition is linear, increasing about 0.4° C. for every percent increase in G-C content. GC base pairs are more stable than AT pairs because their bases are held together by three hydrogen bonds rather than by two. In addition, adjacent GC base pairs interact more strongly with one another than do adjacent AT base pairs. Hence, the AT-rich regions of DNA are the first to melt.

A major effect on $T_m$ is exerted by the ionic strength of the solution. The $T_m$ increases 16.6° C. for every tenfold increase in monovalent cation concentration. The most commonly used condition is to perform manipulations of DNA in 0.12 M phosphate buffer, which provides a monovalent Na+ concentration of 0.18M, and a $T_m$ of the order of 90° C.

The $T_m$ can be greatly varied by performing the reaction in the presence of reagents, such as formamide, that destabilize hydrogen bonds. This allows the $T_m$ to be reduced to as low as 40° C. with the advantage that the DNA does not suffer damage (such as strand breakage) that can result from exposure to high temperatures. (Stryer, *Biochemistry*, 1998, 3$^{rd}$ Edition, W. H. Freeman and Co., pp. 81–82 and Lewin, Genes II, 1985, John Wiley & Sons, p.63–64).

The stability of the secondary structure of the probe according to the invention is determined in a melting temperature assay as follows.

A standard curve for the probe (for example FIG. 8c), wherein absorbance is plotted versus temperature, is prepared by incubating a sample comprising from about 0.2 µg/ml to 100 µg/ml of the probe in a buffer which allows for denaturing and reannealing of the probe or a subunit of the probe, at various temperatures and for a time sufficient to permit denaturing and reannealing of the probe, and measuring the absorbance of a sample in a quartz cuvette (with a pathlength appropriate for the spectrophotometer being used, e.g., 1-cm), in a spectrophotometer over a range of temperatures wherein the lower temperature limit of the range is at least 50° C. below, and the upper temperature limit of the range is at least 50° C. above the Tm or predicted Tm of the probe. The Tm of the probe is predicted based on the base pair composition according to methods well known in the art (see, Sambrook, supra; Ausubel, supra). Standard curves are generated and compared, using a variety of buffers (e.g., 1× TNE buffer (10×-0.1M Tris base, 10 mM EDTA, 2.0 M NaCl , pH 7.4), 1× Cloned Pfu buffer, described herein, 1× Sentinel Molecular beacon buffer, described herein) including a buffer that is possible and preferentially optimal, in certain embodiments, for the polymerase to be used in the polymerization reaction. The pH of the buffer will be monitored as the temperature increases, and adjusted as is needed.

The assay is performed in a single-beam ultraviolet to visible range (UV-VIS) spectrophotometer. Preferably, the assay is performed in a double-beam spectrophotometer to simplify measurements by automatically comparing the cuvette holding the sample solution to a reference cuvette (matched cuvette) that contains the blank. The blank is an equal volume of sample buffer.

The temperature of the spectrophotometer can be controlled such that the absorbance of the sample is measured at specific temperatures. Spectrophotometers useful according to the invention include but are not limited to the Beckman Coulter DU® 600/7000 Spectrophotometers in combination with the MicroTm Analysis Accessory (Beckman Coulter, Inc., Columbia, Md.).

Figure 8D:
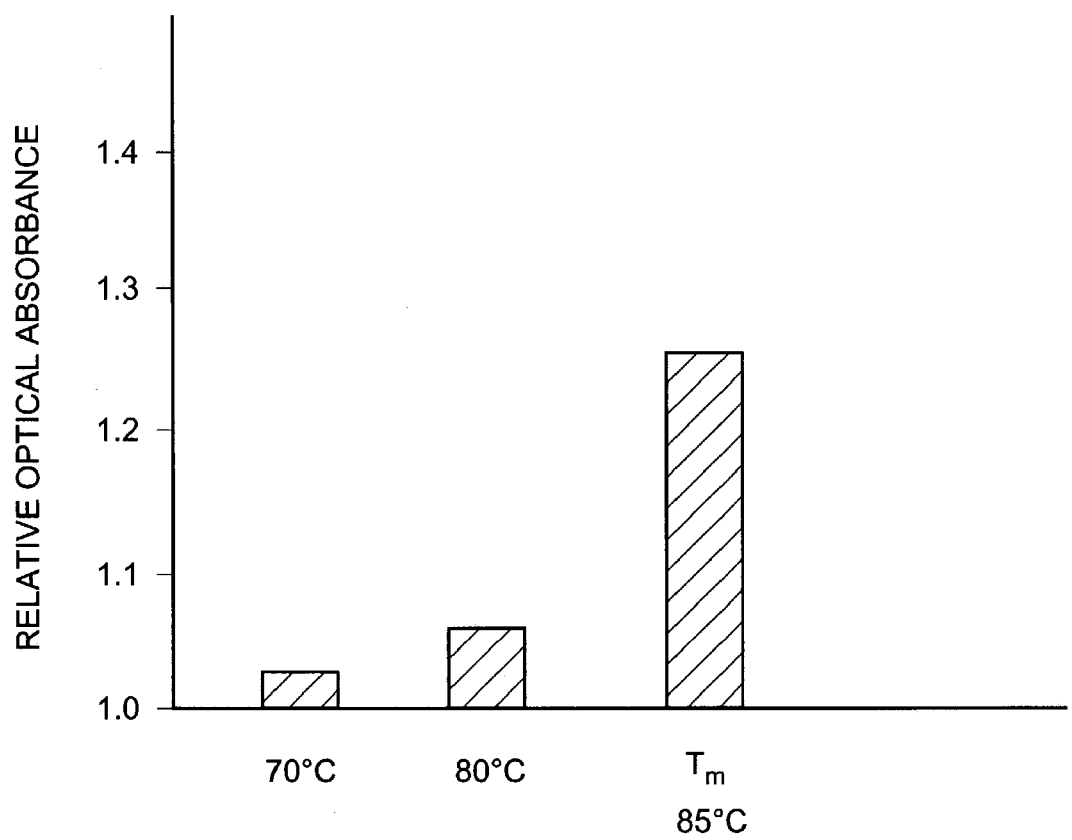
FIG. 8d is a graph demonstrating the effects of temperature on the relative optical absorbance of DNA.

The stability of the secondary structure of a probe at a particular temperature and in a buffer that is possible and preferentially optimal for the formation of a detection complex according to the invention and/or for the nucleic acid polymerization activity to be employed in certain embodiments of the invention, is determined by measuring the absorbance of the probe at a particular temperature, as above, and determining if the value of the absorbance is less than the absorbance at the Tm, as determined from the standard curve, wherein the standard curve is generated using either the same buffer as used at the test temperature, or a buffer known to produce a comparable standard curve, as described above. The secondary structure of the probe is "stable" in a melting temperature assay, at a temperature that is at or below the temperature of the binding reaction (i.e., at which binding is performed) if the level of light absorbance at the temperature at or below the temperature of the binding reaction is less (i.e., at least 5%, preferably 20% and most preferably 25% or more) than the level of light absorbance at a temperature that is equal to the Tm of the probe (see FIGS. 8c and 8d).

B. FRET

A FRET assay is useful in the invention for two purposes. The first is to determine whether the secondary structure of a probe is "stable" as defined herein. The second is to determine whether the secondary structure of the probe has undergone a "change" upon binding of the probe to the target nucleic acid.

"FRET" is a distance-dependent interaction between the electronic excited states of two dye molecules in which excitation is transferred from a donor molecule to an acceptor molecule. FRET is caused by a change in the distance separating a fluorescent donor group from an interacting resonance energy acceptor, either another fluorophore, a chromophore, or a quencher. Combinations of donor and acceptor moieties are known as "FRET pairs". Efficient FRET interactions require that the absorption and emission spectra of the dye pairs have a high degree of overlap.

In most embodiments, the donor and acceptor dyes for FRET are different, in which case FRET can be detected by the appearance of sensitized fluorescence of the acceptor and/or by quenching of donor fluorescence. When the donor and acceptor are the same, FRET is detected by the resulting fluorescence depolarization. FRET is dependent on the inverse sixth power of the intermolecular separation (Stryer et al., 1978, *Ann. Rev. Biochem.*, 47:819; Selvin, 1995, *Methods Enzymol.*, 246:300).

As used herein, the term "donor" refers to a fluorophore which absorbs at a first wavelength and emits at a second, longer wavelength. The term "acceptor" refers to a fluorophore, chromophore or quencher with an absorption spectrum which overlaps the donor's emission spectrum and is able to absorb some or most of the emitted energy from the donor when it is near the donor group (typically between 1–100 nm). If the acceptor is a fluorophore capable of exhibiting FRET, it then re-emits at a third, still longer wavelength; if it is a chromophore or quencher, then it releases the energy absorbed from the donor without emitting a photon. Although the acceptor's absorption spectrum overlaps the donor's emission spectrum when the two groups are in proximity, this need not be the case for the spectra of the molecules when free in solution. Acceptors thus include fluorophores, chromophores or quenchers which exhibit either FRET or quenching when placed in proximity, on a probe according to the invention, to the donor due to the presence of a probe secondary structure that changes upon binding of the probe to the target nucleic acid, as defined herein, or upon dissociation of a first probe subunit from at least a second probe subunit. Acceptors do not include fluorophores, chromophores or quenchers that exhibit FRET or quenching a) at temperatures equal to or greater than the Tm of the probe (e.g. more than 5° above the Tm, for example 6°, 10°, 25°, 50° or more above the Tm) or b) in the presence of a target nucleic acid.

Reference herein to "fluorescence" or "fluorescent groups" or "fluorophores" include luminescence, luminescent groups and suitable chromophores, respectively. Suitable luminescent probes include, but are not limited to, the luminescent ions of europium and terbium introduced as lanthium chelates (Heyduk & Heyduk, 1997). The lanthanide ions are also good donors for energy transfer to fluorescent groups (Selvin 1995). Luminescent groups containing lanthanide ions can be incorporated into nucleic acids utilizing an 'open cage' chelator phosphoramidite.

As used herein, the term "quenching" refers to the transfer of energy from donor to acceptor which is associated with a reduction of the intensity of the fluorescence exhibited by the donor.

The donor and acceptor groups may independently be selected from suitable fluorescent groups, chromophores and quenching groups. Donors and acceptors useful according to the invention include but are not limited to: 5-FAM (also called 5-carboxyfluorescein; also called Spiro(isobenzofuran-1(3H), 9'-(9H)xanthene)-5-carboxylic acid, 3',6'-dihydroxy-3-oxo-6-carboxyfluorescein); 5-Hexachloro-Fluorescein ([4,7,2',4',5',7'-hexachloro-(3',6'-dipivaloylfluoresceinyl)-6-carboxylic acid]); 6-Hexachloro-Fluorescein ([4,7,2',4',5',7'-hexachloro-(3',6'-dipivaloylfluoresceinyl)-5-carboxylic acid]); 5-Tetrachloro-Fluorescein ([4,7,2',7'-tetra-chloro-(3',6'-dipivaloylfluoresceinyl)-5-carboxylic acid]); 6-Tetrachloro-Fluorescein ([4,7,2',7'-tetrachloro-(3',6'-dipivaloylfluoresceinyl)-6-carboxylic acid]); 5-TAMRA (5-carboxytetramethylrhodamine; Xanthylium, 9-(2,4-dicarboxyphenyl)-3,6-bis(dimethyl-amino); 6-TAMRA (6-carboxytetramethylrhodamine; Xanthylium, 9-(2,5-dicarboxyphenyl)-3, 6-bis(dimethylamino); EDANS (5-((2-aminoethyl) amino)naphthalene-1-sulfonic acid); 1,5-IAEDANS (5-((((2-iodoacetyl)amino)ethyl)amino) naphthalene-1-sulfonic acid); DABCYL (4-((4-(dimethylamino)phenyl)azo)benzoic acid) Cy5 (Indodicarbocyanine-5) Cy3 (Indo-dicarbocyanine-3); and BODIPY FL (2,6-dibromo-4,4-difluoro-5,7-dimethyl-4-bora- 3a,4a-diaza-s-indacene-3-proprionic acid), as well as suitable derivatives thereof.

In certain embodiments of the invention, a probe may also be labeled with two chromophores, and a change in the absorption spectra of the label pair is used as a detection signal, as an alternative to measuring a change in fluorescence.

In the method of the invention, fluorescence intensity of the-probe is measured at one or more wavelengths with a fluorescence spectrophotometer or microtitre plate reader, according to methods known in the art.

C. Fluorescence Quenching Assay

A fluorescence quenching assay is useful in the invention for two purposes. The first is to determine whether the secondary structure of a probe is "stable" as defined herein. The second is to determine whether the secondary structure of the probe has undergone a "change" upon binding of the probe to the target nucleic acid.

A probe or a probe subunit according to the invention is labeled with a pair of interactive labels (e.g., a FRET or non-FRET pair) wherein one member of the pair is a fluorophore and the other member of the pair is a quencher. For example, a probe according to the invention is labeled with a fluorophore and a quencher and fluorescence is measured in the absence of a target nucleic acid, over a range of temperatures, e.g., wherein the lower temperature limit of the range is at least 50° Celsius below, and the upper temperature limit of the range is at least 50° Celsius above the Tm or the predicted Tm of the probe.

D. Stability

The "stability" of the secondary structure of a probe according to the invention is determined as follows. A probe is labeled with a pair of interactive labels (for example, tetramethylrhodamine and DABCYL, or any of the interactive labels (either FRET or non-FRET pairs) described herein), according to methods well known in the art (for example as described in Glazer and Mathies, 1997, Curr. Opin. Biotechnol., 8:94; Ju et al., 1995, Analytical Biochem., 231:131). The location of the interactive labels on the probe is such that the labels are separated when the first subunit of a probe dissociates from a second subunit of a probe.

Figure 8E:
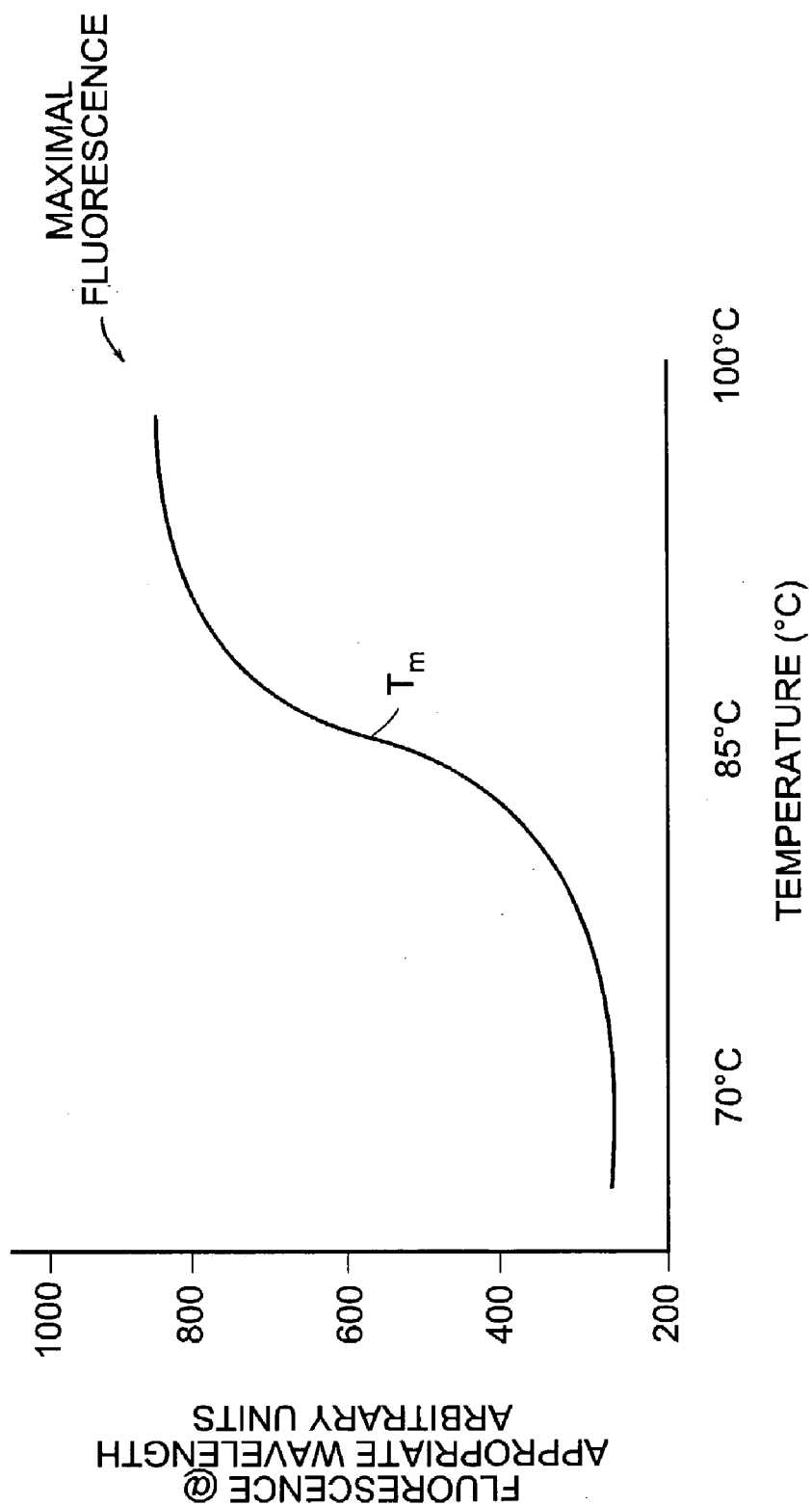
FIG. 8e is a graph demonstrating the effects of temperature on the fluorescence of DNA labeled with a pair of interactive labels.

A standard curve for the probe (for example FIG. 8e), wherein fluorescence is plotted versus temperature, is prepared by incubating a sample comprising typically 125 nM probe in 1× Melting Buffer (20 mM Tris-HCl, pH 8.0, 1 mM $MgCl_2$) or alternatively, in 5 mM Tris-HCl, pH 8.0, 0.1 mM EDTA, or other appropriate buffers for a time that is sufficient to permit denaturing and reannealing of the probe (typically the standard curve is generated using a fluorometer or spectrometer that undergoes a 1° C. per minute change) and measuring the fluorescence in a fluorometer or scanning fluorescence spectrophotometer over a range of temperatures wherein the lower temperature limit of the range is at least 50° C. below, and the upper temperature limit of the range is at least 50° C. above the Tm or predicted Tm of the probe. The Tm of the probe is predicted based on the base pair composition according to methods well known in the art (see, Sambrook, supra; Ausubel, supra).

Standard curves are generated and compared, using a variety of buffers (e.g., 1× TNE buffer (10×- 0.1M Tris base, 10 mM EDTA, 2.0 M NaCl , pH 7.4), 1× Cloned Pfu buffer, described herein, 1× Sentinel Molecular beacon buffer, described herein) including a buffer that is possible and preferentially optimal for the formation of a detection complex according to the invention and/or for the activity of the polymerization activity to be employed. The pH of the buffer will be monitored as the temperature increases, and adjusted as is needed.

The temperature of the fluorometer or spectrophotometer can be controlled such that the fluorescence of the sample is measured at specific temperatures. Fluorescence can be measured for example with a Perkin-Elmer LS50B Luminescence Spectrometer in combination with a temperature regulatable water bath (e.g., for example available from Fisher Scientific).

Figure 8F:
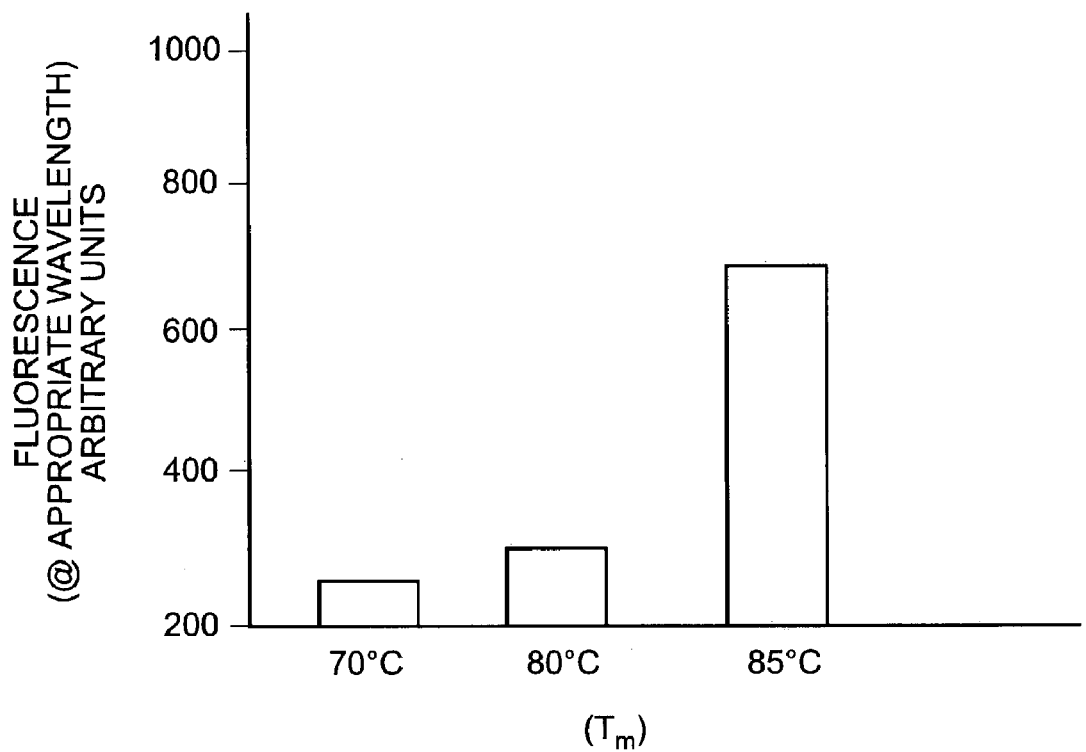
FIG. 8f is a graph demonstrating the effects of temperature on the fluorescence of DNA labeled with a pair of interactive labels.

The stability of the secondary structure of a probe at a particular temperature is determined by measuring the fluorescence of the probe at a particular temperature, as above, and determining if the value of the fluorescence is less than the fluorescence at the Tm, as determined from the standard curve. The secondary structure of the probe is "stable" in a FRET assay, at a temperature that is at or below the temperature of the binding reaction (i.e., at which binding is performed) if the level of fluorescence at the temperature at or below the temperature of the binding reaction is altered (i.e., at least 5%, preferably 20% and most preferably 25% more or less than) as compared to the level of fluorescence at a temperature that is equal to the Tm of the probe. The secondary structure of the probe is "stable" in a fluorescence quenching assay, at a temperature that is at or below the temperature of the binding reaction (i.e., at which binding is performed) if the level of fluorescence at the temperature at or below the temperature of the binding reaction is altered (i.e., at least 5%, preferably 20% and most preferably 25% more or less than) as compared to the level of fluorescence at a temperature that is equal to the Tm of the probe (see FIGS. 8f and 8g).

Alternatively, the stability of the secondary structure of the probe is determined by modifying the method of Gelfand et al. (1999, *Proc. Natl. Acad. Sci. USA*, 96:6113), incorporated herein by reference, to determine the fluorescence of a probe labeled with a pair of interactive labels over a range of temperatures, as described hereinabove.

V. Detecting a Secondary Structure

A secondary structure according to the invention is detected by generating a standard curve of fluorescence versus temperature for a probe comprising a pair of interactive labels in a FRET or a fluorescence quenching assay, as described above (see FIG. 8e). A probe that exhibits a change in fluorescence that correlates with a change in temperature (see FIG. 8e) (e.g., fluorescence increases as the temperature of the FRET reaction is increased) is capable of forming a secondary structure.

VI. Measuring a Change in Secondary Structure

A "change" in secondary structure according to the invention is detected by analyzing a probe comprising a pair of interactive labels in a FRET or fluorescence quenching assay at a particular temperature below the Tm of the probe, (e.g., the binding temperature and/or the polymerization temperature), as described above, in the presence or absence of 100 nM to 10 μM of a target nucleic acid sequence (typically the target nucleic acid sequence is in a 2–4 molar excess over the probe concentration, i.e., 250–500 nM target nucleic acid sequence is used).

Alternatively, a change in the secondary structure of the probe is determined by modifying the method of Gelfand et al. (1999, *Proc. Natl. Acad. Sci. USA*, 96:6113), incorporated herein by reference, to determine the fluorescence of a probe labeled with a pair of interactive labels in the presence or absence of a target nucleic acid as described hereinabove.

Figure 8G:
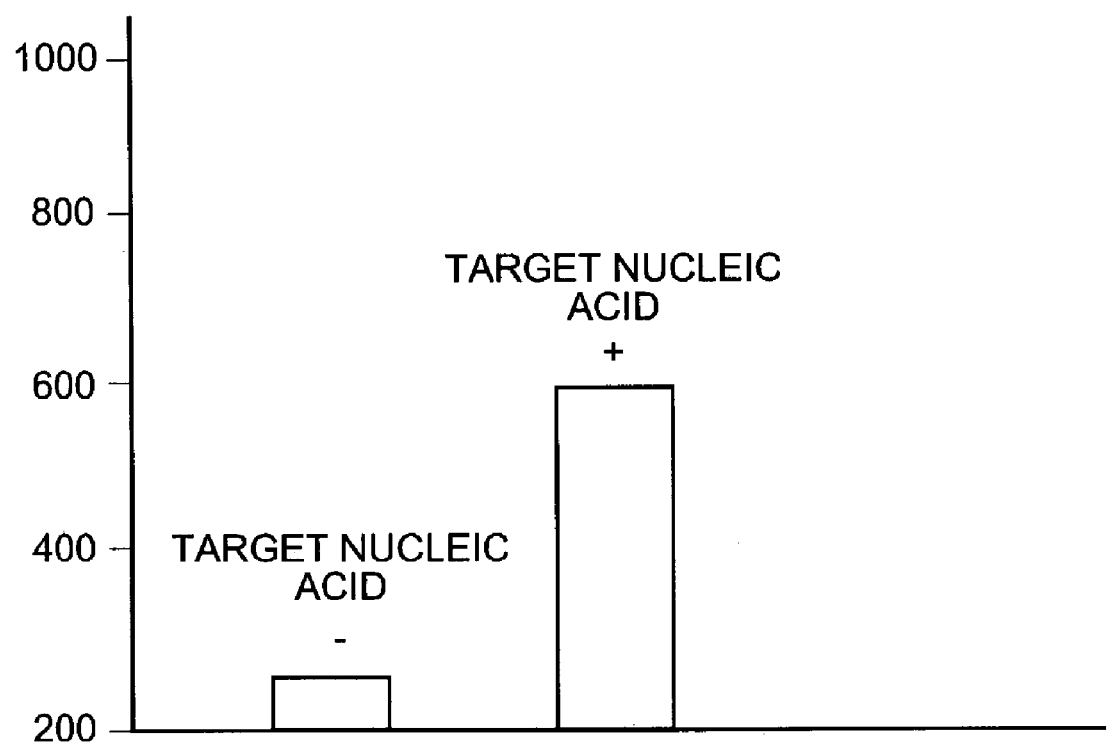
FIG. 8g is a graph demonstrating the effects of a target nucleic acid on the fluorescence of DNA labeled with a pair of interactive labels.

A "change" in secondary structure that occurs when a probe according to the invention binds to a target nucleic acid, is measured as an increase in fluorescence, such that the level of fluorescence after binding of the probe to the target nucleic acid at the temperature below the Tm of the probe, is greater than (e.g., at least 5%, preferably 5–20% and more preferably 25 or more) the level of fluorescence observed in the absence of a target nucleic acid sequence (see FIG. 8g).

VII. Methods of Use

The invention provides for a method of generating a signal indicative of the presence of a target nucleic acid sequence in a sample comprising the steps of forming a labeled detection complex by incubating a target nucleic acid sequence with a probe comprising at least two subunits, wherein a first subunit of the probe dissociates from a second subunit of the probe to generate a signal. The method of the invention can be used in a PCR based assay as described below.

A labeled detection complex comprising a labeled probe according to the invention and a target nucleic acid sequence is formed as described above in the section entitled "Detection Complex". Briefly, a detection complex is formed and incubated in the presence of amplification primers specific for the target nucleic acid sequence, a nucleic acid polymerase and an appropriate buffer (for example 10× Pfu buffer, Stratagene, Catalog #200536) in a PCR reaction with the following thermocycling parameters: 95° C. for 2 minutes and 40 cycles of 95° C. for 15 sec (denaturation step), 60° C. for 60 sec (annealing step) and 72° C. for 15 sec (extension step). During this reaction the target nucleic acid sequence is amplified and a first subunit of the probe is released to generate a detectable signal.

In another embodiment, a labeled detection complex comprising an upstream oligonucleotide primer, a labeled downstream probe according to the invention and a target nucleic acid sequence is formed as described above in the section entitled "Detection Complex". Briefly, a detection complex is formed and incubated in the presence of amplification primers specific for the target nucleic acid sequence, a nucleic acid polymerase and an appropriate buffer (for example 10× Pfu buffer, Stratagene, Catalog #200536) in a PCR reaction with the following thermocycling parameters: 95° C. for 2 minutes and 40 cycles of 95° C. for 15 sec (denaturation step), 60° C. for 60 sec (annealing step)and 72° C. for 15 sec (extension step). During this reaction, the target nucleic acid sequence is amplified and the upstream oligonucleotide is extended such that the extension product displaces at least a portion of the first subunit of the probe from the target nucleic acid. As a result of this displacement, the first subunit of the probe dissociates from at least a second subunit of the probe to generate a detectable signal.

The methods of the invention can also be used in non-PCR based applications to detect a target nucleic acid sequence, where such target may be immobilized on a solid support. Methods of immobilizing a nucleic acid sequence on a solid support are known in the art and are described in Ausubel F M et al. Current Protocols in Molecular Biology, John Wiley and Sons, Inc. and in protocols provided by the manufacturers, e.g., for membranes: Pall Corporation, Schleicher & Schuell, for magnetic beads: Dynal, for culture plates: Costar, Nalgenunc, and for other supports useful according to the invention, CPG, Inc. A solid support useful according to the invention includes but is not limited to silica based matrices, membrane based matrices and beads comprising surfaces including, but not limited to styrene, latex or silica based materials and other polymers. Magnetic beads are also useful according to the invention. Solid supports can be obtained from the above manufacturers and other known manufacturers.

The invention also provides for a non-PCR based assay for detecting a target nucleic acid sequence in solution. The method of the invention can be used to detect naturally occurring target nucleic acid sequences in solution including but not limited to RNA and DNA that is isolated and purified from cells, tissues, single cell organisms, bacteria or viruses. The method of the invention can also be used to detect synthetic targets in solution, including but not limited to RNA or DNA oligonucleotides, and peptide nucleic acids (PNAs). Non-PCR assays include but are not limited to detection assays involving isothermal linear or exponential amplification, where the amount of nucleic acid synthesized by the 3'–5' synthetic activity increases linearly or exponentially. One such example utilizes rolling circle amplification.

In one embodiment of the invention, detection of a nucleic acid target sequence that is either immobilized or in solution can be performed by incubating an immobilized nucleic acid target sequence or a target nucleic acid sequence in solution with an upstream oligonucleotide primer that is complementary to the target nucleic acid sequence and a downstream probe as defined herein, that is complementary to the target nucleic acid sequence, and a nucleic acid polymerase that possesses or lacks 5' to 3' exonuclease activity. A subunit of the probe is either end labeled at the 5' or 3' end, or is labeled internally. A downstream probe comprising a secondary structure, as defined herein, (including a stem loop, a hairpin, an internal loop, a bulge loop, a branched structure and a pseudoknot) or multiple secondary structures, cloverleaf structures, or any three dimensional structure, as defined herein, can be used. Detection of a released labeled, subunit of a probe involves isotopic, enzymatic, or colorimetric methods appropriate for the specific label that has been incorporated into the probe. Labels useful according to the invention and methods for the detection of labels useful according to the invention are described in the section entitled "Detection Complex". Alternatively, the probe further comprises a pair of interactive signal generating labeled moieties (for example a dye and a quencher) that are positioned such that when the probe is intact (i.e., a first subunit of the probe is not dissociated from at least a second subunit of the probe), the generation of a detectable signal is quenched. In another embodiment, the probe further comprises a pair of interactive signal generating labeled moieties (for example a dye and a quencher) that are positioned such that when the probe is not hybridized to the target nucleic acid, the generation of a detectable signal is quenched. Upon dissociation of the first subunit of the probe from at least a second subunit of the probe, the two signal generating moieties are separated from each other and a detectable signal is produced. Nucleic acid polymerases that are useful for detecting an immobilized nucleic acid target sequence or a nucleic acid target sequence in solution according to the method of the invention include mesophilic, thermophilic or hyper-thermophilic DNA polymerases lacking 5' to 3' exonucleolytic activity (described in the section entitled, "Nucleic Acid Polymerases)". Any nucleic acid polymerase that has 5' to 3' exonuclease activity is also useful according to the invention.

According to this non-PCR based method, the amount of a target nucleic acid sequence that can be detected is preferably about 1 pg to 1 μg, more preferably about 1 pg to 10 ng and most preferably about 1 pg to 10 pg. Alternatively, this non-PCR based method can measure or detect preferably about 1 molecule to $10^{20}$ molecules, more preferably about 100 molecules to $10^{17}$ molecules and more preferably about 100 molecules to $10^{17}$ molecules and most preferably 1000 molecules to $10^{14}$ molecules.

The invention also provides for a method of detecting a target nucleic acid sequence in a sample wherein a detection complex is formed as described in the section entitled, "Detection Complex", and the target nucleic acid sequence is amplified by a non-PCR based method including but not limited to an isothermal method, for example rolling circle, Self-sustained Sequence Replication Amplification (3SR), Transcription based amplification system (TAS), and Strand Displacement Amplification (SDA) and a non-isothermal method, for example Ligation chain reaction (LCR).

In the amplification protocols described below, samples which need to be prepared in order to quantify the target include: samples, no-template controls, and reactions for preparation of a standard curve (containing dilutions over the range of six orders of magnitude of a solution with a defined quantity of target).

Strand Displacement Amplification (SDA) is based on the ability of a restriction enzyme to nick the unmodified strand of a hemiphosphorothioate form of its recognition site. The appropriate DNA polymerase will initiate replication at this nick and displace the downstream non-template strand (Walker, 1992, *Proc. Natl. Acad. Sci. USA,* 89: 392, and PCR Methods and Applications 3: 1–6, 1993). The polymerases (Bca and Bst) which are used according to the method of SDA can also be used according to the invention.

In one embodiment, a subunit of a probe is a molecular beacon (MB); a fluorogenic probe which forms a stem-loop structure in solution. Typically: 5'-fluorescent dye (e.g. FAM), attached to the 5'-stem region (5–7 nt), the loop region (complementary to the target, 20 to 30 nt), the 3'-stem region (complementary to the 5'-stem region), and the quencher (e.g. DABCYL). If no target is present, the MB forms its stem, which brings dye and quencher into close proximity, and therefore no fluorescence is emitted. When an MB binds to its target, the subunit of the probe comprising the MB is dissociated, the stem is opened, dye is spatially separated from the quencher, and therefore the probe emits fluorescence (Tyagi S and Kramer F R, Nature Biotechnology 14: 303–308 (1996) and U.S. Pat. No. 5,925,517).

Strand Displacement Amplification (SDA) is essentially performed as described by Spargo et al., Molecular and Cellular Probes 10: 247–256 (1996). The enzymes used include restriction endonuclease BsoBI (New England Biolabs), DNA polymerase 5'-exo- Bca (PanVera Corporation). The target is an insertion-like element (1S6110) found in the Mycobacterium tuberculosis (Mtb) genome. The primers used are B1: cgatcgagcaagcca (SEQ ID NO: 1), B2: cgagccgctcgctg (SEQ ID NO: 2), S1: accgcatcgaatgcat-gtctcgggtaaggcgtactcgacc (SEQ ID NO: 3) and S2: cgattc-cgctccagacttctcgggtgtactgagatcccct (SEQ ID NO: 4). The Mycobacterium tuberculosis genomic DNA is serially diluted in human placental DNA. SDA is performed in 50 μl samples containing 0 to 1000 Mtb genome equivalehts, 500 ng human placental DNA, 160 units BsoB1, 8 units of 5'-exo- Bca, 1.4 mM each dCTPalphaS, TTP, dGTP, dATP, 35 mM $K_2PO_4$, pH 7.6 0.1 mg/ml acetylated bovine serum albumin (BSA), 3 mM Tris-HCl, 10 mM $MgCl_2$, 11 mM NaCl, 0.3 mM DTT, 4 mM KCl, 4% glycerol, 0.008 mM EDTA, 500 nM primers S1 and S2 and 50 nM primers B1 and B2 (KCl, glycerol and EDTA are contributed by the BsoB1 storage solution). The samples (35 μl ) are heated in a boiling water bath for 3 minutes before the addition of BsoB1 and 5'-exo Bca (10.7 units/μl BsoB1 and 0.53 units/μl 5'-exo Bca in 15 μl of New England Biolabs Buffer 2 (20 mM Tris-HCl pH 7.9, 10 mM $MgCl_2$, 50 mM NaCi, 1 mM DTT). Incubation is at 60° C. for 15 minutes, followed by 5 minutes in a boiling water bath.

Five μl of each sample in duplicate are removed for detection. Each reaction contains 1× Cloned Pfu buffer, 3.0 mM $MgCl_2$, 200 uM of each dNTP, 5 units Pfu, 300 nM each upstream primer: aaggcgtactcgacctgaaa (SEQ ID NO: 5) and fluorogenic probe (for example FAM-DABCYL): accatacg-gatagggatctc (SEQ ID NO: 6). The reactions are subjected to one cycle in a thermal cycler: 2 minutes at 95° C., 1 minute at 55° C., 1 minute at 72° C. The fluorescence is then determined in a fluorescence plate reader, such as Stratagene's FluorTracker or PE Biosystems' 7700 Sequence Detection System in Plate-Read Mode.

According to the method of nucleic acid sequence-based amplification (NASBA), molecular beacons are used for quantification of the NASBA RNA amplicon in real-time analysis (Leone, et al., 1998, *Nucleic Acids Res.* 26: 2150). According to the method of the invention, NASBA can be carried out with a probe comprising at least,two subunits, having a secondary structure that changes upon binding to a target nucleic acid according to the invention.

NASBA amplification is performed essentially as described by Leone G, et al., Nucleic Acids Res. 26: 2150–2155 (1998). Genomic RNA from the potato leafroll virus (PLRV) is amplified using the PD415 or PD416 (antisense) and the PD417 (sense) primers, which are described in detail in Leone G et al., J. Virol. Methods 66: 19–27 (1997). Each NASBA reaction contains a premix of 6 µl of sterile water, 4 µl of 5× NASBA buffer (5× NASBA buffer is 200 mM Tris-HCl, pH 8.5, 60 mM MgCl$_2$, 350 mM KCl, 2.5 mM DTT, 5 mM each of dNTP, 10 mM each of ATP, UTP and CTP, 7.5 mM GTP and 2.5 mM ITP), 4 µl of 5× primer mix (75% DMSO and 1 µM each of antisense and sense primers). The premix is divided into 14 µl aliquots, to which 1 µl of PLRV target is added. After incubation for 5 minutes at 65° C. and cooling to 41° C. for 5 minutes, 5 µl of enzyme mix is added (per reaction 375 mM sorbitol, 2.1 µg BSA, 0.08 units of RNase H (Pharmacia), 32 units of T7 RNA polymerase (Pharmacia) and 6.4 units of AMV-RT (Seigakaku)). Amplification is for 90 minutes at 41° C.

Five µl of each sample in duplicate are removed for detection. Each reaction contains 1× Cloned Pfu buffer, 3.0 mM MgCl$_2$, 200 uM of each dNTP, 5 units Pfu, 300 nM each upstream primer PD415 or PD416 and the fluorogenic probe (for example FAM-DABCYL): gcaaagtatcatccctccag. The reactions are subjected to one cycle in a thermal cycler: 2 minutes at 95° C., 1 minute at 55° C., 1 minute at 72° C. The fluorescence in then determined in a fluorescence plate reader, such as Stratagene's FluorTracker or PE Biosystems' 7700 Sequence Detection System in Plate-Read Mode.

Detection of released, labeled subunits of a probe is performed as described in the section entitled "Detection Complex" and may occur concurrently with (real time) or after (end-point) the amplification has been completed.

Endpoint assays can be used to quantify amplified target produced by non-PCR based methods according to the invention (described above).

Endpoint assays include, but are not limited to the following.

A. Ligation chain reaction (LCR), as described in Landegren, et al., 1988, *Science*, 241: 1077 and Barany, PCR Methods and Applications 1: 5–16 (1991).

B. Self-sustained sequence replication amplification (3SR) Fahy, et al. PCR Methods and Applications 1: 25–33 (1991). Self-Sustained Sequence Replication Amplification (3SR) is a technique which is similar to NASBA. Ehricht R, et al., Nucleic Acids Res. 25: 4697–4699 (1997) have evolved the 3SR procedure to a cooperatively coupled in vitro amplification system (CATCH). Thus, in one embodiment of the invention, a molecular beacon probe is used for real-time analysis of an RNA amplicon by CATCH. The synthetic target amplified has the sequence: cctctgcagactac-tattacataatacgactcactatagggatc tgcacgtattagcctatagtgagtcg-tattaataggaaacaccaaagatgatatttcgtcacagcaagaattcagg (SEQ ID NO: 8). The 3SR reactions contain 40 mM Tris-HCl pH 8.0, 5 mM KCl, 30 mM MgCl$_2$, 1 mM of each dNTP, 1 nM of the double stranded target, 2 µM P1: cctctgcagactactattac (SEQ ID NO: 9) and P2:cctgaattcttgctgtgacg (SEQ ID NO: 10), 5 mM DTT, 2 mM spermidine, 6 units/ul His tagged HIV-1 reverse transcriptase, 3 units/ul T7-RNA polymerase and 0.16 units/ul *Escherichia coli* RNase H. The 100 ul reactions are incubated for 30 minutes at 42° C.

Five µl of each sample in duplicate are removed for detection. Each reaction contains 1× Cloned Pfu buffer, 3.0 mM MgCl$_2$, 200 uM of each dNTP, 5 units Pfu, 300 nM each upstream primer P1 and fluorogenic probe (for example FAM-DABCYL): taggaaacaccaaagatgatattt (SEQ ID NO: 11). The reactions are subjected to one cycle in a thermal cycler: 2 minutes at 95° C., 1 minute at 55° C., 1 minute at 72° C. The fluorescence in then determined in a fluorescence plate reader, such as Stratagene's FluorTracker or PE Bio-systems' 7700 Sequence Detection System in Plate-Read Mode. The method of 3SR can also be carried out with a polymerase that exhibits 5' to 3' exonuclease activity.

C. Rolling circle amplification is described in U.S. Pat. No. 5,854,033 and the related Ramification-Extension Amplification Method (RAM) (U.S. Pat. No. 5,942,391). Rolling circle amplification adapted to the invention is described below.

Real-time assays can also be used to quantify amplified target produced by non-PCR based methods (described above). The method of rolling circle amplification (U.S. Pat. No. 5,854,033) is adapted to include secondary primers for amplification and detection, in conjunction with a probe comprising at least two subunits, having a secondary structure that changes upon hybridization to a target nucleic acid, according to the invention, and is carried out at temperatures between 50–60° C.

The method of the invention can be used to generate a signal indicative of the presence of a sequence variation in a target nucleic acid sequence, wherein a labeled detection complex comprising a fully annealed DNA primer is formed by incubating a target nucleic acid sequence with a probe having a secondary structure that changes upon hybridization to a target nucleic acid, according to the invention (as described in the section entitled, "Detection complex") wherein the release of a labeled subunit of the probe and the detection of a released labeled subunit of the probe, is indicative of the presence of a sequence variation. A released labeled subunit of a probe is detected as described in the section entitled, "Detection complex".

V. Samples

The invention provides for a method of detecting or measuring a target nucleic acid sequence in a sample, as defined herein. As used herein, "sample" refers to any substance containing or presumed to contain a nucleic acid of interest (a target nucleic acid sequence) or which is itself a target nucleic acid sequence, containing or presumed to contain a target nucleic acid sequence of interest. The term "sample" thus includes a sample of target nucleic acid sequence (genomic DNA, cDNA or RNA), cell, organism, tissue, fluid or substance including but not limited to, for example, plasma, serum, spinal fluid, lymph fluid, synovial fluid, urine, tears, stool, external secretions of the skin, respiratory, intestinal and genitourinary tracts, saliva, blood cells, tumors, organs, tissue, samples of in vitro cell culture constituents, natural isolates (such as drinking water, seawater, solid materials,) microbial specimens, and objects or specimens that have been "marked" with nucleic acid tracer molecules.

EXAMPLES

The invention is illustrated by the following nonlimiting examples wherein the following materials and methods are employed. The entire disclosure of each of the literature references cited hereinafter are incorporated by reference herein.

Example 1

Probe Design and Preparation

The invention provides for a probe having two subunits wherein a subunit of the probe dissociates from the remaining subunits of the probe upon binding to a target nucleic acid. The invention also provides for a probe comprising at least two subunits and a secondary structure that changes upon binding of the probe to a target nucleic acid sequence. A probe according to this embodiment of the invention also binds to a target nucleic acid such that a subunit of the probe dissociates from the remaining probe subunits.

A subunit of a probe according to one embodiment of the invention is 5–250 nucleotides in length and ideally 17–40 nucleotides in length. At least one subunit of the probe has a target nucleic acid binding sequence that is from 7 to about 140 nucleotides, and preferably from 10 to about 140 nucleotides. Probes may also comprise non-covalently bound or covalently bound subunits, or a combination thereof.

In one embodiment of the invention, upon hybridization to a target nucleic acid, a subunit of the probe dissociates from the remaining subunit(s) of the probe and is released. In embodiments of the invention wherein the probe further comprises a secondary structure that changes upon binding of the probe to a target nucleic acid, upon hybridization to a target nucleic acid, the probe undergoes a change in secondary structure such that a subunit of the probe dissociates from the remaining subunits and is released. Binding of the probe to the target nucleic acid sequence is performed at a binding temperature. Binding is carried out at a binding temperature wherein a subunit of the probe does not dissociate from the remaining subunit(s) of the probe when not bound to the target nucleic acid sequence at or below the binding temperature. In embodiments wherein the probe comprises a secondary structure, binding is carried out at a binding temperature wherein the secondary structure of the probe when not bound to the target nucleic acid sequence is stable at or below the binding temperature. Furthermore, the first subunit of the probe does not dissociate from the second subunit of the probe when not bound to the target nucleic acid sequence at or below the binding temperature.

A probe according to the invention is labeled with an appropriate pair of interactive labels (e.g., a FRET pair or a non-FRET-pair). The location of the interactive labels on the probe is such that an appropriate spacing of the labels on the probe is maintained to permit the separation of the labels upon dissociation of the first subunit of the probe from a second subunit of the probe. For example, the donor and quencher moieties are positioned on the probe to quench the generation of a detectable signal when the probe is not bound to the target nucleic acid, and when the first and second subunits of the probe are not dissociated.

In one embodiment, the first subunit of the probe is labeled with a fluorophore and the second subunit is labeled with a quencher (for example, tetramethylrhodamine and DABCYL, or any of the fluorophore and quencher molecules described herein (see the section entitled "How To Prepare a Labeled Detection Complex").

One embodiment of a probe comprises secondary structure that changes upon binding of the probe to a target nucleic acid, for example, due to the presence of a first subunit that comprises a first complementary nucleic acid sequence and a second subunit that comprises a second complementary nucleic acid sequence.

In one embodiment, in the absence of the target nucleic acid the probe folds back on itself to generate an antiparallel duplex structure wherein the first and second complementary nucleic acid sequences anneal by the formation of hydrogen bonds to form a secondary structure. The secondary structure of the probe is detected by performing a FRET or fluorescence quenching assay at different temperatures, including temperatures that are above and below the Tm of the probe, as described herein. A probe that exhibits a change in fluorescence that correlates with a change in temperature (e.g., fluorescence increases as the temperature of the FRET reaction is increased), greater than a change in fluorescence simply due to thermal effects on the efficiency of fluorophore emission, has secondary structure. Secondary structure is eliminated at a temperature wherein the maximal level of fluorescence is detected (e.g., fluorescence does not increase above this level at increased temperatures). The stability of the secondary structure of the probe is determined in a melting temperature assay, by FRET or by a fluorescence quenching assay, as described herein.

In the presence of the target nucleic acid sequence, and at a temperature that is selected according to the factors that influence the efficiency and selectivity of hybridization of the probe to the target nucleic acid sequence, (e.g, probe subunit length, nucleotide sequence and/or composition, buffer composition, as described in the section entitled, "Primers and Probes Useful According to the Invention") to permit specific binding of the probe and the target nucleic acid, the probe binds to the target nucleic acid and undergoes a change in the secondary structure such that a subunit of the probe dissociates from the remaining subunits of the probe. A change in the secondary structure of the probe can be determined by FRET or fluorescence quenching, as described herein.

In one embodiment, first and second complementary nucleic acid sequences are 3–25, preferably 4–15 and more preferably 5–11 nucleotides long. The length of the first and second complementary nucleic acid sequences is selected such that the first subunit of the probe does not dissociate from the second subunit of the probe when not bound to the target nucleic acid sequence at or below the binding temperature. The length of the first and second complementary nucleic acid sequences is also selected such that the secondary structure of the probe when not bound to the target nucleic acid sequence is stable at the temperature at which binding of the probe bound to the target nucleic acid is performed. As the target nucleic acid binding sequence increases in size up to 100 nucleotides, the length of the complementary nucleic acid sequences may increase up to 15–25 nucleotides. For a target nucleic acid binding sequence greater than 100 nucleotides, the length of the complementary nucleic acid sequences are not increased further.

Alternatively, an allele discriminating probe comprising, a) at least two subunits or b) at least two subunits and having secondary structure that changes upon binding of the probe to a target nucleic acid is prepared.

In one embodiment, an allele discriminating probe according to the invention preferably comprises a target nucleic acid binding sequence from 6 to 50 and preferably from 7 to 25 nucleotides, and sequences of the complementary nucleic acid sequences from 3 to 8 nucleotides. The guanosine-cytidine content of the secondary structure and probe-target hybrids, salt, and assay temperature are considered, for example magnesium salts have a strong stabilizing effect, when designing short, allele-discriminating probes.

An allele-discriminating probe with a target nucleic acid binding sequence near the upper limits of 50 nucleotides long, is designed such that the single nucleotide mismatch to be discriminated against occurs at or near the middle of the target nucleic acid binding sequence. For example, probes comprising a sequence that is 21 nucleotides long are preferably designed so that the mismatch occurs opposite one of the 14 most centrally located nucleotides of the target nucleic acid binding sequence and most preferably opposite one of the 7 most centrally located nucleotides.

Example 2

A target nucleic acid sequence can be detected and/or measured by the following method. A labeled detection complex is formed by annealing at 95° C. for 5 minutes and then cooling to approximately 50–60° C. (a) a sample containing a target nucleic acid sequence (with (b) a downstream, labeled probe comprising two subunits that specifically hybridizes to a region of the target nucleic acid sequence. Annealing is carried out in the presence of 1× Sentinal Molecular beacon core buffer or 10× Pfu buffer. Following annealing, the labeled first subunit of the probe dissociates from the second subunit of the probe and is released to generate a signal.

Alternatively, a labeled detection complex is formed by annealing a target nucleic acid to a labeled oligonucleotide probe comprising two subunits and having a secondary structure that changes upon binding of the probe to the target nucleic acid sequence and further comprising a binding moiety.

Following annealing, the probe undergoes a change in the secondary structure such that the labeled first subunit of the probe dissociates from a second subunit of the probe. The first subunit of the probe is released to generate a signal.

Following the addition of Sequencing Stop dye solution (included in the Stratagene Cyclist DNA sequencing kit, catalog #200326), samples are heated at 99° C. for five minutes. Samples are loaded on an eleven inch long, hand-poured, 20% acrylamidelbis acrylamide, 7M urea gel. The gel is run at 20 watts until the bromophenol blue has migrated approximately ⅔ the total distance. The gel is removed from the glass plates and soaked for 10 minutes in fix solution (15% methanol, 5% acetic acid) and then for 10 minutes in water. The gel is placed on Whatmann 3 mm paper, covered with plastic wrap and dried for 2 hours in a heated vacuum gel dryer (~80° C.). The gel is exposed overnight to X-ray film to detect the presence of a signal that is indicative of the presence of a target nucleic acid sequence.

Example 3

A target nucleic acid sequence can be detected and/or measured by the following method. A labeled detection complex is formed by heating at 95° C. for 5 minutes and then cooling to approximately 50–60° C. (a) a sample containing a target nucleic acid sequence with (b) an upstream primer that specifically hybridizes to the target nucleic acid sequence, and (c) a downstream, labeled oligonucleotide probe having two subunits that specifically hybridizes to a region of the target nucleic acid sequence that is downstream of the hybridizing region of the upstream primer. A polymerase is added and incubated under conditions that permit the polymerase to extend the upstream primer such that it partially displaces at least a portion of the first subunit of the probe from the target nucleic acid (for example 72° C. in 1× Pfu buffer (Stratagene) for 5 minutes to 1 hour. The displaced subunit of the probe dissociates from a second subunit of the probe and is released to generate a signal. Extension is performed with any of the polymerases included in the section entitled, "Nucleic Acid Polymerases". Alternatively, a labeled detection is formed by annealing a target nucleic acid to a labeled oligonucleotide probe comprising two subunits and having a secondary structure that changes upon binding of the probe to the target nucleic acid sequence. Following annealing, the probe undergoes a change in secondary structure and the labeled first subunit of the probe dissociates from a second subunit of the probe. The first subunit of the probe is released to generate a signal.

Following the addition of Sequencing Stop dye solution (included in the Stratagene Cyclist DNA sequencing kit, catalog #200326), samples are heated at 99° C. for five minutes. Samples are loaded on an eleven inch long, hand-poured, 20% acrylamide/bis acrylamide, 7M urea gel. The gel is run at 20 watts until the bromophenol blue has migrated approximately ⅔ the total distance. The gel is removed from the glass plates and soaked for 10 minutes in fix solution (15% methanol, 5% acetic acid) and then for 10 minutes in water. The gel is placed on Whatmann 3 mm paper, covered with plastic wrap and dried for 2 hours in a heated vacuum gel dryer (~80° C.). The gel is exposed overnight to X-ray film to detect the presence of a signal that is indicative of the presence of a target nucleic acid sequence.

Example 4

PCR Amplification and Detection of β-actin

A PCR assay is used to detect a target nucleic acid sequence. According to the method of this assay, a PCR reaction is carried out in the presence of a probe having two subunits, and a thermostable polymerase (i.e., Taq or Pfu). Alternatively, the PCR assay is carried out in the presence of a probe comprising at least two subunits, having a secondary structure that changes upon binding of a target nucleic acid and comprising a binding moiety or a tag and a thermostable polymerase. Detection of the release of fluorescently labeled first subunits of a probe indicates the presence of the target nucleic acid sequence.

Duplicate PCR reactions containing 1× Sentinel Molecular beacon core buffer, 3.5 mM $MgCl_2$, 200 μM of each dNTP, a Taq or Pfu polymerase, β-Actin primers (300 nM each) and a detection complex prepared as described in Examples 2 and 3 are prepared. The detection complex comprises a β-actin specific fluorogenic probe comprising at least two subunits. 10 ng of human genomic DNA (Promega) is used as the target nucleic acid sequence in each reaction. This reaction is performed in a 50 μl volume. A negative control reaction containing all components except a human genomic DNA template is also prepared. Thermocycling parameters are selected such that the first subunit of the probe does not dissociate from a second subunit of the probe when not bound to the target nucleic acid at or below the binding temperature. For embodiments wherein the probe comprises a secondary structure that changes upon binding to the target nucleic acid, thermocycling parameters are also selected such that the secondary structure of the probe, when not bound to the target nucleic acid is stable at or below the binding temperature. Thermocycling parameters are also selected such that amplification is performed at an amplification temperature. The first subunit of the probe does not dissociate from the second subunit of the probe when not bound to the target nucleic acid sequence at or below the amplification temperature. The secondary structure of the probe, when not bound to the target nucleic acid sequence is stable at or below the amplification temperature. Reactions are assayed in a spectrofluorometric thermocycler (ABI7700). Thermocycling parameters are 95° C. for 2 min and 40 cycles of 95° C. for 15 sec, 60° C. for 60 sec and 72° C. for 15 sec. Samples are interrogated during the annealing step.

Example 5

Figures 1, 1B, 2, 3:
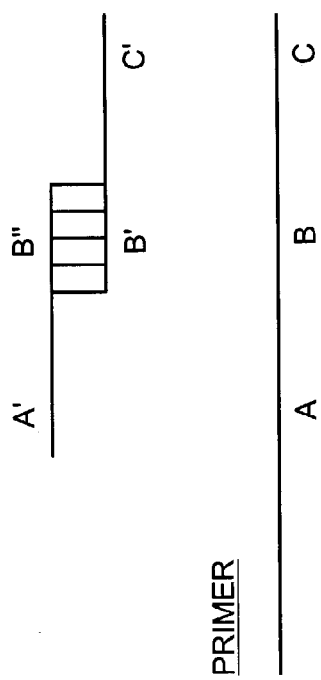
FIG. 3 is a representation of an open circle probe for rolling circle amplification.
Figures 1, 1B, 2, 3, 4:
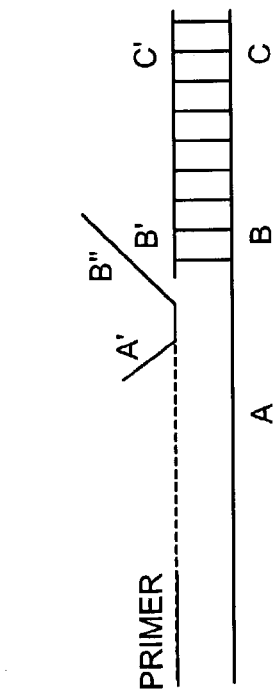
FIG. 4 is a representation of rolling circle amplification.
Figures 1, 1C, 2:
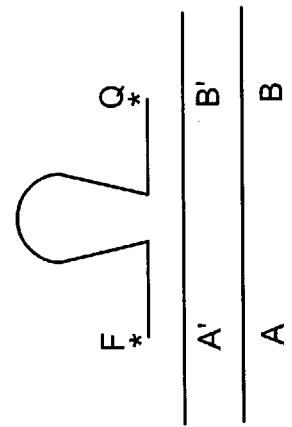
FIG. 1c demonstrates a probe comprising two subunits and a secondary structure that changes upon binding of the probe to the target nucleic acid and a target nucleic acid.
Figures 1, 1C, 2, 3:
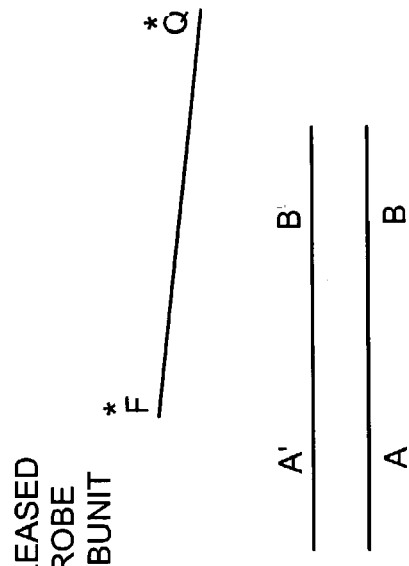
Figures 1, 1C:
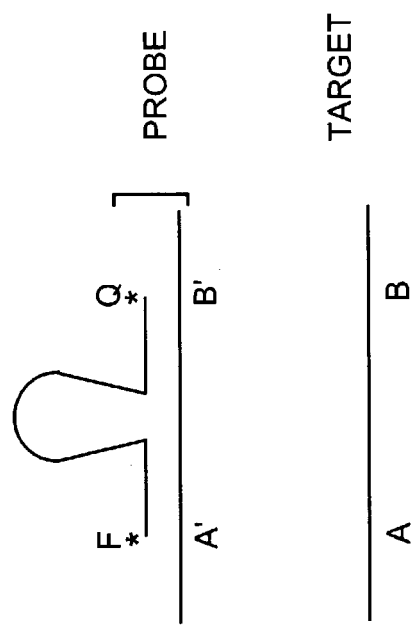
Figure 3:
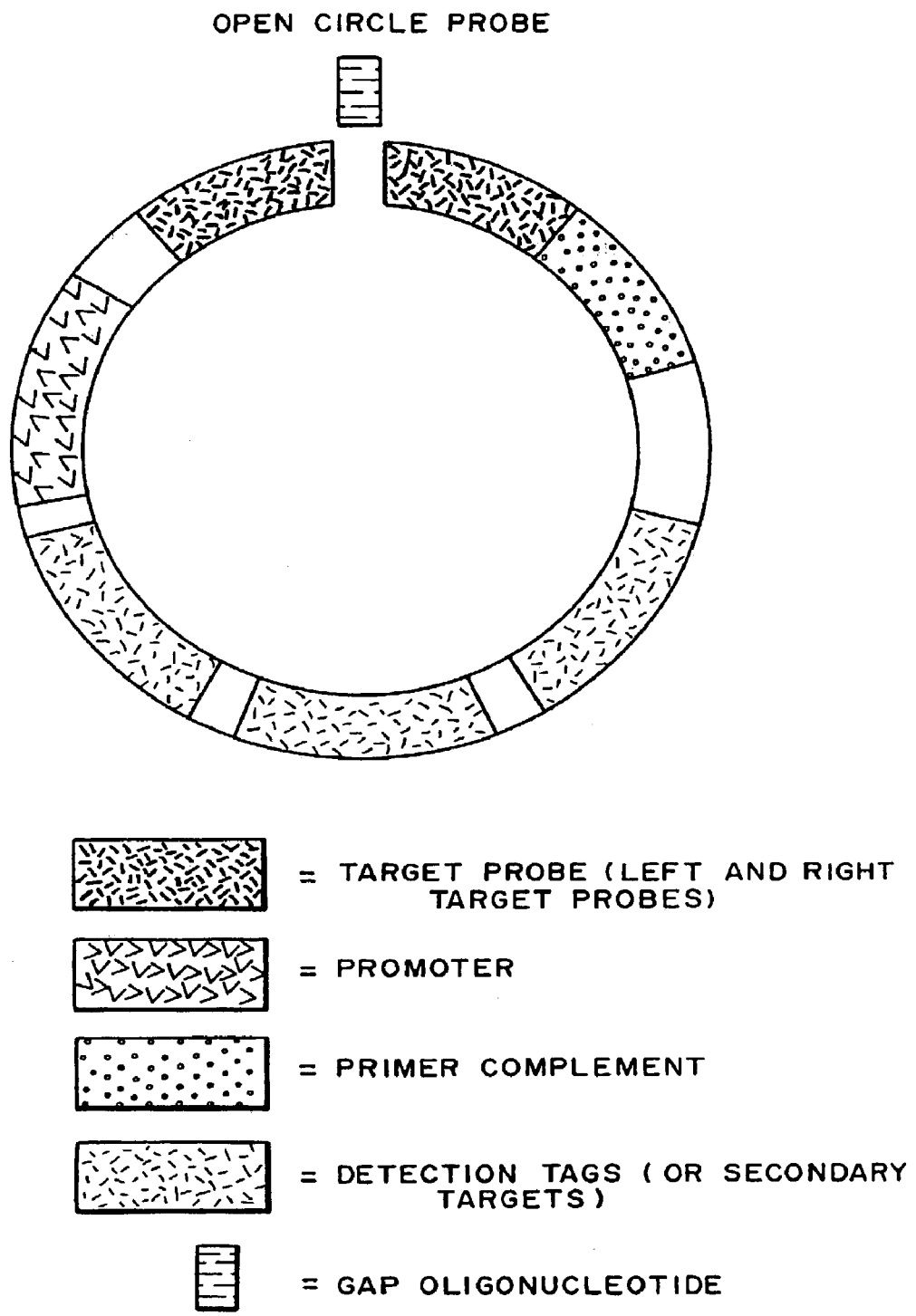
Figure 4:
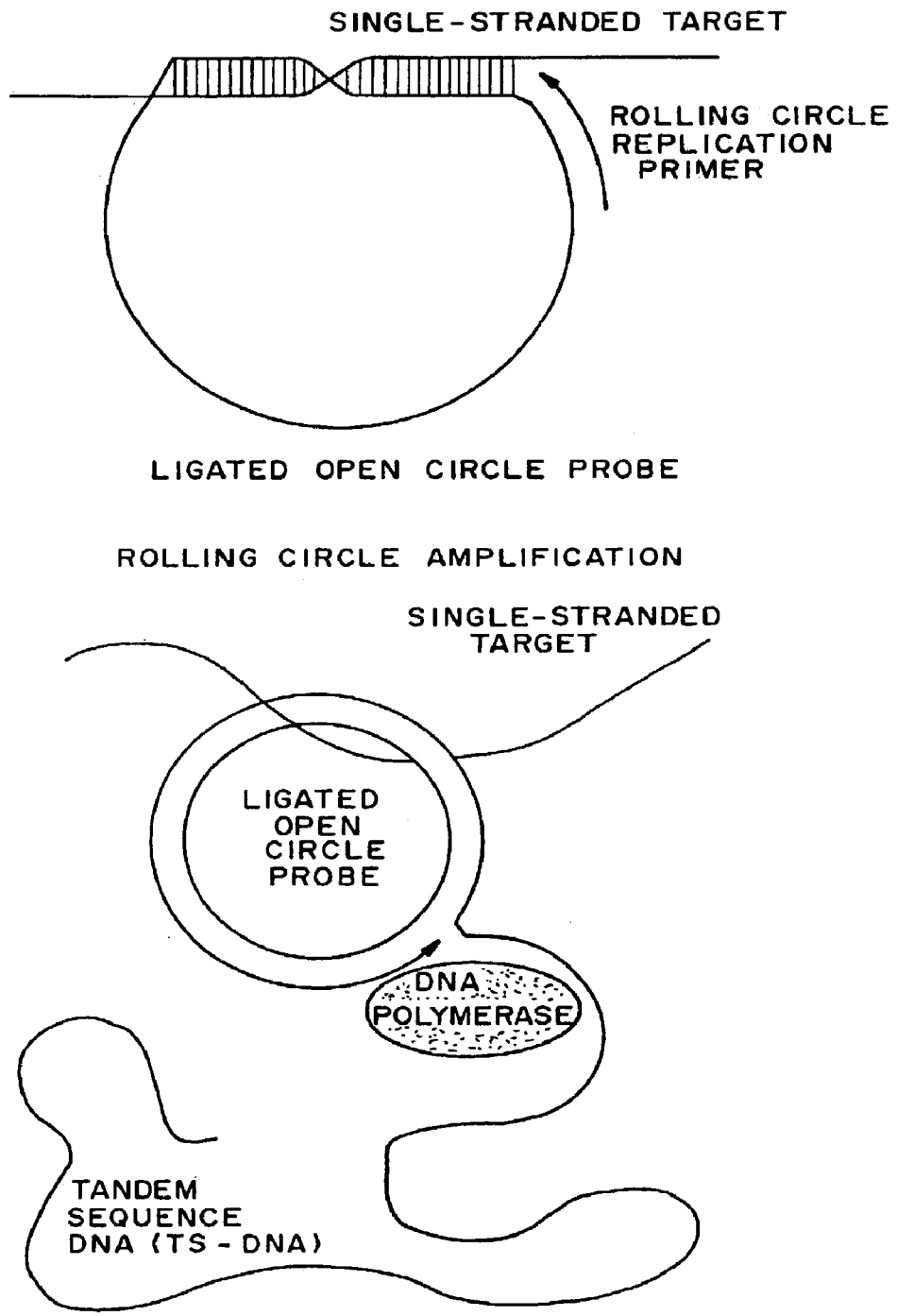

An assay according to the invention involving rolling circle amplification is performed using the human ornithine transcarbamylase gene as a target, which is detected in human DNA extracted from buffy coat by standard procedures. Target (400 ng) is heat-denatured for 4 minutes at 97° C., and incubated under ligation conditions in the presence of two 5'-phosphorylated oligonucleotides, an open circle probe and one gap oligonucleotide. The open circle probe has the sequence: gaggagaataaaagtttctcataagactcgtcatgtctcagcagct-tctaacggtcactaatacgactcactataggttctgcctctgggaacac (SEQ ID NO: 12), the gap nucleotide for the wild-type sequence is: tagtgatc (SEQ ID NO: 13). FIGS. 3 and 4 depict rolling circle probes and rolling circle amplification. The reaction buffer (40 ul) contains 5 units/μl of T4 DNA ligase (New England Biolabs), 10 mM Tris-HCl, pH 7.5, 0.2 M NaCl, 10 mM $MgCl_2$, 4 mM ATP, 80 nM open circle probe and 100 nM gap oligonucleotide. After incubation for 25 minutes at 37° C., 25 ul are removed and added to 25 ul of a solution containing 50 mM Tris-HCl, pH 7.5, 10 mM $MgCl_2$, 1 mM DTT, 400 μM each of dTTP, dATP, dGTP, dCTP, 0.2 μM rolling circle replication primer: gctgagacatgacgagtc (SEQ ID NO: 14), phi29 DNA polymerase (160 ng/50 ul). The sample is incubated for 30 minutes at 30° C.

RNA is produced from a T7 promoter present in the open circle probe, by the addition of a compensating buffer (a stock solution or concentrate) that is diluted to achieve the following concentration of reagents: 35 mM Tris-HCl, pH 8.2, 2 mM spermidine, 18 mm $MgCl_2$, 5 mM GMP, 1 mM of ATP, CTP, GTP, 333 uM UTP, 667 uM Biotin-16-UTP, 0.03% Tween 20, 2 units per ul of T7 RNA polymerase. RNA production is performed as described in U.S. Pat. No. 5,858,033. The incubation is allowed to proceed for 90 minutes at 37° C.

Five μl of each sample (the actual test sample, a (–) ligase control sample, a (–) phi29 DNA polymerase control and a (–) T7 RNA polymerase control) in duplicate are removed for detection. The reverse transcription process includes the steps of A) ligating the open circle, B) synthesizing rolling circle single stranded DNA, C) making RNA (from a T7 promoter present in the open circle probe), D) reverse transcribing the RNA to make cDNA, and E) performing PCR amplification of the cDNA using primers and probes for generation of and detection of detection complexes, according to the invention. For reverse transcription, the reagents and protocols supplied with the Stratagene Sentinel Single-Tube RT-PCR Core Reagent Kit (Cat# 600505) are used, except for the substitution of equal amounts of Yaq DNA polymerase for the Taq 2000 DNA polymerase which is recommended by the manufacturer. Each reaction contains 1× Sentinel molecular beacon RT-PCR core buffer, 3.5 mM $MgCl_2$, 200 μM of each dNTP, 5 units exo- Pfu, 23 ng Pfu FEN-1, 1 ng PEF, 500 nM each of the upstream primer: aagtttctcataagactcgtcat (SEQ ID NO: 15), the reverse primer: aggcagaacctatagtgagtcgt (SEQ ID NO: 16), and the fluorogenic probe comprising at least two subunits (for example labeled with FAM-DABCYL) having a secondary structure, as defined herein, that changes upon binding to the target nucleic acid. The reactions are subjected to incubation for 30 minutes at 45° C., 3 minutes at 95° C., followed by one cycle in a thermal cycler: 2 minutes at 95° C., 1 minute at 50° C., 1 minute at 72° C. The fluorescence in then determined in a fluorescence plate reader, such as Stratagene's FluorTracker or PE Biosystems' 7700 Sequence Detection System in Plate-Read Mode.

A crosscheck for the efficiency of detection is possible because of the incorporation of Biotin-16-UTP in the rolling circle amplification RNA product. An aliquot of the reactions is captured on glass slides (or alternatively in microwell plates) using an immobilized capture probe. Detection of the captured RNA amplicon is described in detail in U.S. Pat. No. 5,854,033, hereby incorporated by reference.

OTHER EMBODIMENTS

Other embodiments will be evident to those of skill in the art. It should be understood that the foregoing detailed description is provided for clarity only and is merely exemplary. The spirit and scope of the present invention are not limited to the above examples, but are encompassed by the following claims.

The invention claimed is:

1. A method of generating a signal indicative of the presence of a target nucleic acid sequence in a sample, comprising forming a detection complex by incubating a sample comprising a target nucleic acid sequence and a probe, wherein said probe comprises:

a first and a second subunit and further comprises: a pair of interactive signal generating labeled moieties effectively positioned on said probe to quench the generation of a detectable signal when the probe is not bound to said target nucleic acid or when said first subunit of the probe is associated with said second subunit of the probe, and wherein said first or second subunit of said probe comprises said pair of interactive signal generating moieties, and binding said probe to said target nucleic acid sequence, wherein said first subunit of said probe dissociates from said second subunit of said probe and wherein said first or second subunit of said probe comprising said pair of interactive signal generating moieties undergoes a conformational change to generate a signal, wherein said binding is performed at a binding temperature and said first subunit of said probe does not dissociate from said second subunit of said probe when not bound to said target nucleic acid sequence at or below said binding temperature, and wherein generation of said signal is indicative of the presence of a target nucleic acid sequence in said sample.

2. A method of generating a signal indicative of the presence of a target nucleic acid sequence in a sample, comprising a) forming a detection complex by incubating a sample comprising a target nucleic acid sequence comprising a first, second and third region, an upstream primer, and a downstream probe, wherein said downstream probe comprises a first and a second subunit, wherein said first and second subunit each comprise a first and second region, wherein said second region of said first subunit is complementary to said first region of said second subunit and said second region of said first subunit binds to said first region of said second subunit when not bound to said target nucleic acid sequence; and wherein said first region of said first subunit is complementary to said first region of said target nucleic acid sequence, said second region of said first subunit is complementary to said second region of said target nucleic acid sequence, said first region of said second subunit is complementary to said second region of said target nucleic acid sequence and said second region of said second subunit is complementary to said third region of said target nucleic acid sequence;

and binding said probe to said target nucleic acid sequence, such that said first region of said first subunit binds to said first region of said target nucleic acid sequence, said first region of said second subunit binds to said second region of said target nucleic acid sequence and said second region of said second subunit binds to said third region of said target nucleic acid sequence, and said first and second subunits dissociate from each other;

b) extending said upstream primer by polymerization of a nucleic acid strand by a nucleic acid polymerization activity, and displacing said first subunit of said probe from said target nucleic acid sequence by said nucleic acid strand, such that said first subunit of said probe dissociates from said target nucleic acid sequence and is released to generate a signal, wherein said binding is performed at a binding temperature and said first subunit of said probe does not dissociate from said second subunit of said probe when not bound to said target nucleic acid sequence at or below said binding temperature, and wherein said polymerization is performed at a polymerization temperature and said first subunit of said probe does not dissociate from said second subunit of said probe when not displaced by said nucleic acid strand at or below said polymerization temperature, and wherein generation of said signal is indicative of the presence of a target nucleic acid sequence in said sample.

3. The method of claim 1 or 2, wherein said signal is detected or measured, and wherein said detecting and/or measuring the signal comprises detecting and/or measuring the amount of said released first subunit.

4. A method of detecting or measuring a target nucleic acid sequence comprising the steps of:

a) forming a detection complex by incubating a sample comprising a target nucleic acid sequence with a probe, wherein said probe comprises:

a first and a second subunit, and further comprises:

a pair of interactive signal generating labeled moieties effectively positioned on said probe to quench the generation of a detectable signal when the probe is not bound to said target nucleic acid or when said first subunit of the probe is associated with said second subunit of the probe, and wherein said first or second subunit of said probe comprises said pair of interactive signal generating moieties, and binding said probe to said target nucleic acid sequence to dissociate said first subunit of said probe from said second subunit of said probe, and wherein said first or second subunit of said probe comprising said pair of interactive signal generating moieties undergoes a conformational change to generate a signal, wherein said binding is performed at a binding temperature and said first subunit of said probe does not dissociate from said second subunit of said probe when not bound to said target nucleic acid sequence at or below said binding temperature; and b) detecting and/or measuring the amount of said released first subunit as an indication of the presence of the target sequence in the sample.

5. A method of detecting or measuring a target nucleic acid sequence comprising a first, second and third region comprising the steps of:

a) forming a detection complex by incubating a sample comprising a target nucleic acid sequence, an upstream primer, and a downstream probe, wherein said probe comprises a first and a second subunit wherein said first and second subunit each comprise a first and second region, wherein said second region of said first subunit is complementary to said first region of said second subunit and said second region of said first subunit binds to said first region of said second subunit when not bound to said target nucleic acid sequence; and wherein said first region of said first subunit is complementary to said first region of said target nucleic acid sequence, said second region of said first subunit is complementary to said second region of said target nucleic acid sequence, said first region of said second subunit is complementary to said second region of said target nucleic acid sequence and said second region of said second subunit is complementary to said third region of said target nucleic acid sequence; and binding said probe to said target nucleic acid sequence such that said first region of said first subunit binds to said first region of said target nucleic acid sequence, said first region of said second subunit binds to said second region of said target nucleic acid sequence and said second region of said second subunit binds to said third region of said target nucleic acid sequence, and said first and second subunits dissociate from each other;

b) extending said upstream primer by polymerization of a nucleic acid strand by a nucleic acid polymerization activity, and displacing said first subunit of said probe from said target nucleic acid sequence by said nucleic acid strand, such that said first subunit of said probe dissociates from said target nucleic acid sequence and is released to generate a signal, wherein said binding is performed at a binding temperature and said first subunit of said probe does not dissociate from said second subunit of said probe when not bound to said target nucleic acid sequence at or below said binding temperature, wherein said polymerization is performed at a polymerization temperature and said first subunit of said probe does not dissociate from said second subunit of said probe when not displaced by said nucleic acid strand, at or below said polymerization temperature, and detecting and/or measuring the amount of said released first subunit as an indication of the presence of the target sequence in the sample.

6. The method of claim 2 or 5 wherein said first subunit of said probe further comprises at least one labeled moiety capable of providing a signal.

7. The method of claim 2 or 5 wherein a detection complex is formed comprising a pair of interactive signal generating labeled moieties effectively positioned on said probe to quench the generation of a detectable signal when the probe is not bound to said target nucleic acid or when said first subunit of said probe is not dissociated from said second subunit of said probe.

8. The method of claim 7 wherein said pair of interactive signal generating moieties comprises a quencher moiety and a fluorescent moiety.

9. A polymerase chain reaction process for detecting a target nucleic acid sequence comprising a first, second and third region in a sample comprising:

(a) providing a detection complex comprising a probe, wherein said probe comprises a first and a second subunit wherein said first and second subunit each comprise a first and second region, wherein said second region of said first subunit is complementary to said first region of said second subunit and said second region of said first subunit binds to said first region of said second subunit when not bound to said target nucleic acid sequence; and wherein said first region of said first subunit is complementary to said first region of said target nucleic acid sequence, said second region of said first subunit is complementary to said second region of said target nucleic acid sequence, said first region of said second subunit is complementary to said second region of said target nucleic acid sequence and said second region of said second subunit is complementary to said third region of said target nucleic acid sequence;

a set of oligonucleotide primers wherein a first primer contains a sequence complementary to a region in one strand of said target nucleic acid sequence and primes the synthesis of a complementary DNA strand, and a second primer contains a sequence complementary to a region in a second strand of the target nucleic acid sequence and primes the synthesis of a complementary DNA strand;

wherein said probe binds to said target nucleic acid sequence such that said first region of said first subunit binds to said first region of said target nucleic acid sequence, said first region of said second subunit binds to said second region of said target nucleic acid sequence and said second region of said second subunit binds to said third region of said target nucleic acid sequence, and said first and second subunits dissociate from each other; and (b) amplifying the target nucleic acid sequence by the steps of (i) annealing of primers required for amplification to a template nucleic acid sequence contained within said target nucleic acid sequence, and (ii) extending the primers wherein said nucleic acid polymerase synthesizes a primer extension product, and thereby dissociates said first subunit of said probe from said target nucleic acid sequence thereby creating detectable, released labeled first subunits of said probe;

wherein said amplification is performed at an amplification temperature and said first subunit of said probe does not dissociate from said second subunit of said probe when not bound to said target nucleic acid sequence at or below said amplification temperature; and (c) detecting and/or measuring the amount of released, labeled first subunit of said probe as an indicator of the presence of the target sequence in the sample.

10. A polymerase chain reaction process for detecting a target nucleic acid sequence comprising a first, second and third region in a sample comprising:

(a) providing a detection complex comprising a probe, wherein said probe comprises a first and a second subunit wherein said first and second subunit each comprise a first and second region, wherein said second region of said first subunit is complementary to said first region of said second subunit and said second region of said first subunit binds to said first region of said second subunit when not bound to said target nucleic acid sequence; and wherein said first region of said first subunit is complementary to said first region of said target nucleic acid sequence, said second region of said first subunit is complementary to said second region of said target nucleic acid sequence, said first region of said second subunit is complementary to said second region of said target nucleic acid sequence and said second region of said second subunit is complementary to said third region of said target nucleic acid sequence; a set of oligonucleotide primers wherein a first primer contains a sequence complementary to a region in one strand of said target nucleic acid sequence and primes the synthesis of a complementary DNA strand, and a second primer contains a sequence complementary to a region in a second strand of the target nucleic acid sequence and primes the synthesis of a complementary DNA strand wherein said probe binds to said target nucleic acid sequence such that said first region of said first subunit binds to said first region of said target nucleic acid sequence, said first region of said second subunit binds to said second region of said target nucleic acid sequence and said second region of said second subunit binds to said third region of said target nucleic acid sequence, and said first and second subunits dissociate from each other; and (b) amplifying the target nucleic acid sequence by the steps of (i) annealing of primers required for amplification to a template nucleic acid sequence contained within said target nucleic acid sequence, (ii) extending the primers wherein said nucleic acid polymerase synthesizes a primer extension product, and (iii) displacing said first subunit of said probe from said target nucleic acid sequence by said primer extension product, such that said first subunit dissociates from said target nucleic acid sequence thereby creating detectable, released labeled first subunits of said probe;

wherein said amplification is performed at an amplification temperature and said first subunit of said probe does not dissociate from said second subunit of said probe when not bound to said target nucleic acid sequence, or when not displaced from said target nucleic acid sequence by said primer extension product, at or below said amplification temperature; and (c) detecting and/or measuring the amount of released, labeled first subunit of said probe as an indication of the presence of the target sequence in the sample.

11. The polymerase chain reaction process of claim 9 wherein said oligonucleotide primers of step b are oriented such that the forward primer is located upstream of said detection complex and the reverse primer is located downstream of said detection complex.

12. The polymerase chain reaction process of claim 9 or 10 wherein the nucleic acid polymerase is thermostable.

13. The polymerase chain reaction process of claim 9 or 10 wherein said labeled detection complex is formed by the addition of a labeled first subunit of said probe capable of providing a signal and a second subunit of said probe.

14. The polymerase chain reaction process of claim 9 or 10 wherein said detection complex is formed comprising a pair of interactive signal generating labeled moieties effectively positioned on said probe to quench the generation of a detectable signal when said probe is not bound to said target nucleic acid or when said first subunit of said probe is not dissociated from said second subunit of said probe.

15. The polymerase chain reaction process of claim 14 wherein said pair of interactive signal generating moieties comprises a quencher moiety and a fluorescent moiety.

16. A method of forming a detection complex comprising the steps of:

(a) providing a target nucleic acid sequence, (b) providing a probe, wherein said probe comprises a first and a second subunit, and further comprises: a pair of interactive signal generating labeled moieties effectively positioned on said probe to quench the generation of a detectable signal when the probe is not bound to said target nucleic acid or when said first subunit of the probe is associated with said second subunit of the probe, and wherein said first or second subunit of said probe comprises said pair of interactive signal generating moieties, and (c) binding said target nucleic acid sequence and said probe and;

wherein said binding is performed at a binding temperature and said first subunit of said probe does not dissociate from said second subunit of said probe when not bound to said target nucleic acid sequence at or below said binding temperature.

17. A method of forming a detection complex comprising the steps of:

(a) providing a target nucleic acid sequence comprising a first, second and third region, (b) providing an upstream primer complementary to said target nucleic acid sequence, (c) providing a probe, wherein said probe comprises a first and a second subunit, wherein each of said first and second subunits comprises a 5' terminus and a 3' terminus, wherein said first and second subunit each comprise a first and second region, wherein said second region of said first subunit is complementary to said first region of said second subunit and said second region of said first subunit binds to said first region of said second subunit when not bound to said target nucleic acid sequence; and wherein said first region of said first subunit is complementary to said first region of said target nucleic acid sequence, said second region of said first subunit is complementary to said second region of said target nucleic acid sequence, said first region of said second subunit is complementary to said second region of said target nucleic acid sequence and said second region of said second subunit is complementary to said third region of said target nucleic acid sequence; and (d) binding said target nucleic acid sequence, said upstream primer and said probe such that said first region of said first subunit binds to said first region of said target nucleic acid sequence, said first region of said second subunit binds to said second region of said target nucleic acid sequence and said second region of said second subunit binds to said third region of said target nucleic acid sequence, and said first and second subunits dissociate from each other; and wherein said binding is performed at a binding temperature and said first subunit of said probe does not dissociate from said second subunit of said probe when not bound to said target nucleic acid sequence at or below said binding temperature, and wherein said 3' terminus of said first and/or second subunit of said probe that is bound to said target nucleic acid sequence is blocked.

18. A composition comprising a target nucleic acid sequence, and probe, wherein said probe comprises a first and a second subunit, and further comprises:

a pair of interactive signal generating labeled moieties effectively positioned on said probe to quench the generation of a detectable signal when the probe is not bound to said target nucleic acid or when said first subunit of the probe is associated with said second subunit of the probe, wherein said first or second subunit of said probe comprises said pair of interactive signal generating moieties, and wherein said probe and said target nucleic acid can bind to form a detection complex and wherein said binding is performed at a binding temperature, and wherein said first subunit of said probe does not dissociate from said second subunit of said probe when not bound to said target nucleic acid sequence at or below said binding temperature.

19. A composition comprising a target nucleic acid sequence comprising a first, second and third region, a probe, wherein said probe comprises a first and a second subunit, wherein each of said first and second subunits comprises a 5' terminus and a 3' terminus, wherein said first and second subunit each comprise a first and second region, wherein said second region of said first subunit is complementary to said first region of said second subunit and said second region of said first subunit binds to said first region of said second subunit when not bound to said target nucleic acid sequence; and wherein said first region of said first subunit is complementary to said first region of said target nucleic acid sequence, said second region of said first subunit is complementary to said second region of said target nucleic acid sequence, said first region of said second subunit is complementary to said second region of said target nucleic acid sequence and said second region of said second subunit is complementary to said third region of said target nucleic acid sequence, an upstream primer and a nucleic acid polymerization activity, wherein said probe, said primer and said target nucleic acid can bind to form a detection complex, wherein said probe binds to said target nucleic acid sequence such that said first region of said first subunit binds to said first region of said target nucleic acid sequence, said first region of said second subunit binds to said second region of said target nucleic acid sequence and said second region of said second subunit binds to said third region of said target nucleic acid sequence, and said first and second subunits dissociate from each other;

and wherein said binding is performed at a binding temperature, and wherein said first subunit of said probe does not dissociate from said second subunit of said probe when not bound to said target nucleic acid sequence at or below said binding temperature, and wherein said 3' terminus of said first and/or second subunit of said probe that is bound to said target nucleic acid sequence is blocked.

20. A kit for generating a signal indicative of the presence of a target nucleic acid sequence in a sample, comprising a probe, wherein said probe comprises a first and a second subunit and further comprises:

a pair of interactive signal generating labeled moieties effectively positioned on said probe to quench the generation of a detectable signal when the probe is not bound to said target nucleic acid or when said first subunit of the probe is associated with said second subunit of the probe, wherein said first or second subunit of said probe comprises said pair of interactive signal generating moieties, and packaging means thereof, wherein said probe can bind to a target nucleic acid sequence to form a detection complex; and wherein said binding is performed at a binding temperature, and wherein said first subunit of said probe does not dissociate from said second subunit of said probe when not bound to said target nucleic acid sequence at or below said binding temperature.

21. A kit for generating a signal indicative of the presence of a target nucleic acid sequence comprising a first, second and third region in a sample comprising an upstream primer, and a downstream probe, wherein said probe comprises a first and a second subunit, wherein each of said first and second subunits comprises a 5' terminus and a 3' terminus, wherein said first and second subunit each comprise a first and second region, wherein said second region of said first subunit is complementary to said first region of said second subunit and said second region of said first subunit binds to said first region of said second subunit when not bound to said target nucleic acid sequence; and wherein said first region of said first subunit is complementary to said first region of said target nucleic acid sequence, said second region of said first subunit is complementary to said second region of said target nucleic acid sequence, said first region of said second subunit is complementary to said second region of said target nucleic acid sequence and said second region of said second subunit is complementary to said third region of said target nucleic acid sequence, and a nucleic acid polymerization activity, and packaging means thereof, wherein said primer and said probe can bind to a target nucleic acid sequence to form a detection complex, wherein said probe binds to said target nucleic acid sequence such that said first region of said first subunit binds to said first region of said target nucleic acid sequence, said first region of said second subunit binds to said second region of said target nucleic acid sequence and said second region of said second subunit binds to said third region of said target nucleic acid sequence, and said first and second subunits dissociate from each other; and wherein said binding is performed at a binding temperature, and wherein said first subunit of said probe does not dissociate from at least said second subunit of said probe when not bound to said target nucleic acid sequence at or below said binding temperature, and wherein said 3' terminus of said first and/or second subunit of said probe that is bound to said target nucleic acid sequence is blocked.

22. The kit of claim 21, wherein said probe comprises a labeled first subunit of said probe and a second subunit of said probe.

23. The kit of claim 21, wherein said first subunit of said probe comprises a pair of interactive signal generating labeled moieties effectively positioned to quench the generation of a detectable signal when said probe is not bound to said target nucleic acid or when said first subunit of said probe is not dissociated from said second subunit of said probe.

24. The kit of claim 23, wherein said pair of interactive signal generating moieties comprises a quencher moiety and a fluorescent moiety.

25. The method of claim 2, wherein only one subunit of said probe is displaced from said target nucleic acid sequence by said nucleic acid strand in step (b).

26. The method of claim 5, wherein only one subunit of said probe is displaced from said target nucleic acid sequence by said nucleic acid strand in step (b).

27. The polymerase chain reaction process of claim 10, wherein only one subunit of said probe is displaced from said target nucleic acid sequence by said primer extension product in step (b).

28. The method of claim 2, wherein the 3' terminus of the subunit of the probe that is bound to said target nucleic acid sequence is blocked.

29. The method of claim 5, wherein the 3' terminus of the subunit of the probe that is bound to said target nucleic acid sequence is blocked.

30. The polymerase chain reaction process of claim 9, wherein a subunit of the probe binds said target nucleic acid and wherein the 3' terminus of the subunit of the probe that is bound to said target nucleic acid sequence is blocked.

31. The polymerase chain reaction process of claim 10, wherein a subunit of the probe binds said target nucleic acid and wherein the 3' terminus of the subunit of the probe that is bound to said target nucleic acid sequence is blocked.

* * * * *